US011514207B2

(12) United States Patent
Santarone et al.

(10) Patent No.: US 11,514,207 B2
(45) Date of Patent: *Nov. 29, 2022

(54) TRACKING SAFETY CONDITIONS OF AN AREA

(71) Applicant: Middle Chart, LLC, Jacksonville, FL (US)

(72) Inventors: Michael S. Santarone, Jacksonville, FL (US); Michael Wodrich, Jacksonville, FL (US); Randall Pugh, Jacksonville, FL (US); Jason E. Duff, Jacksonville, FL (US)

(73) Assignee: Middle Chart, LLC, Jacksonville, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 17/196,146

(22) Filed: Mar. 9, 2021

(65) Prior Publication Data
US 2021/0216677 A1      Jul. 15, 2021

Related U.S. Application Data

(63) Continuation of application No. 16/935,857, filed on Jul. 22, 2020, now Pat. No. 10,984,146, which is a
(Continued)

(51) Int. Cl.
*G06F 30/13* (2020.01)
*G06T 19/00* (2011.01)
(Continued)

(52) U.S. Cl.
CPC .............. *G06F 30/13* (2020.01); *G01S 19/48* (2013.01); *G06Q 99/00* (2013.01); *G06T 17/05* (2013.01); *G06T 19/006* (2013.01); *G01S 19/01* (2013.01)

(58) Field of Classification Search
CPC .......... G06F 30/13; G01S 19/48; G01S 19/01; G01S 3/48; G01S 3/78; G01S 5/02;
(Continued)

(56) References Cited

U.S. PATENT DOCUMENTS 5,884,202 A   3/1999 Arjomand
5,933,479 A   8/1999 Michael et al.
(Continued)

FOREIGN PATENT DOCUMENTS

CN   102147597 A   8/2011
EP      2726817 B1   9/2018
(Continued)

OTHER PUBLICATIONS

Amekudzi, Adjo A., Rebecca Shelton, and Tim R. Bricker. "Infrastructure Rating Tool: Using Decision Support Tools to Enhance ASCE Infrastructure Report Card Process." Leadership and Management in Engineering 13.2 (2013): 76-82. (Year: 2013).
(Continued)

*Primary Examiner* — Brandon J Miller
(74) *Attorney, Agent, or Firm* — Tracnik Law, PLLC

(57) ABSTRACT

Apparatus for electronically quantifying conditions of a person and an environment containing the person, as well as a sequence of positions occupied by the person and a direction the person faced at those positions. Wireless communications track a series of positions over time and provide user interfaces indicating where a person has been and who the person has come within a minimum distance of. Sensors may be operative to provide ongoing evaluation of a condition of the person, such as a body temperature and heartrate which may trigger an alarm state if the body temperature rises above a specified value. Electronic sensors may also be quantify environmental conditions over time and present the conditions in the user interface.

25 Claims, 28 Drawing Sheets

Related U.S. Application Data continuation-in-part of application No. 16/900,753, filed on Jun. 12, 2020, now Pat. No. 10,872,179, which is a continuation-in-part of application No. 16/721,906, filed on Dec. 19, 2019, now Pat. No. 10,726,167, and a continuation-in-part of application No. 16/817,926, filed on Mar. 13, 2020, now Pat. No. 10,831,945, which is a continuation-in-part of application No. 16/688,775, filed on Nov. 19, 2019, now Pat. No. 10,628,617, which is a continuation-in-part of application No. 16/657,660, filed on Oct. 18, 2019, now abandoned, which is a continuation-in-part of application No. 16/597,271, filed on Oct. 9, 2019, which is a continuation of application No. 16/161,823, filed on Oct. 16, 2018, now Pat. No. 10,467,353, which is a continuation-in-part of application No. 15/716,133, filed on Sep. 26, 2017, now Pat. No. 10,025,887, said application No. 16/161,823 is a continuation-in-part of application No. 15/703,310, filed on Sep. 13, 2017, said application No. 16/597,271 is a continuation of application No. 15/887,637, filed on Feb. 2, 2018, which is a continuation-in-part of application No. 15/716,133, filed on Sep. 26, 2017, now Pat. No. 10,025,887, and a continuation-in-part of application No. 15/703,310, filed on Sep. 13, 2017, said application No. 16/657,660 is a continuation-in-part of application No. 16/549,503, filed on Aug. 23, 2019, now Pat. No. 11,054,335, and a continuation-in-part of application No. 16/528,104, filed on Jul. 31, 2019, now Pat. No. 10,671,767, which is a continuation-in-part of application No. 16/504,919, filed on Jul. 8, 2019, now Pat. No. 10,740,502, which is a continuation-in-part of application No. 16/503,878, filed on Jul. 5, 2019, now Pat. No. 10,776,529, which is a continuation-in-part of application No. 16/297,383, filed on Mar. 8, 2019, now Pat. No. 10,762,251, which is a continuation-in-part of application No. 16/176,002, filed on Oct. 31, 2018, now Pat. No. 10,268,782, which is a continuation-in-part of application No. 16/171,593, filed on Oct. 26, 2018, now Pat. No. 10,620,084, which is a continuation-in-part of application No. 16/165,517, filed on Oct. 19, 2018, now Pat. No. 10,733,334, which is a continuation-in-part of application No. 16/161,823, filed on Oct. 16, 2018, now Pat. No. 10,467,353, and a continuation-in-part of application No. 16/142,275, filed on Sep. 26, 2018, now Pat. No. 10,433,112, and a continuation-in-part of application No. 15/887,637, filed on Feb. 2, 2018, said application No. 16/503,878 is a continuation-in-part of application No. 16/249,574, filed on Jan. 16, 2019, now Pat. No. 10,831,943, which is a continuation-in-part of application No. 16/176,002, filed on Oct. 31, 2018, now Pat. No. 10,268,782, and a continuation-in-part of application No. 16/503,878, filed on Jul. 5, 2019, now Pat. No. 10,776,529, said application No. 16/935,857 is a continuation-in-part of application No. 16/775,223, filed on Jan. 28, 2020, now Pat. No. 10,740,503, and a continuation-in-part of application No. 16/915,155, filed on Jun. 29, 2020, now Pat. No. 10,943,034, and a continuation-in-part of application No. 16/905,048, filed on Jun. 18, 2020, now Pat. No. 10,885,234, and a continuation-in-part of application No. 16/898,602, filed on Jun. 11, 2020, now Pat. No. 10,949,579.

(60) Provisional application No. 62/531,955, filed on Jul. 13, 2017, provisional application No. 62/531,975, filed on Jul. 13, 2017, provisional application No. 62/462,347, filed on Feb. 22, 2017, provisional application No. 62/909,061, filed on Oct. 1, 2019, provisional application No. 62/712,714, filed on Jul. 31, 2018, provisional application No. 62/793,714, filed on Jan. 17, 2019, provisional application No. 62/871,499, filed on Jul. 8, 2019, provisional application No. 62/769,133, filed on Nov. 19, 2018.

(51) Int. Cl.
*G06Q 99/00* (2006.01)
*G01S 19/48* (2010.01)
*G06T 17/05* (2011.01)
*G01S 19/01* (2010.01)

(58) Field of Classification Search
CPC .. G01S 17/42; G01S 2205/01; G01S 2205/09; G06Q 99/00; G06T 17/05; G06T 19/006; G08B 21/0453; G08B 21/0272; G08B 21/0275; G08B 21/22; G16H 40/67; G16H 50/80
See application file for complete search history.

(56) References Cited

U.S. PATENT DOCUMENTS

| | | |
|---|---|---|
| 6,006,021 A | 12/1999 | Tognazzini |
| 6,292,108 B1 | 9/2001 | Straser et al. |
| 6,321,158 B1 | 11/2001 | DeLorme et al. |
| 6,853,958 B1 | 2/2005 | Turin et al. |
| 6,963,282 B1 | 11/2005 | Yeates et al. |
| 7,057,557 B2 | 6/2006 | Lee |
| 8,818,758 B1 | 8/2014 | Singh et al. |
| 8,843,350 B2 | 9/2014 | Jacobi et al. |
| 8,862,415 B1 | 10/2014 | Adams |
| 8,965,741 B2 | 2/2015 | McCulloch et al. |
| 8,996,156 B2 | 3/2015 | Melzer-Jokisch et al. |
| 9,037,124 B1 | 5/2015 | Ledet |
| 9,064,219 B2 | 6/2015 | Hall et al. |
| 9,342,928 B2 | 5/2016 | Rasane et al. |
| 9,529,072 B2 | 12/2016 | Matzner |
| 9,703,517 B2 | 7/2017 | Andolina |
| 9,772,396 B2 | 9/2017 | Liao et al. |
| 9,792,020 B1 | 10/2017 | Kelley et al. |
| 9,952,569 B2 | 4/2018 | Brissman |
| 10,054,914 B2 | 8/2018 | Vartiainen et al. |
| 10,149,141 B1 | 12/2018 | Stamatakis et al. |
| 10,222,301 B2 | 3/2019 | Silva et al. |
| 10,278,016 B2 | 4/2019 | Bitra et al. |
| 10,295,647 B1 | 5/2019 | Hulvey |
| 10,355,351 B2 | 7/2019 | Cummings et al. |
| 10,444,324 B2 | 10/2019 | Dackefjord et al. |
| 10,825,247 B1 | 11/2020 | Vincent et al. |
| 10,872,179 B2 | 12/2020 | Wodrich et al. |
| 10,984,146 B2 * | 4/2021 | Santarone ................. G01S 5/02 |
| 11,080,439 B2 | 8/2021 | Wodrich et al. |
| 11,100,260 B2 | 8/2021 | Wodrich et al. |
| 11,194,938 B2 | 12/2021 | Kincart et al. |
| 2002/0095269 A1 | 7/2002 | Natalini et al. |
| 2002/0181405 A1 | 12/2002 | Ying |
| 2003/0110001 A1 | 6/2003 | Chassin et al. |
| 2003/0135324 A1 | 7/2003 | Navab |
| 2003/0163440 A1 | 8/2003 | Tonack |
| 2003/0195008 A1 | 10/2003 | Mohi et al. |
| 2004/0002786 A1 | 1/2004 | Sasaki |
| 2004/0119662 A1 | 6/2004 | Dempski |
| 2004/0122628 A1 | 6/2004 | Laurie |
| 2005/0165576 A1 | 7/2005 | Jesmonth |
| 2005/0275525 A1 | 12/2005 | Ahmed |
| 2006/0028345 A1 | 2/2006 | Lee |
| 2006/0084436 A1 | 4/2006 | Green et al. |
| 2006/0084463 A1 | 4/2006 | Yoo et al. |
| 2006/0164382 A1 | 7/2006 | Kulas et al. |
| 2007/0004449 A1 | 1/2007 | Sham |

(56) References Cited

U.S. PATENT DOCUMENTS

| | | |
|---|---|---|
| 2007/0266395 A1 | 11/2007 | Lee et al. |
| 2008/0180246 A1 | 7/2008 | Malik |
| 2008/0246734 A1 | 10/2008 | Tsui et al. |
| 2009/0189810 A1 | 7/2009 | Murray |
| 2009/0216438 A1 | 8/2009 | Shafer |
| 2009/0293051 A1 | 11/2009 | Krywaniuk |
| 2010/0103036 A1 | 4/2010 | Malone et al. |
| 2010/0240339 A1* | 9/2010 | Diamond ............... H04H 20/59 455/404.2 |
| 2010/0271263 A1 | 10/2010 | Moshfeghi |
| 2010/0296075 A1 | 11/2010 | Hinderling et al. |
| 2010/0309044 A1 | 12/2010 | Ische et al. |
| 2011/0047516 A1 | 2/2011 | Pavan et al. |
| 2011/0068906 A1 | 3/2011 | Shafer et al. |
| 2011/0075835 A1 | 3/2011 | Hill |
| 2011/0115816 A1 | 5/2011 | Brackney |
| 2011/0182202 A1 | 7/2011 | Olofsson et al. |
| 2011/0199479 A1 | 8/2011 | Waldman |
| 2011/0251787 A1 | 10/2011 | Gupta et al. |
| 2012/0087212 A1 | 4/2012 | Vartanian et al. |
| 2012/0127306 A1 | 5/2012 | Oh et al. |
| 2012/0127976 A1 | 5/2012 | Lin et al. |
| 2012/0173456 A1 | 7/2012 | Hirl |
| 2012/0188847 A1 | 7/2012 | Miyamoto et al. |
| 2012/0204646 A1 | 8/2012 | Lee et al. |
| 2012/0214507 A1 | 8/2012 | Vartanian et al. |
| 2012/0259594 A1 | 10/2012 | Khan et al. |
| 2012/0296610 A1 | 11/2012 | Hailemariam et al. |
| 2013/0010103 A1 | 1/2013 | Ihara et al. |
| 2013/0084886 A1 | 4/2013 | Crilly, Jr. et al. |
| 2013/0120630 A1 | 5/2013 | Kim et al. |
| 2013/0169801 A1 | 7/2013 | Martin et al. |
| 2013/0197685 A1 | 8/2013 | Matsunaga et al. |
| 2013/0223261 A1 | 8/2013 | Aggarwal et al. |
| 2013/0283529 A1 | 10/2013 | Hayes et al. |
| 2013/0288719 A1 | 10/2013 | Alonzo |
| 2013/0297555 A1 | 11/2013 | Fadell et al. |
| 2013/0345975 A1 | 12/2013 | Vulcano et al. |
| 2014/0058572 A1 | 2/2014 | Stein et al. |
| 2014/0084909 A1 | 3/2014 | Pagani |
| 2014/0107828 A1 | 4/2014 | Zhu et al. |
| 2014/0129599 A1 | 5/2014 | Boccon-Gibod |
| 2014/0146038 A1 | 5/2014 | Kangas et al. |
| 2014/0156455 A1 | 6/2014 | Atwood et al. |
| 2014/0188394 A1 | 7/2014 | Febonio et al. |
| 2014/0210856 A1 | 7/2014 | Finn et al. |
| 2014/0244160 A1 | 8/2014 | Cragun et al. |
| 2014/0266755 A1 | 9/2014 | Arensmeier et al. |
| 2014/0267420 A1 | 9/2014 | Schowengerdt et al. |
| 2014/0274151 A1 | 9/2014 | Pattabiraman et al. |
| 2014/0277594 A1 | 9/2014 | Nixon et al. |
| 2014/0278065 A1 | 9/2014 | Ren |
| 2014/0368373 A1 | 12/2014 | Crain et al. |
| 2015/0005903 A1 | 1/2015 | Worek et al. |
| 2015/0094081 A1 | 4/2015 | Gupta |
| 2015/0116132 A1 | 4/2015 | Nohra et al. |
| 2015/0121222 A1 | 4/2015 | Lacaze et al. |
| 2015/0137967 A1 | 5/2015 | Wedig et al. |
| 2015/0154803 A1 | 6/2015 | Meier et al. |
| 2015/0156423 A1 | 6/2015 | Lundberg |
| 2015/0168154 A1 | 6/2015 | Boerger |
| 2015/0177718 A1 | 6/2015 | Vartiainen et al. |
| 2015/0178633 A1 | 6/2015 | ElBsat et al. |
| 2015/0192656 A1 | 7/2015 | Werner et al. |
| 2015/0206348 A1 | 7/2015 | Koreeda et al. |
| 2015/0227123 A1 | 8/2015 | Laycock et al. |
| 2015/0262421 A1 | 9/2015 | Bell et al. |
| 2015/0287318 A1 | 10/2015 | Nair et al. |
| 2015/0294506 A1 | 10/2015 | Bare et al. |
| 2015/0327010 A1 | 11/2015 | Gottschalk et al. |
| 2015/0347854 A1 | 12/2015 | Bare et al. |
| 2015/0356786 A1 | 12/2015 | Bare et al. |
| 2016/0004805 A1 | 1/2016 | Drees et al. |
| 2016/0019721 A1 | 1/2016 | Bare et al. |
| 2016/0026253 A1 | 1/2016 | Bradski et al. |
| 2016/0026729 A1 | 1/2016 | Gil et al. |
| 2016/0048200 A1 | 2/2016 | Kim et al. |
| 2016/0066068 A1 | 3/2016 | Schultz et al. |
| 2016/0071196 A1 | 3/2016 | Joshi et al. |
| 2016/0077532 A1 | 3/2016 | Lagerstedt et al. |
| 2016/0084936 A1 | 3/2016 | Smith et al. |
| 2016/0091217 A1 | 3/2016 | Verberkt et al. |
| 2016/0095188 A1 | 3/2016 | Verberkt et al. |
| 2016/0132046 A1 | 5/2016 | Beoughter et al. |
| 2016/0135006 A1 | 5/2016 | Fjeldsoe-Nielsen |
| 2016/0202678 A1 | 7/2016 | Aggarwal et al. |
| 2016/0216879 A1 | 7/2016 | Park et al. |
| 2016/0258760 A1 | 9/2016 | Beaumont et al. |
| 2016/0284075 A1 | 9/2016 | Phan et al. |
| 2016/0285416 A1 | 9/2016 | Tiwari et al. |
| 2016/0323149 A1 | 11/2016 | Hu et al. |
| 2016/0335731 A1 | 11/2016 | Hall |
| 2016/0343093 A1 | 11/2016 | Riland et al. |
| 2016/0343243 A1 | 11/2016 | Rabb et al. |
| 2016/0345137 A1 | 11/2016 | Ruiz |
| 2016/0356593 A1 | 12/2016 | Huang et al. |
| 2016/0360429 A1 | 12/2016 | Li et al. |
| 2016/0364098 A1* | 12/2016 | Masaki ................... G06F 3/048 |
| 2016/0379083 A1 | 12/2016 | Sala et al. |
| 2017/0006487 A1 | 1/2017 | Baldwin et al. |
| 2017/0055126 A1 | 2/2017 | O'Keeffe |
| 2017/0079001 A1 | 3/2017 | Lewis |
| 2017/0115022 A1 | 4/2017 | Grosshart et al. |
| 2017/0131426 A1 | 5/2017 | Sgarz et al. |
| 2017/0169683 A1 | 6/2017 | Ryder |
| 2017/0200312 A1 | 7/2017 | Smith et al. |
| 2017/0212668 A1 | 7/2017 | Shah et al. |
| 2017/0234962 A1 | 8/2017 | Yang et al. |
| 2017/0235290 A1 | 8/2017 | Weber et al. |
| 2017/0237892 A1 | 8/2017 | Sakai |
| 2017/0286568 A1 | 10/2017 | Dean et al. |
| 2017/0289344 A1 | 10/2017 | Greenberger et al. |
| 2017/0363504 A1 | 12/2017 | Winant et al. |
| 2018/0018826 A1 | 1/2018 | Maier et al. |
| 2018/0031618 A1 | 2/2018 | Friedlander et al. |
| 2018/0075168 A1 | 3/2018 | Tiwari et al. |
| 2018/0084623 A1 | 3/2018 | Joppi et al. |
| 2018/0101803 A1 | 4/2018 | Tiwari et al. |
| 2018/0102858 A1 | 4/2018 | Tiwari et al. |
| 2018/0113506 A1 | 4/2018 | Hall |
| 2018/0130260 A1 | 5/2018 | Schmirler et al. |
| 2018/0131907 A1 | 5/2018 | Schmirler et al. |
| 2018/0159904 A1 | 6/2018 | Hu et al. |
| 2018/0206096 A1 | 7/2018 | Sharma et al. |
| 2018/0242907 A1* | 8/2018 | Bonomi ................... A61B 5/4866 |
| 2018/0285482 A1 | 10/2018 | Santos et al. |
| 2018/0328753 A1 | 11/2018 | Stenning et al. |
| 2018/0357823 A1 | 12/2018 | Koniki et al. |
| 2018/0374269 A1 | 12/2018 | Smith |
| 2019/0025905 A1 | 1/2019 | Godina et al. |
| 2019/0041972 A1 | 2/2019 | Bae |
| 2019/0057169 A1 | 2/2019 | Santarone et al. |
| 2019/0096232 A1 | 3/2019 | Wedig et al. |
| 2019/0145648 A1 | 5/2019 | Sinha et al. |
| 2019/0216333 A1 | 7/2019 | Lai et al. |
| 2019/0228370 A1 | 7/2019 | Lien |
| 2019/0268062 A1 | 8/2019 | Josefiak |
| 2019/0281573 A1 | 9/2019 | Tyagi et al. |
| 2019/0294834 A1 | 9/2019 | Mountz |
| 2019/0355177 A1 | 11/2019 | Manickam et al. |
| 2019/0392088 A1 | 12/2019 | Duff et al. |
| 2019/0392640 A1 | 12/2019 | Qian et al. |
| 2020/0057825 A1 | 2/2020 | Motahar |
| 2020/0108926 A1 | 4/2020 | Smith et al. |
| 2020/0151450 A1 | 5/2020 | Hishinuma et al. |
| 2020/0286300 A1 | 9/2020 | Shih |

FOREIGN PATENT DOCUMENTS

| | | |
|---|---|---|
| GB | 2498177 A | 7/2013 |
| WO | 2008124713 A2 | 10/2008 |
| WO | 2011019810 A1 | 2/2011 |
| WO | 2014204753 A1 | 12/2014 |
| WO | 2016130571 A1 | 8/2016 |

(56) References Cited

FOREIGN PATENT DOCUMENTS

| | | |
|---|---|---|
| WO | 2016192916 A1 | 12/2016 |
| WO | 2017149526 A2 | 9/2017 |
| WO | 2017223008 A1 | 12/2017 |

OTHER PUBLICATIONS

ASCE 2014 Report Card of Montana's Infrastructure, accessed at https://www.infrastructurereportcard.org/wp-contentluploads/2014/11/2014-Report-Card-for-Montanas-Infrastructure.pdf (Year: 2014).

Aukstakalnis, Steve. Practical augmented reality: A guide to the technologies, applications, and human factors for AR and VR. Addison-Wesley Professional, 2016. (Year: 2016).

Azeez et al., "Wireless Indoor Localization Systems and Techniques: Survey and Comparative Study" Indonesian Journal of Electrical Engineering and Computer Science, vol. 3, No. 2, Aug. 2016, pp. 392-409 (Year: 2016).

Brainergiser, "Large holographic projector—a real use case". Sep. 19, 2015, https://www.youtube.com/watch?v=JwnS-EKTW2A&feature=youtu.be.

Carmelo Scuro et al., IoT for Structural Health Monitoring, Dec. 2018, IEEE Instrumentation & Measurement Magazine, pp. 4-14.

Edwards, Luke, "Holograms are finally here: Plasma lasers used to create images in mid-air." Pocket-Lint.com, Nov. 5, 2014, https://www.pocket-lint.com/gadgets/news/131622-holograms-are-finally-here-plasma-lasers-used-to-create-images-in-mid-air.

Gifford, Matthew, "Indoor Positioning with Ultrasonic/Ultrasound", Oct. 19, 2018, 7 pages, https://www.leverege.com/blogpost/ultrasonic-indoor-positioning.

Hexamite, "HX19V2 RFID Ultrasonic Positioning System", 1999, https://www.hexamite.com/hx19.htm.

Hu. Wi-Fi Based Indoor Positioning System Using Smartphones. Nov. 2013. [retrieved on Apr. 23, 2018]. Retrieved [from the Internet: (91 pages total).

International Search Report and Written Opinion dated Feb. 6, 2020 issued in connection with corresponding [International Application No. PCT/US2018/019185 (9 pages total).

International Search Report and Written Opinion dated Feb. 10, 2020 issued in connection with corresponding [International Application No. PCT/US2018/019154 (9 pages total).

International Search Report and Written Opinion dated May 14, 2018 issued in connection with corresponding International Application No. PCT/US2018/019154 (10 pages total).

International Search Report and Written Opinion dated May 7, 2018 issued in connection with corresponding [International Application No. PCT/US2018/019185 (7 pages total).

Khemapech et al., Bridge Structural Monitoring and Warning System Aplication in Thailand—Experiences Learned, 2017, TRON Forum ISBN 978-4-89362-330-0, pp. 1-8.

Kyle, "Property Management" Dearborn Real Estate, 2000—Business & Economics, pp. 40-41.

Liu etal., "A Hybrid Smartphone Indoor Positioning Solution for Mobile LBS" Sensors 2012, issue 12, pp. 17208-17233 (Year: 2012).

Liu, "Survey of Wireless Based Indoor Localization Technologies" accessed at http://www.cse.wustl.edu/-jain/cse574-14/ftp/indoor/index.html, May 5, 2014, 17 pg printout (Year: 2014).

Mordue, Stefan, Paul Swaddle, and David Philp. Building information modeling for dummies. John Wiley & Sons, 2015. (Year: 2015).

Qi, J.; Liu, G.-P. A Robust High-Accuracy Ultrasound Indoor Positioning System Based on a Wireless Sensor Network. Sensors 2017, 17, 2554.

Suermann, Patrick C. Evaluating the impact of building information modeling (BIM) on construction. Florida Univ Gainesvillegraduate School, 2009. (Year: 2009).

Thomson, C. P. H. From Point Cloud to Building Information Model: Capturing and Processing Survey Data Towards Automation forHigh Quality 3D Models to Aid a BIM Process. Diss. UCL (University College London), 2016. (Year: 2016).

Wang et al. Performance Evaluation of Automatically Generated BIM from Laser Scanner Data for Sustainability Analyses. 2015. [retrieved on Apr. 23, 2018]. Retrieved from the Internet:. (8 pages total).

Wang, Siqi, Jinsheng Du, and Jianyong Song. "A Framework of BIM-Based Bridge Health Monitoring System." 2016 InternationalConference on Civil, Transportation and Environment. Atlantis Press, 2016 (Year: 2016).

Wikipedia article "Building Information Modeling", archive data Jan. 15, 2016 on the Wayback machine (Year: 2016).

Yang et ai, "Wi Fi-Based Indoor Positioning", 2015, pp. 150-157 downloaded from the internet I EEE.com databases. (Year: 2015).

Zou et al., "SmartScanner: Know More in Walls with Your Smartphone!" IEEE Transactions on Mobile Computing, vol. 15, No. 11, Nov. 2016, pp. 2865-2877 (Year: 2016).

\* cited by examiner

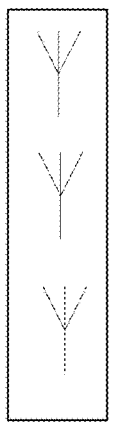
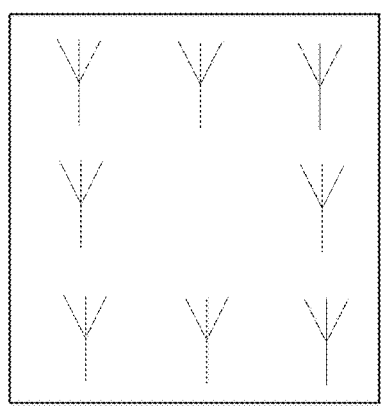
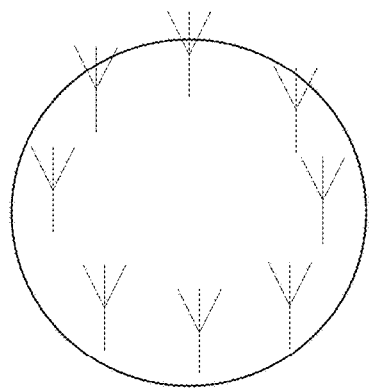
FIG. 4A  FIG. 4B  FIG. 4C
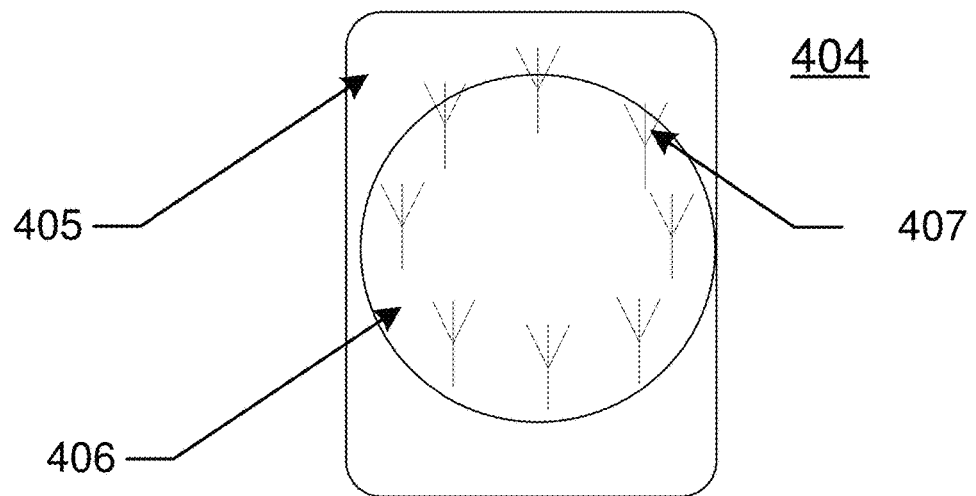
FIG. 4D

```
RECEIVE WIRELESS ENERGY OF A FIRST WAVELENGTH INTO A WIRELESS RECEIVER
                                                                    1001

GENERATE A PATTERN OF DIGITAL VALUES BASED UPON RECEIPT OF WIRELESS
              ENERGY INTO THE WIRELESS RECEIVER
                                                                    1002

OPTIONALLY RECEIVE THE WIRELESS ENERGY FROM THE RECEIVER AS AN ANALOG
                            SIGNAL
                                                                    1003

COORDINATES REPRESENTATIVE OF A WIRELESS NODE MAY BE DETERMINED
                    RELATIVE TO A BASE NODE
                                                                    1004

DETERMINE THE POSITION OF THE BASE NODE RELATIVE TO THE DEFINED PHYSICAL
                              AREA
                                                                    1005

GENERATE A TARGET AREA WITHIN A CONTROLLER OF THE SMART DEVICE
                                                                    1006

RESPECTIVE POSITIONS OF ONE OR MORE WIRELESS NODES WITHIN THE TARGET
                    AREA ARE DETERMINED
                                                                    1007

A USER INTERFACE MAY BE GENERATED ON THE SMART DEVICE BASED UPON THE
       PATTERN OF DIGITAL VALUES GENERATED AT STEP 1002
                                                                    1008

ICON IS GENERATED IN THE USER INTERFACE
                                                                    1009
```

FIG. 10A

TRACKING SAFETY CONDITIONS OF AN AREA

INCORPORATION BY REFERENCE TO RELATED APPLICATIONS

The present application claims priority to Non Provisional patent application Ser. No. 16/935,857, filed Jul. 22, 2020 and entitled TRACKING SAFETY CONDITIONS OF AN AREA, as a continuation application. This application references the Non Provisional U.S. patent application Ser. No. 16/935,857, filed Jul. 22, 2020 and entitled TRACKING SAFETY CONDITIONS OF AN AREA, the entire contents of which are hereby incorporated by reference. This application also references the Non Provisional U.S. patent application Ser. No. 16/504,919, filed Jul. 8, 2019 and entitled METHOD AND APPARATUS FOR POSITION BASED QUERY WITH AUGMENTED REALITY HEADGEAR; and the Non Provisional patent application Ser. No. 16/688,775, filed Nov. 19, 2019 and entitled METHOD AND APPARATUS FOR WIRELESS DETERMINATION OF POSITION AND ORIENTATION OF A SMART DEVICE the entire contents of which are hereby incorporated by reference. This application references the Non Provisional patent application Ser. No. 16/503,878, filed Jul. 5, 2019 and entitled METHOD AND APPARATUS FOR ENHANCED AUTOMATED WIRELESS ORIENTEERING, the entire contents of which are hereby incorporated by reference. This application references the Non Provisional patent application Ser. No. 16/297,383, filed Mar. 8, 2019 and entitled SYSTEM FOR CONDUCTING A SERVICE CALL WITH ORIENTEERING, the entire contents of which are hereby incorporated by reference. This application references the Non Provisional patent application Ser. No. 16/249,574, filed Jan. 16, 2019 and entitled ORIENTEERING SYSTEM FOR RESPONDING TO AN EMERGENCY IN A STRUCTURE, the entire contents of which are hereby incorporated by reference. This application references the Non Provisional patent application Ser. No. 16/176,002, filed Oct. 31, 2018 and entitled SYSTEM FOR CONDUCTING A SERVICE CALL WITH ORIENTEERING, the entire contents of which are hereby incorporated by reference. This application references the Non Provisional patent application Ser. No. 16/171,593, filed Oct. 26, 2018 and entitled SYSTEM FOR HIERARCHICAL ACTIONS BASED UPON MONITORED BUILDING CONDITIONS, the entire contents of which are hereby incorporated by reference. This application references the Non Provisional patent application Ser. No. 16/165,517, filed Oct. 19, 2018 and entitled BUILDING VITAL CONDITIONS MONITORING, the entire contents of which are hereby incorporated by reference. This application references the Non Provisional patent application Ser. No. 16/161,823, filed Oct. 16, 2018 and entitled BUILDING MODEL WITH CAPTURE OF AS BUILT FEATURES AND EXPERIENTIAL DATA, the entire contents of which are hereby incorporated by reference. This application references the Non Provisional patent application Ser. No. 16/142,275, filed Sep. 26, 2018 and entitled METHODS AND APPARATUS FOR ORIENTEERING, the entire contents of which are hereby incorporated by reference. This application references the Non Provisional patent application Ser. No. 15/887,637, filed Feb. 2, 2018 and entitled BUILDING MODEL WITH CAPTURE OF AS BUILT FEATURES AND EXPERIENTIAL DATA, the entire contents of which are hereby incorporated by reference. This application references the Non Provisional patent application Ser. No. 15/716,133, filed Sep. 26, 2017 and entitled BUILDING MODEL WITH VIRTUAL CAPTURE OF AS BUILT FEATURES AND OBJECTIVE PERFORMANCE TRACKING, the entire contents of which are hereby incorporated by reference. This application references the Non Provisional patent application Ser. No. 15/703,310, filed Sep. 13, 2017 and entitled BUILDING MODEL WITH VIRTUAL CAPTURE OF AS BUILT FEATURES AND OBJECTIVE PERFORMANCE TRACKING, the entire contents of which are hereby incorporated by reference. This application references the Non Provisional patent application Ser. No. 16/528,104, filed Jul. 31, 2019 and entitled SMART CONSTRUCTION WITH AUTOMATED DETECTION OF ADVERSE STRUCTURE CONDITIONS AND REMEDIATION, the entire contents of which are hereby incorporated by reference. This application references the Non-Provisional U.S. patent application Ser. No. 16/657,660, filed Oct. 18, 2019 and entitled METHOD AND APPARATUS FOR CONSTRUCTION AND OPERATION OF CONNECTED INFRASTRUCTURE, the entire contents of which are hereby incorporated by reference. This application references the Non-Provisional U.S. patent application Ser. No. 16/721,906, filed Dec. 19, 2019 and entitled METHOD AND APPARATUS FOR WIRELESS DETERMINATION OF POSITION AND ORIENTATION OF A SMART DEVICE, the entire contents of which are hereby incorporated by reference. This application references the Non Provisional patent application Ser. No. 16/549,503, filed Aug. 23, 2019 and entitled METHOD AND APPARATUS FOR AUGMENTED VIRTUAL MODELS AND ORIENTEERING, the entire contents of which are hereby incorporated by reference. This application references the Non Provisional patent application Ser. No. 16/775,223, filed Jan. 28, 2020 and entitled SPATIAL SELF-VERIFYING ARRAY OF NODES, the entire contents of which are hereby incorporated by reference.

FIELD OF THE INVENTION

The present invention relates to automated tracking of safety aspects a person within a defined area. More specifically, the present invention provides for wirelessly tracking a position and condition of a person within a structure or campus. Wireless communications are used to generate positions of a person in three dimensional space and an electronic sensor quantifies physical conditions of the person at respective positions and physical conditions of the environment at those positions. The position and conditions may be periodically determined and recorded for multiple persons such that a controller may determine how often, and for how long, two persons were proximate to each other (if at all) and a biometric condition of each person when in proximity to each other and following such proximity.

BACKGROUND OF THE INVENTION

It has long been recognized that it is valuable to be aware of who is in a defined area such as a building or on a job site. Typically, control has been at an entry point where authorized people are admitted and unauthorized people are prevented from entry. Control over who is allowed in a workplace, for example, provides peace of mind to workers and security for the company assets. Company management and workers have a level of confidence that other persons on a campus are either fellow employees or authorized visitors.

Entry point control provides the confidence that who is on a campus belongs on a campus. It cannot provide further control and assurance that those on campus will only access areas related to their purpose for being on campus, and cannot provide feedback as to behavior during a person's time on the campus.

In addition, in more recent times, it has become important to ascertain not only who is within an area, such as a campus, but whether people in the area pose a health threat to themselves or others while in the area. Even if a person appears healthy at a time of entry, there is no ongoing assessment of the person's health and no record of where a sick person has been, which people they have been in critical contact with, and which equipment they may have infected.

SUMMARY OF THE INVENTION

Accordingly, the present invention combines methods and apparatus for electronically quantifying conditions of a person and an environment containing the person, as well as a sequence of positions occupied by the person and a direction the person faced at those positions. For some contagions, such as COVID-19, a "close contact" has been defined as anyone who was within 6 feet of an infected person for at least 15 minutes starting from 48 hours before the person began feeling sick until the time the patient was isolated (see U.S. Center of Disease Control and Prevention). The present invention provides methods and apparatus to track physiological states of a person to provide empirical quantification of what it means to "feel sick" and also quantify where and when a sick person began to manifest conditions designated as "sick".

The present invention additionally quantifies when a sick person was (and if they were) within a critical distance (e.g. six feet) of a healthy person and a duration of the person being within the critical distance. In some embodiments, the present invention also quantifies whether the sick person was facing the healthy person while they were within a defined critical distance of each other.

In another aspect, data indicates that some environmental conditions, such as high humidity and high temperatures limit the spread of such viral contagions. The present invention can quantify environmental conditions present during the time of the being in "close contact" (or other critical distance) access to quantified environmental conditions may help to determine whether a viral contagion, such as COVID 19, will spread from a sick person to the healthy person.

Data generated by the electronic quantification of conditions may be used to assess a safety risk associated with the person, as well as a safety risk for other persons in proximity to the person. For example, a person with a body temperature quantified to be more than 100° F. may be considered to be running a fever and therefore to be ill. It may be important to be able to assess where the person with an elevated body temperature has been, and when they were at a location, and in which direction they faced (and consequently exhaled, coughed, sneezed etc.). It may also be important to determine which other persons came into close proximity with the ill person and for how long, and whether the other person was in front of the ill person, or back to back with them.

The present invention provides methods and apparatus for deploying electronic sensors to quantify conditions in a defined area, including conditions that quantify physiological states of human beings (or other mammals), In addition, the present invention provides for generating a user interface with content based upon a geospatial location of a user and a direction of interest provided by the user. Essentially, based upon who a user is, where the user is, and which direction an area indicated by the user is oriented, the present invention provides an interactive user interface that combines a quantification of a condition within with area indicated and digital content.

The present invention additionally provides for generation of data useful in quantifying which conditions are most conducive to transfer of a contagion from a sick person to a healthy person. Such data is generated during the normal course of operation of a facility and tracking of physiological data of persons in the facility, conditions within the facility and position tracking and dwell time of a first person within a designated distance to a second person.

Other aspects of the present invention include an augmented reality interface that allows a user to direct a Smart Device towards an area, and have an image of the presented in a virtual environment that combines a rendition of the physical environment with digital content descriptive of persons and conditions in the environment. For example, by holding up a smart device, a user may be presented with a video type image showing a scene in front of the smart device and have one or more persons in the scene identified. In addition, values for biometrics (e.g. a physiological condition such as body temperature) for the person may be displayed. As the person moves about within the scene, a link (icon or other user interactive device) to information about the person will follow the person in the scene on the smart device. The user need only select the link to cause the smart device to display more detailed information about the person selected.

The present invention uses electronic sensors to quantify conditions present with the person and an environment in which the person is encompassed. Transceivers are co-located with the sensors and wireless communications are used to determine a location of the person based upon the transceiver location. Based upon values of a wireless communication completed by the Node, positional coordinates are generated indicating where the sensor is located. The sensor is operative to quantify a condition at a location monitored by the sensor. When a Smart Device is used to view a physical area containing the Node and the sensor, the Smart Device is operative to display a rendition of the area with the Node location and the conditions measured by the sensor.

Essentially, the present invention enables point and query (or ask and query) access to information or other content in an area chosen via a Smart Device, including, for example content about a person wearing a positional tag and biometric sensor. The Smart Device may be used to generate an interface indicating which people, equipment, vehicles or other items are viewable to the Smart Device and place those items into the context of the environment surrounding the Smart Device. The interface will also indicate a quantification of the environment.

According to the present invention such functionality may be accomplished by establishing a target area and determining which tags are present within the target area. Tags may be virtual or physical. Virtual tags are associated with positional coordinates and viewable whenever a target area is designated to encompass the coordinates the virtual tag. Physical tags include a processor and a transceiver capable of wireless communication. Tracking of a position and content associated a physical tag may be updated in real time or on a periodic basis. Physical tags may be moved into a target area or the target area may be moved to encompass the physical tag. The present invention will automatically generate an interface indicating which tags are contained within an area portrayed by the interface, as well as which persons and sensors are associated with a tags. Additionally, the interface may indicate where a tag is in relation to the Smart Device. The interface may also access digital content that has been stored and associated with the tag and present it in the interface.

By aligning real world and virtual world content, a real world site experience is enriched with content from a geospatially linked virtual world. The virtual world content is made available to an Agent based upon a position and a direction of a Radio Target Area ("RTA") specified by a Smart Device supported by the Agent. A geospatial position and direction of interest that is contained within the RTA is generated using wireless communication with reference point transmitters. Wireless communication capabilities of the Reference Point Transmitters determine parameters associated with a Wireless Communication Area ("WCA"). The RTA is a subset of the WCA.

The present invention provides for methods and apparatus for executing methods that augment a physical area, such as an area designate as a wireless communication area. The method may include the steps of transceiving a wireless communication between a Smart Device and multiple reference point transceivers fixedly located at a position within a wireless communication area; generating positional coordinates for the Smart Device based upon the wireless communication between the Smart Device and the multiple reference transceivers; establishing a radio target area for an energy receiving sensor; receiving energy into the energy receiving sensor from the radio target area; generating a digital representation of the energy received into the energy receiving sensor at an instance in time; generating positional coordinates for a tag at the instance in time, the tag comprising digital content and access rights to the digital content; determining the tag is located within the radio target area based upon the positional coordinates for the tag; generating a user interactive interface comprising static portions based upon the digital representation of the energy received into the energy receiving sensor; generating a dynamic portion of the user interactive interface based upon the positional coordinates for the tag and the positional coordinates for the Smart Device; receiving a user input into the dynamic portion of the user interactive interface; and based upon the user input received into the dynamic portion of the user interactive interface, including the digital content in the user interactive interface.

In some embodiments, multiple disparate energy levels may be received into the energy receiving sensor at the instance in time, each disparate energy level received from a different geospatial location; associating positional coordinates with the disparate energy levels; and indicating the disparate energy levels and relative positions of the disparate energy levels in the user interactive interface. A tag may include a virtual tag with the digital content and a location identified via positional coordinates.

In another aspect, a physical tag may include a transceiver capable of wireless communication with the multiple reference transceivers and the method may include transceiving a wireless communication between a tag and multiple reference point transceivers; and generating positional coordinates for the tag based upon the wireless communication between the tag and the multiple reference transceivers. The wireless communication between the Smart Device and the multiple reference point transceivers may be accomplished by transceiving using an Ultra-Wideband modality; Bluetooth modality or other wireless modality, such as WiFi.

A wireless communication area may be identified as including a radio transmission area of the energy receiving sensor and the wireless communication area may be based upon a communication distance of the Ultra-Wideband modality in an area encompassing the energy receiving sensor.

Transceiving a wireless communication between a tag and multiple reference point transceivers may be accomplished using w wireless modality such as, for example, a UWB or Bluetooth modality; and generating positional coordinates for the tag based upon the wireless communication between the tag and the multiple reference transceivers may be accomplished using the same modalities. Positional coordinates may include one or more of: Cartesian Coordinates, an angle of arrival and an angle of departure and a distance.

In another aspect, access rights to tag content may be required and based upon an identifier of the Smart Device or a user operating the Smart Device. A dynamic portion of the user interactive interface may include an icon indicative of the digital content associated with the tag.

The details of one or more examples of the invention are set forth in the accompanying drawings and the description below. The accompanying drawings that are incorporated in and constitute a part of this specification illustrate several examples of the invention and, together with the description, serve to explain the principles of the invention: other features, objects, and advantages of the invention will be apparent from the description, drawings, and claims herein.

DESCRIPTION OF THE DRAWINGS

The accompanying drawings, that are incorporated in and constitute a part of this specification, illustrate several embodiments of the invention and, together with the description, serve to explain the principles of the invention:

FIGS. 4A-4D illustrate exemplary configurations of antenna arrays.

FIGS. 10A-10B illustrates an exemplary method for generating an augmented-reality Radio Target Area for a Smart Device.

DETAILED DESCRIPTION

Figure 1:
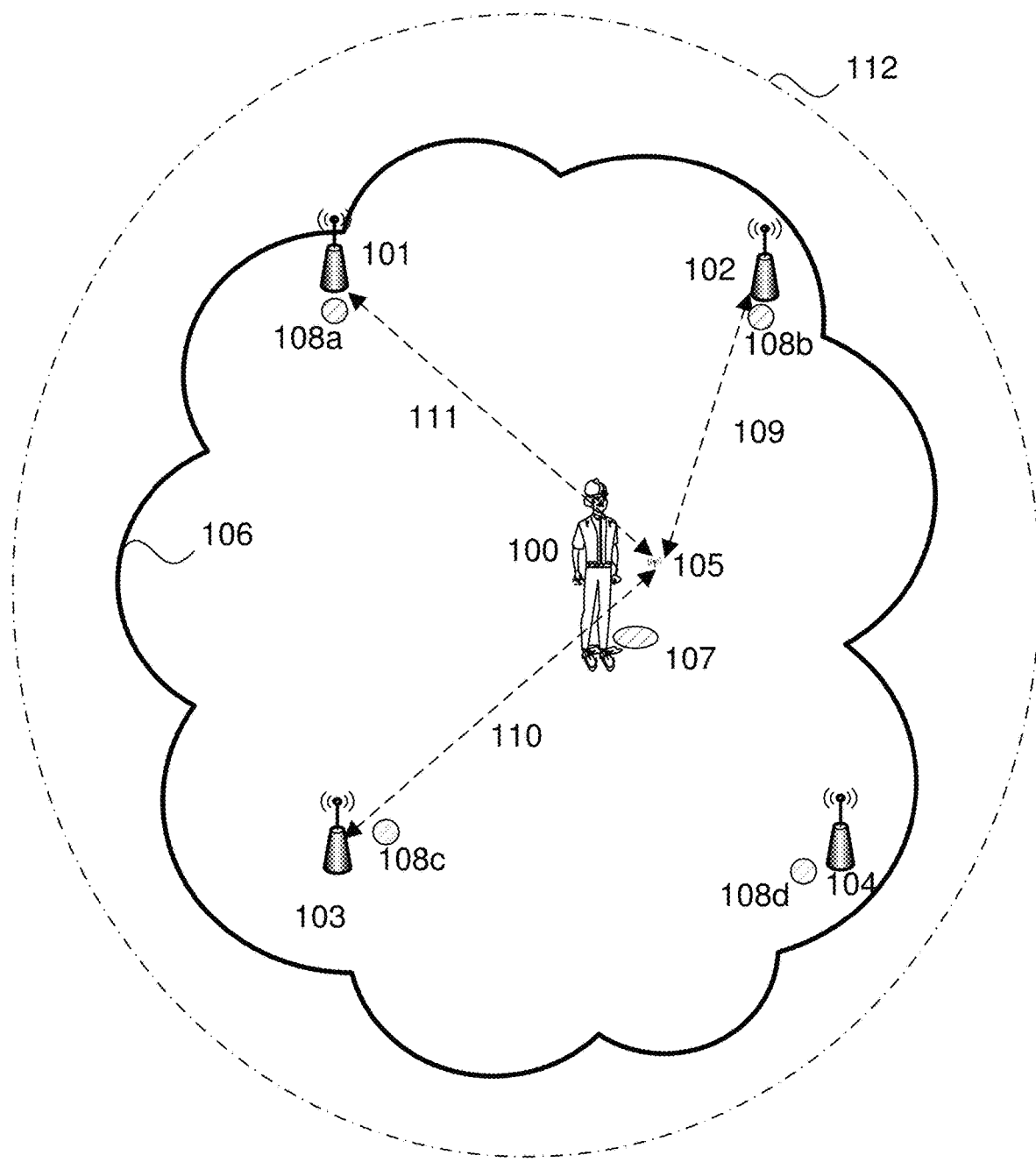
FIG. 1 illustrates location determination with wireless communication to reference points.

The present invention provides a safety system with methods and apparatus for tracking a position and orientation of person(s) within a defined area as well as physiological measurements (sometimes referred to herein as "biometrics") of the person. The physiological measurements may be used to infer a relative health of the person, and whether the person represents a health hazard to other persons that are within a distance deemed to impart adverse health conditions.

In some embodiments, a path (multiple positions at specific time intervals) traversed by the person tracked may be recreated and compared to positions of other persons and/or items. For example, if a first person, Ms. Smith is being tracked, the present invention will determine if a path Ms. Smith traveled coincided with a path traveled by Mr. Jones, and also whether Ms. Smith and Mr. Jones faced each other while they were within a threshold distance. A sensor may be used to quantify a physiological condition of one or both of Ms. Smith and Mr. Jones in order to assess whether Ms. Smith posed a health risk to Mr. Jones. Health risk may include, for example, a likelihood of transferring a biological conveyor of disease (e.g. a virus and/or bacteria) from Ms. Smith to Mr. Jones.

Similarly, if Ms. Smith came within a threshold distance to an item, such as a piece of equipment or an architectural aspect of a building (such as a door), the present invention may provide an indication of whether the item has a significant probability of being contaminated with a biological conveyer of disease on its surface.

In some embodiments, a user interface is generated that determines the existence of real world aspects, such as the presence of a person with an elevated body temperature and aligned virtual-world content, such as an icon that moves about with the person in the interface and links out to digital content associated with the person.

In the following sections, detailed descriptions of examples and methods of the invention will be given. The description of both preferred and alternative examples though thorough are exemplary only, and it is understood that, to those skilled in the art, variations, modifications and alterations may be apparent. It is therefore to be understood that the examples do not limit the broadness of the aspects of the underlying invention as defined by the claims.

In some examples, a reference point Node may be placed in a fixed location and function as a transceiver of signals. For example, a Node may receive and transmit signals in a radio frequency band of the electromagnetic spectrum. In a simple form, a Node may receive an incoming wireless radio frequency communication and also broadcast a radio frequency wireless communication. Radio frequencies utilized for wireless communication may include those within the electromagnetic spectrum radio frequencies used in UWB, Wi-Fi, and Bluetooth modalities, as well as IR, bisible and UV light as examples.

In some embodiments, a Node is operative to communicate timing data and data generated by a sensor. Such communications may provide identifying information unique to the Node, data related to the synchronization of timing with reference point transceivers, and/or data received from other Nodes.

A triangulation calculation of the position of a Smart Device or a Node may result from a system of multiple reference position Nodes communicating timing signals to or from the Smart Device or Node. Methods of calculating positions via wireless communications may include one or more of: RTT, RSSI, AoD, AoA, timing signal differential and the like. Triangulation or other mathematical techniques may also be employed in determining a location.

The process of determination of a position based upon triangulation with the reference points may be accomplished, for example via executable software interacting with a controller in a Node, a Smart Device, or server.

Referring now to FIG. 1, components are illustrated that may be included in a system that is capable of wireless position and orientation according to the present invention. Reference Point Transceivers 101-104 are shown positioned within or proximate to a defined area 106. Wireless communications between the Reference Point Transceivers and one or more Transceivers 105 supported by an Agent 100 include timing data or other information useful to determine a location 107 of the Transceiver 105 supported by the Agent 100, within or proximate to the defined area 106.

Positions of the Reference Point Transceivers 101-104, which are fixed in respective locations 108 within or proximate to the defined area 106, define a wireless communication area (WCA) 112. Essentially the WCA 112 defines an area in which a location of a person may be tracked. A sensor may continue to quantify a physiological state of the person supporting an appropriate sensor whether or not the person is within the WCA 112.

In some embodiments, data quantifying a physiological state of a person may be stored within a Node or Tag supported by the person and transmitted via wireless communication once a Node or Tag is within wireless communication range of a Reference Point Transceiver 101-104.

The Reference Point Transceivers 101-104 transceive information capable of being used to determine a position of the one or more Transceivers 105 supported by an Agent 100, such as, for example, a Transceiver 105 in or associated with a Smart Device, headgear or Tag supported by the Agent 100. Transceiving may be conducted via one or more wireless transmission modalities between the Transceiver 105 supported by the Agent 100 and the Reference Point Transceivers 101-104.

By way of non-limiting example, Transceivers 105 supported by the Agent 100 may be included in, and/or be in logical communication with, a Smart Device, such as a smart phone, tablet, headgear, ring, arm band, watch, footwear, vest, lab coat, smock, wand, pointer, badge, Tag, Node or other Agent 100 supportable device with a portable Transceiver 105 able to transceive with the Reference Point Transceivers 101-104.

The Reference Point Transceivers 101-104 may include devices capable of wireless communication via a same modality as that utilized by the Agent-supported Transceiver 105. A radio frequency transceiver included in one or both of the Reference Point Transceivers 101-104 and the Agent-supported Transceiver 105 may therefore transmitters and receivers operative to communicate via wireless modalities that include, for example: Wi-Fi, Bluetooth, Ultra-wideband ("UWB"), ultrasonic, infrared, or other communication modality capable of logical communication between Transceivers 101-105.

In some embodiments, a Reference Point Transceiver 101-104 may include a multi-modality transceiver, that communicates more locally via a first modality, such as Ultrawideband ("UWB"), Bluetooth, Wi-Fi, ANT, Zigbee, BLE, Z Wave, 6LoWPAN, Thread, Wi-Fi, Wi-Fi-ah, NFC (near field communications), Dash 7, Wireless HART or similar modality; and to a greater distance via a second modality, such as a cellular communication modality (e.g. 3G, 4G, 5G and the like), sub GHz modality, Internet Protocol modalities and the like which may provide access to a distributed network, such as the Internet. Other modalities are also within the scope for the present invention.

Wireless communications between Transceivers 101-105 may engage in logical communications to provide data capable of generating one or more of: Cartesian coordinates, polar coordinates, vector values, AoA, AoD, RTT, RSS, a GPS position, or other data that may be utilized for one or more of: locating one or both of an Agent 100; indicating a direction of interest; and identify a defined area 106.

A precise location may be determined via logical processes, such as triangulation; trilateration; and/or angle phase change; based upon timing values or other mechanism to generate a distance from one or more antennas in the multiple Reference Point Transceivers 101-104 to one or more antennas in an Agent-supported Transceiver (s) 105.

For example, a radio transmission or light transmission be measured and compared from three Reference Point Transceivers 101-103. Measurement may include, one more of: a timing value, a received transmission strength, received transmission amplitude, and received transmission quality.

Other embodiments may include a device recognizable via image analysis via a sensor, LiDAR, Image Capture Device, CCD device, and the like which may capture an image of three or more recognizable features. Image analysis may identify three or more of the recognizable features and a size ratio of the respective image captured recognizable features may be utilized to calculate a distance from each and thereby a position of the Agent 100. Similarly, a height designation may be made via triangulation using the position identifiers as reference to a known height or a reference height.

Transceivers 101-105 may include circuitry, antenna(s) and logic capable of transceiving in a single modality, or multiple disparate modalities. Similarly, a Reference Point Transceiver 101-104 and/or an Agent-supported Transceiver 105 may include multiple transceiver devices, including, antennas, transmitters and receivers.

A modality, as used in conjunction with a Transceiver, transmitter and/or receiver refers to one or both of a bandwidth of wireless communication and a protocol associated with a bandwidth. By way of non-limiting example, a modality, as used in relation to a Transceiver, transmitter and/or receiver may include: Wi-Fi; Wi-Fi RTT; Bluetooth; UWB; Ultrasonic, sonic, infrared; ANT, Zigbee, BLE, Z Wave, 6LoWPAN, Thread, Wi-Fi, Wi-Fi 33-ah, NFC (near field communications), sub-GHz, Dash 7, Wireless HART or other logical communication medium.

Triangulation generally includes determining an intersection of three distances 109-111, each distance 109-111 calculated from a Reference Point Transceiver 101-104 to an Agent-supported Transceiver 105. The presence invention allows for a first distance 109, to be determined based upon a wireless communication in a first modality; and a second distance 110 and a third distance 111 determined based upon a wireless communication in a same or different modality as the first modality. For example, a first distance 109 may be determined based upon a wireless communication using UWB; a second distance 110 may be determined based upon a wireless communication using Bluetooth; and a third communication may be determined based upon a wireless communication using ultrasonic communication (other combinations of same and/or different communication modalities are also within the scope of the present invention).

A location 107 may be determined via triangulation based upon a measured distance from three or more position identifiers 101-103 to the Agent-supported Transceiver 105. For example, timing associated with a radio transmission or light signal may be measured and compared from the three Reference Point Transceivers 101-103. Other embodiments may include a device recognizable via image analysis and a sensor or other Image Capture Device, such as a CCD device, may capture an image of three or more Reference Point Transceivers 101-104.

Additional embodiments may include image analysis of image data captured via a CCD included in a Smart Device to recognize the identification of each of three or more of Reference Point Transceivers 101-104 and a size ratio of the respective image captured Reference Point Transceivers 101-104 may be utilized to calculate a precise position. Similarly, a height designation may be made via triangulation using the position identifiers as reference to a known height or a reference height. In a similar fashion, triangulation may be utilized to determine a relative elevation of the Smart Device as compared to a reference elevation of the reference points.

In some embodiments, the location 107 of the Agent-supported Transceiver 105 may be ascertained via one or more of: triangulation; trilateration; and multilateration (MLT) techniques.

In some embodiments, a geospatial location based upon triangulation may be generated based upon a controller receiving a measurement of angles between the position and known points at either end of a fixed baseline. By way of non-limiting example, a point of a geospatial location may be determined based upon generation of a triangle with one known side and two known angles. Moreover, a geospatial location based upon multilateration may be generated based on a controller receiving measurement of a difference in distance to two reference positions, each reference position being associated with a known location. Wireless signals may be available at one or more of: periodically, within determined timespans and continually. The determination of the difference in distance between two reference positions provides multiple potential locations at the determined distance. A controller may be used to generate a plot of potential locations. In some embodiments, the potential determinations generally form a curve. Specific embodiments will generate a hyperbolic curve.

The controller may be programmed to execute code to locate a relatively exact position along a generated curve, which is used to generate a geospatial location. The multilateration system thereby receives as input multiple measurements of distance to reference points, wherein a second measurement taken to a second set of stations (which may include one station of a first set of stations) is used to generate a second curve. A point of intersection of the first curve and the second curve may be used to indicate a specific location.

Other methodologies within the scope of the present invention include trilateration, which may treat the positions of the Reference Point Transceivers as vertices of one or more triangles and/or phased array antennas which indicate a direction of a wireless communication.

In another aspect, in some embodiments, the location of a Transceiver 101-105 may be determined and/or aided in location determination via discernment of data based upon a physical artifact or patterns of artifacts, such as, for example a visually discernable feature, shape or printed aspect located within the defined area 106. Discernment of the physical artifact may, for example, be based upon topographical renditions of physical aspects included in the Structure, such as those measured using LIDAR, a magnetic force, image data (or a point cloud derived from image data). A pattern on a surface may convey a reference point by a recognizable pattern (which may be unique to the setting), Vernier or three-dimensional structure as non-limiting examples. A Smart Device ascertaining a physical reference mark and a distance of the Smart Device to the mark may determine a relative location in space to a coordinate system of the marks.

Marks tied to a geospatial coordinate system may be utilized to determine a relative location based upon a distance to the mark(s). A number of methods may be executed to determine a distance from the Smart Device to a mark such as, for example, a sense reflection of light beams (preferably laser beams), electromagnetic beams of wavelength outside of the visible band such as IR, UV, Radio and the like, or sound-based emanations. Method steps may be implemented by executing software code with a processor.

In some examples, a Node may function as a Reference Point Transceiver 101-104. For example, a Node may receive and transmit signals in a radio frequency band of the electromagnetic spectrum. In a simple form, a Node may detect an incoming signal and coincidently broadcast a radio frequency wireless communication. Frequencies utilized for wireless communication may include those within the electromagnetic spectrum radio frequencies used in UWB, Wi-Fi, and Bluetooth modalities, as well as IR, Visible and UV light as examples.

In some embodiments, sound emanations may also be used as a communication mechanism between a smart device and a Reference Point Transceiver 101-104. In some examples, the Reference Point Transceiver 101-104 may function to communicate data with their electromagnetic or sonic transmissions. Such communications may provide identifying information unique to the Node, data related to the synchronization of timing at different well located reference points, and may also function as general data communication nodes. A triangulation calculation of the position of a Smart Device or a Node may result from a system of multiple reference position Nodes communicating timing signals to or from the Smart Device or Node. Methods of calculating positions via wireless communications may include one or more of: RTT, RSSI, AoD, AoA, timing signal differential and the like, Triangulation or other mathematical techniques may also be employed in determining a location.

The process of determination of a position based upon triangulation with the reference points may be accomplished, for example via executable software interacting with the controller, such as, for example via running an app on the Smart Device or executing software on a server.

In some embodiments, reference points may be individually identified via identifiers, such as a UUID (Universally Unique Identifier), or other identification vehicle.

Reference Position Transceivers 101-104 may be deployed in a wireless defined area 106, such as an interior to a building or other structure or infrastructure, to determine a location 107 of an Agent 100 within or proximate to the wireless defined area 106.

In some embodiments, Reference Position Transceivers 101-104 are generally fixed in a location within the wireless defined area 106. In other embodiments, the Reference Point Transceivers 101-104 may change locations, in these embodiments, a position of the Agent-supported Transceiver 105 will be determined relative to the Reference Point Transceivers 101-104, but not necessarily to structure in which the Reference Point Transceivers 101-104 and Agent-supported Transceiver 105 are located.

The Reference Point Transceivers 101-104 and the Agent-supported Transceiver 105 will transceive in a manner suitable for a triangulation determination of a location 107 of the Agent 100. Transceiving may occur via wireless transmission to one or more Agent-supported Transceiver 105. By way of non-limiting example, Agent-supported Transceiver 105 may be included in, or be in logical communication with, a Smart Device supported by the Agent 100 and be able to transceive with the Reference Position Transceivers 101-104.

The Reference Position Transceivers 101-104 may include devices such as a radio transmitter, radio receiver, a light generator, or an image-recognizable device (i.e., an apparatus set out in a distinctive pattern recognizable by a sensor). A radio transmitter may include a UWB Node, Wi-Fi, Bluetooth or other wireless communication transceiver for entering into logical communication between Transceivers 101-105. In some embodiments, Reference Point Transceivers 101-104 may include a Wi-Fi router, UWB router or other multi-modality device that additionally provides access to a distributed network, such as the Internet.

Cartesian coordinates (including Cartesian coordinates generated relative to a GPS or other reference point), or any other coordinate system, may be used as data that may be utilized for one or more of: locating one or both of an Agent 100; indicating a direction of interest; and identifying a defined area 106. A radio transmitter may include a router or other Wi-Fi device. The radio transmitter may include transmissions via a Ultra-Wideband ("UWB") frequencies including, for example, frequencies above 500 MHz, 3.5-6.5 GHz or other frequencies usable with a UWB modality; on Wi-Fi frequencies (300 MHz-60 GHz), sub GHz frequencies or other modality. A light generator may distribute light at human-safe intensities and at virtually any frequency known in the art. Such frequencies may include, without limitation: infrared, ultraviolet, visible, or nonvisible light. Further, a light beacon may comprise a laser, which may transmit light at any of the aforementioned frequencies in a coherent beam.

This plurality of modalities allows for increased accuracy because each modality may have a different degree of reliability. For example, a Smart Device and/or Smart Receptacle may measure a timing signal transmitted by a Reference Point Transceiver 101-104 within a different error tolerance than it may measure the receipt into a photodetector of infrared laser light.

In another, aspect, multiple timing signals that have been wirelessly communicated may be mathematically processed to increase an overall accuracy, such as, for example, combined into a weighted average, average, mean, weighted mean. In situations with multiple timing signals communicated via different modalities a weighted average may be determined to be most beneficial. In some embodiments, conditions in an environment through which the wireless communication of values for variables enabling determination of a location of a Transceiver 105 may be quantified by sensors and the quantified conditions may be used to further ascertain a beneficial mathematical process. For example, if sensors indicate significant electrical interference in a particular bandwidth of the electromagnetic spectrum, such as a spectrum utilized by UWB and/or Bluetooth modalities, a mathematical process may give a higher weight to a value (for a variable useful in determining the position of a Transceiver 105) transmitted via an infrared modality which is not effected by the electrical interference. Likewise, if a sensor reading quantifies a significant amount of particulate or other interference in an atmosphere through which a wireless communication is transmitted, a lower mathematical weight may be allocated to an infrared transmission (or other light beam effected by particulate) value.

Also, processing may allow for outliers of values for variables useful in determining a location to be shed. For example, if a standard location calculation comprises a weighted average of multiple values for variable useful for determining a location, which may include values generated based upon wireless communication using multiple modalities, but a particular modality yields a location greater than two standard deviations from an average computed location, then that modality may not be considered a recalculation and/or in future weighted location calculations. Similarly, values generated using a single modality that fall outside a designated deviation (e.g. two standard deviations or three standard deviations) may be excluded from a value generated via mathematical processing (e.g. average, weighted average, mean, median, mode, etc.).

Additionally, the radio transmitters, receivers, and/or transceivers in a Tag, Node and/or Smart Device may include multiple antennas that transmit and/or receive electromagnetic transmissions. In some embodiments, the multiple antennas may transmit and/or receive in a staggered fashion suitable to reduce noise.

By way of non-limiting example, if a Tag, Node and/or Smart Device uses three antennas that are operative to transmit a signal in intervals of 20 milliseconds from a same or disparate selection of antenna(s). A detected time of arrival at a receiving antenna may be used to determine a distance between a transmitting transceiver and a receiving antenna. In some embodiments, various antennas may be of varying lengths to better accommodate chosen wavelengths or wireless communication.

A precise location may be determined based upon wireless transmissions between Nodes, such as between an Agent-supported Transceiver 105 and one or more Reference Point Transceivers 101-104. Timing determinations—as well as signal qualities like angle of arrival, angle of departure, transmission strength, transmission noise, and transmission interruptions—may be considered in generating relative positions of the Tag.

Additional considerations may include AI and unstructured queries of transmissions between Tags and triangulation logic based upon a measured distance from three or more Reference Point Transceivers 101-104. For example, a radio transmission or light emission may be measured, and timing associated with the radio transmission or light emission to determine a distance between disparate transceivers included in Tags, Nodes, Smart Devices and the like. Distances from three Reference Point Transceivers 101-103 may be used to generate a position of a Transceiver in consideration. Other methodologies include determination of a distance from one or more Transceiver and a respective angle of arrival and/or angle of departure of a radio or light transmission between the Node in consideration and another Transceiver (Reference Point Transceiver or dynamic position Transceiver, e.g. an Agent supported Tag or Node).

In some embodiments of the present invention, position determination in a Structure or on a Property contemplates determination of a geospatial location using triangulation, trilateration, or multilateration techniques. A geospatial location relative to one or more known reference points is generated based upon wireless communications between multiple Transceivers 101-105. The geospatial location in space may be referred to as having a position described with coordinates. Various coordinates may include Cartesian Coordinates, Polar Coordinates, Cylindrical Coordinates and the like. Cartesian Coordinates include an X,Y position indicating a planar designation (e.g. a position on a flat floor), and a Z position (e.g. a level within a Structure, such as a second floor). The coordinates may be generated based upon indicators of distance from reference points. Indicators of distance may include a comparison of timing signals received from wireless references. A geospatial location may be generated relative to the reference points. In some embodiments, a geospatial location with reference to a larger geographic area is associated with the reference points, however, in many embodiments, a controller will generate a geospatial location relative to the reference point(s) and it is not relevant where the position is located in relation to a greater geospatial area. In addition to these Cartesian coordinates, polar coordinates may be used, as further described below.

A geospatial location based upon triangulation may be generated based upon a controller receiving a measurement of angles between the position and known points at either end of a fixed baseline. A point of a geospatial location may be determined based upon generation of a triangle with one known side and two known angles.

Referring now again to FIG. 1, triangulation essentially includes determining an intersection of three distances 109-111, each distance 109-111 calculated from a Reference Point Transceivers 101-104 to an Agent-supported Transceiver 105. The present invention allows for a first distance 109 to be determined based upon a wireless communication in a first modality; and a second distance 110 and a third distance 111 determined based upon a wireless communication in a same or different modality as the first modality. For example, a first distance 109 may be determined based upon a wireless communication using UWB; a second distance 110 may be determined based upon a wireless communication using Bluetooth; and a third communication may be determined based upon a wireless communication using ultrasonic communication (other combinations of same and/or different communication modalities are also within the scope of the present invention).

A geospatial location based upon trilateration may be generated with a controller receiving indicators of distance based upon wireless communication of values for variables, such as timing values, that may be processed to ascertain geometry of shapes, such as circles, spheres, triangles and the like.

Similarly, a geospatial location based upon multilateration may be generated based on a controller receiving a measurement of a difference in distance to two reference positions, each reference position being associated with a known location. Wireless signals may be available at one or more of: periodically, within determined timespans, and continually. The determination of the difference in distance between two reference positions provides multiple potential locations at the determined distance. A controller (such as one in the Smart Device) may be used to generate a plot of potential locations. In some embodiments, the potential determinations generally form a curve. Specific embodiments will generate a hyperbolic curve.

The controller may be programmed to execute code to locate an exact position along a generated curve, which is used to generate a geospatial location. The multilateration thereby receives as input multiple measurements of distance to reference points, wherein a second measurement taken to a second set of stations (which may include one station of a first set of stations) is used to generate a second curve. A point of intersection of the first curve and the second curve is used to indicate a specific location.

In exemplary embodiments, as described herein, the distances may be triangulated based on measurements of UWB, Wi-Fi or sub GHz strength at two points. Transceiver signals propagate outward as a wave, ideally according to an inverse square law. Ultimately, a crucial feature of the present invention relies on measuring relative distances between two points. In light of the speed of Wi-Fi waves and the real-time computations involved in orienteering; these computations need to be as computationally simple as possible. Thus, depending upon a specific application and mechanism for quantifying a condition or location, such as a measurement, various coordinate systems may be desirable. In particular, if the Smart Device moves only in a planar direction while the elevation is constant, or only at an angle relative to the ground, the computation less complicated.

One exemplary coordinate system includes a polar coordinate system. One example of a three-dimensional polar coordinate system is a spherical coordinate system. A spherical coordinate system typically comprises three coordinates: a radial coordinate, a polar angle, and an azimuthal angle (r, $\theta$, and $\varphi$, respectively, though $\theta$ and $\varphi$ are occasionally swapped conventionally).

By way of non-limiting example, suppose Point 1 is considered the origin for a spherical coordinate system (i.e., the point (0, 0, 0)). Each Transceiver 101-105 emitter $e_1$, $e_2$, $e_3$ can be described as points $(r_1, \theta_1, \varphi_1)$, $(r_2, \theta_2, \varphi_2)$, and $(r_3, \theta_3, \varphi_3)$, respectively. Each of the $r_i$'s ($1 \leq i \leq 3$) represent the distance between the Transceiver 101-105 emitter and the Transceiver 101-105 receiver on the Smart Device 101 or Smart Receptacle (see FIG. 5A).

It is understood that in some embodiments, an azimuth may include an angle, such as a horizontal angle determined in an arcuate manner from a reference plane or other base direction line, such as an angle formed between a reference point or reference direction; and line (ray or vector) such as a ray or vector generated from or continuing to a Smart Device. In preferred embodiments, the ray or vector may be generally directed from a Reference Position Transceiver towards, and/or intersect one or more of: an item of interest; a point of interest; an architectural aspect (such as a wall, beam, header, corner, arch, doorway, window, etc.); an installed component that may act as a reference in an augmented virtual model (AVM) (such as, for example, an electrical outlet, a light fixture, a plumbing fixture, an architectural aspect; an item of equipment; an appliance; a multimedia device, etc.); another Reference Position Transceiver or other identifiable destination.

Accordingly, in some embodiments, a spherical coordinate system may include Reference Position Transceiver that is capable of determining an angle of departure of a location signal and a Transceiver that is capable of determining an angle of arrival of the location signal; one or both of which may be used to facilitate determination of an applicable azimuth.

According to various embodiments of the present invention, one or both of an angle of departure and an angle of arrival may therefore be registered by a Transceiver that is transmitting and/or receiving wireless signals (e.g. radio frequency, UWB, Bluetooth 5.1, sonic frequency, or light frequency).

In some embodiments, locating an Agent 100 occurs in or proximate to a Structure in which Reference Position Transceivers, (including, for example, one or more of: Wi-Fi Transceivers, UWB Transceivers, Bluetooth Transceivers, infrared Transceivers and ultrasonic Transceivers) may be located above and/or below an Agent 100. In these embodiments, a cylindrical coordinate system may be more appropriate. A cylindrical coordinate system typically comprises three coordinates: a radial coordinate, an angular coordinate, and an elevation (r, $\theta$, and z, respectively). A cylindrical coordinate system may be desirable where, for example, all Wi-Fi emitters have the same elevation. Angles may be determined as described above.

In some embodiments, Transceivers 101-105 including arrays of antennas may be used to measure an angle of radio communication (e.g. angle of arrival and/or angle of departure). Various configurations of transmitting antennas and receiving antennas may be used. For example, a radio transmission may be transmitted with a single antenna and received with a receiver with an array of antennas, the phase or timing difference of arriving signals can be used to calculate the angle at which the signals emerged. In angle of departure schemes, a transmitter may contain an array of antennas and may send a pattern of signals through the array that arrive at a receiver with a single antenna where the angle of departure (AoD) is communicated.

Measurement of angle of arrival may be performed as mentioned by calculation of time difference of arrival at the antennas in an array or alternatively can be performed by rotation of antenna elements.

Some modalities, such as those modalities that adhere to the Bluetooth 5.1 or BLE5.1 standards, allow a Smart Device 101, Smart Receptacle or other Node to determine an angle of arrival (AoA) or an angle of departure (AoD) for a wireless transmission. An array of antennas may be used to measure aspects of the Bluetooth signaling that may be useful to calculate these AoA and AoD parameters. By calibrating an antenna system, the system may be used to determine angles in one or two dimensions depending on the design of the antenna. The result may be significant improvement in pinpointing the location of origin of a signal.

An array of antennas may be positioned relative to each other and a transmitting transceiver to allow for extraction of an AoA/AoD. Such an array may include a rectangular array; a polar or circular array; a linear array; and a patterned array, where a number of antennas are deployed in a pattern conducive to a particular environment for transceiving. Antennas may be separated by characterized distances from each other, and in some examples, a training protocol for the antenna array results in antenna positioning incorporating superior angle and location precision. Some transceivers may transceive in 2.4-2.482 GHz frequency bands, and thus the radiofrequency transmissions may have wavelengths in the roughly 125 mm length scale. A collection of antennas separated by significantly less than the wavelength may function by comparing a phase of RF transmissions arriving at the antennas. An accurate extraction of phase differences can yield a difference in path length that, when accumulated, can lead to a solution for the angles involved. In some embodiments, Transceivers 101-105 may include antenna arrays combined with batteries and circuitry to form complete self-contained devices. Antenna arrays and methods of using the same for determining position and direction of a Smart Device or other Node are described in U.S. Ser. No. 16/775,223, the contents of which are incorporated herein by reference.

In an example, an Agent-supported Transceiver 105 may be located at a position and may transmit a signal of the various types as have been described. Nodes, such as Reference Point Transceivers 101-104 located at reference points in the wireless communication area around the position of the Agent 100 may receive the transmission and determine the angle of arrival of that transmission. Similarly, transmission associated with other transceivers 101-103 may also determine an angle of arrival of transmissions. In some embodiments, transceiver 101-103 may communicate with one or more of: each other, a smart device, a controller or other processor to mathematically process multiple angles and locations of the transceivers and calculate a position of a transmission emanation. In examples where calculations are not performed at a smart device, a communication to the smart device of the calculated position may be communicated.

In certain embodiments of the invention, a direction of interest indicated by Smart Device 101 or a Smart Receptacle (see FIG. 5A 502) may be determined based upon a movement of Smart Device 101 or a Smart Receptacle 502. For example, a device with a controller and an accelerometer, such as mobile Smart Device, may include a user display that allows a direction to be indicated by movement of the device from a determined location acting as a base position towards an As Built feature in an extended position. In some implementations, the Smart Device may first determine a first position based upon triangulation with the reference points and a second position (extended position) also based upon triangulation with the reference points. These position determinations may proceed as described above.

The process of determination of a position based upon triangulation with the reference points may be accomplished, for example via executable software executed by the controller in the Smart Device, such as, for example via running an app on the Smart Device. Logical communications relevant to location determination may include, for example, one or more of: timing signals; SIM information; received signal strength; GPS data; raw radio measurements; Cell-ID; round trip time of a signal; phase; and angle of received/transmitted signal; time of arrival of a signal; a time difference of arrival; and other data useful in determining a location.

In another aspect, captured data may be compared to a library of stored data using image recognition software to ascertain and/or affirm a specific location, elevation and direction of an image capture location and proper alignment with the virtual model.

In an exemplary embodiment, a position of a user may be determined by any of the means described herein. A user may position a sensor of an associated smart device to be pointing in a direction of interest and obtain an image. The image may be passed on to a server with access to database of images containing stored images of the space around the user. Algorithms on the server may compare the stored images to the image captured by the user, and may calculate adjustments to the comparative image based on where the reference image was taken in relationship to the location of the user. Based on the determination that the calculated adjusted image compared to the image obtained by the user in the direction of interest, a direction may be inferred with known location of objects in the reference image. In some variations, the differences in features of the user obtained image compared to a reference image may be used to calculate a direction of interest based upon a location at which the reference image was obtained.

In some examples, stored images may be obtained at multiple angles to improve accuracy of orienteering. These examples may include sensor arrays, audio capture arrays and sensor arrays with multiple data collection angles. In some examples a full 360-degree sensor perspective may be obtained by such arrays. In some directional arrays, a Sensor array (including image capture sensors) may include at least 120 degrees of data capture. By collecting such image collections as the Sensor/Sensor systems are moved, a database of image perspectives may be formed and utilized to assist in orienteering as described.

Non-limiting examples may include image-based identification where a device with some imaging means, including but not limited to a mobile device sensor, tablet device sensor, computer sensor, security sensor, or AR headset sensor, may image points of interest in a direction of interest. These points of interest may be identified. Image recognition software may be used to identify the visualized landscape by its identifying features. Machine learning may be used to train systems using this software to identify specific features of the environment in question.

To create a supplemental topographic part of a model of the environment of a user, laser scanning and/or LiDAR may be performed during the acquisition of imagery for a reference database. A resulting three-dimensional shape model may be modelled with the captured imagery to help in the comparison to user data. Three-dimensional shapes can be used to infer comparative imagery at different angles of acquisition than exist in a database. In another example, a device of a user may have the means of performing laser scanning or LiDAR scanning of the environment as well as obtaining images. The resultant three-dimensional data or a composite of the three-dimensional data, and the imagery may be used to recognize features and determine a direction that the user was facing when they collected the image.

The results of scanning may be stored and presented in different manners. In some examples, scanned data may be represented by a point cloud representation; in other examples an estimated topographic surface representation may be used to visualize the three-dimensional shape data obtained. In some examples, outward facing planes of the surface topography may have the captured imagery superimposed upon them. The resulting image and three-dimensional models may be used to calculate a direction of interest or a device field of view in a dynamic sense or alternatively upon user request.

In some examples other methods of capturing spatially accurate information may include the use of drones and optical scanning techniques which may include high resolution imagery obtained from multiple viewpoints. Scanning may be performed with light based methods such as a CCD sensor. Other methods may include infrared, ultraviolet, acoustic, and magnetic and electric field mapping techniques.

In other embodiments, a single distance to a point of interest in an image, which may be obtained by a laser, other collimated light source, sound source or the like, may be used with models of the environment of the user. A comparison of the imagery and the measurement of the distance of the user to a prominent feature in the image may allow for an orientation of the user to be determined algorithmically.

Figure 2:
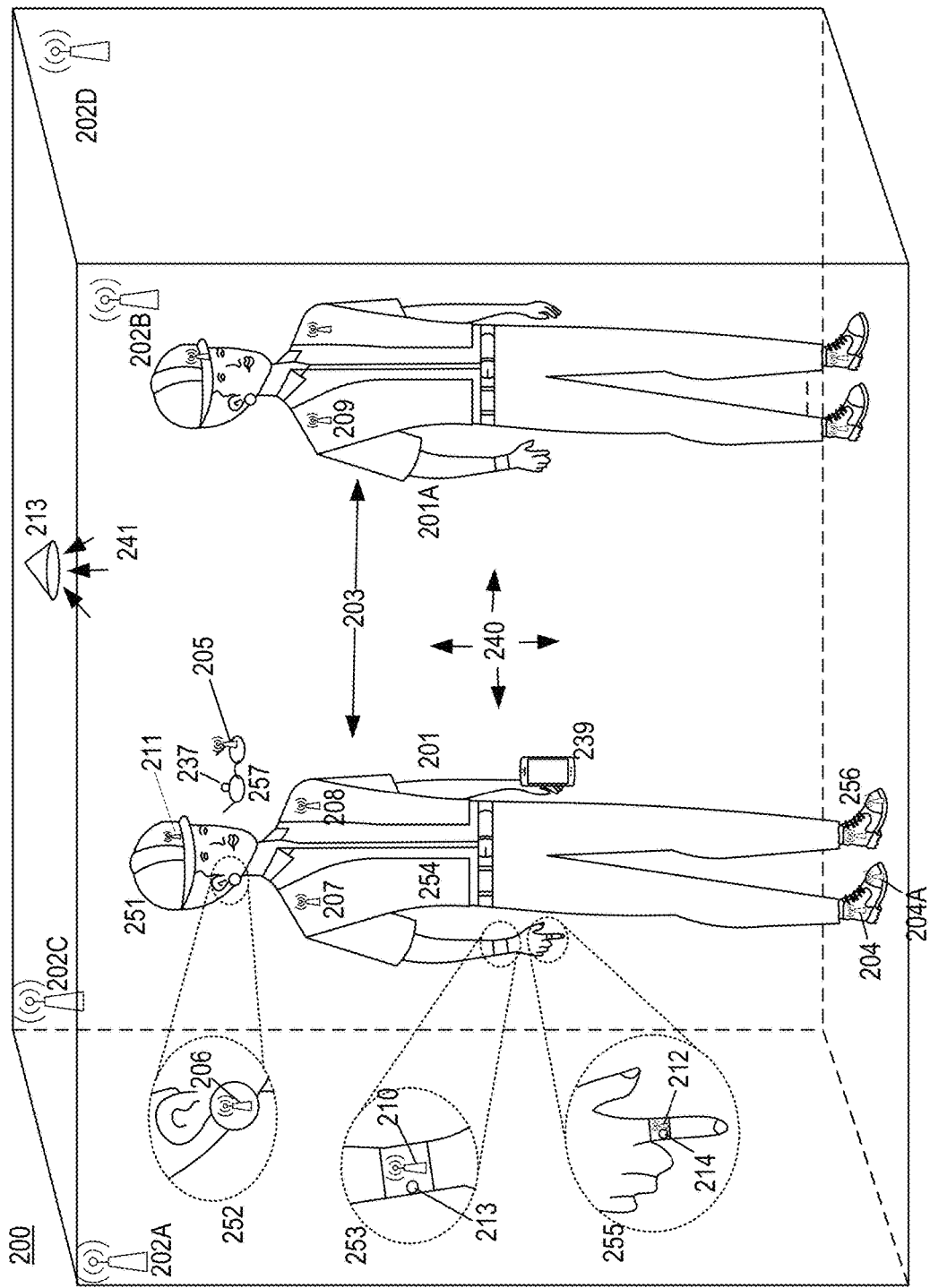
FIG. 2 illustrates a person with wearable wireless communication transceivers.

Referring now to FIG. 2, according to the present invention an Agent, such as a human person 201, supports one or more Transceivers 204-212 within a wireless communication area, such as an interior of a structure 200. The Agent supported Transceivers 204-212 are operative to wirelessly communicate with Reference Point Transceivers 202A-D located within the structure 200. Information included in wireless communications between the Reference Point Transceivers and the Agent supported Transceivers 204-212 include values for variables that may be used to generate a position of the Agent supported Transceivers 204-212.

The Agent supported Transceivers 204-212 are co-located with the Agent resulting from being supported by the Agent, therefore a position of the person 201 may be designated as being the same as the position of one or more of the Agent supported Transceivers 204-212 or some mathematical correlation of the respective positions of the Agent supported Transceivers 204-212, such as for example: an average, a weighted average, a mean, a median, other function or algorithm involving the respective positions of two or more to the Agent supported Transceivers 204-212.

In some embodiments, a person 201 (or other Agent or mammal) will support two or more Transceivers 204-212 and each of the Agent supported Transceivers 204-212 will enter into communication with the Reference Point Transceivers 202A-D in a manner conducive to generating a respective position of the two or more Agent supported Transceivers 204-212 supported by the person 201. A directional vector and/or ray may be calculated based upon respective positions of two or more of the Agent supported Transceivers 204-212 supported by the person 201. The directional vector and/or ray may be used, for example, to designate a forward facing position of the person 201 or a direction of interest associated with the person 201. For example (and discussed in more detail below) headgear 251 may include multiple headgear mounted transceivers 211, such as a transceiver 211 along a front portion of a headgear (front brim or front headband portion or front of eyeglasses) and a second headgear transceiver along a rear portion of the headgear (not shown in FIG. 2) a directional vector and/or ray may be generated from the position of the transceiver along a rear portion of the headgear through a front portion of the headgear (defined by the position of the front portion headgear transceiver 211) and a frontward facing direction (and/or a rearward or sideways facing direction) may be designated based upon the directional vector/ray.

Other wearable items 252-257 may also include Transceivers 204-212, such as those supported at areas of the person 201 other than the person's head. By way of example, Transceivers 204-212 may be attached to, incorporated into, mounted on, held by, or otherwise supported by items wearable by a person 201 or items that may be held in the person's hand.

The present invention additionally provides for Sensors 204-212 (with additional sensors illustrated and discussed in subsequent figures) that are supported by the person 201 or located within the structure 200. The sensors quantify a condition within the structure 200. For example, the condition may be a physical state present in the structure or a physiological state present in the person 201.

In some preferred embodiments, Sensors may be placed on an inner surface of a wearable item such the sensor has access to a skin surface on the person 201. Access to a skin surface may allow, or improve quantification of a physiological condition (sometimes referred to herein as a Biometric). For example, access to a skin surface may allow for electronic quantification of a body temperature, a heart rate, a blood oxygen level, a blood sugar level, blood pressure, intracranial pressure and other conditions present and quantifiable via electronic sensors supported by the person 201.

In other embodiments, a structure sensor 213 may be positioned, such as mounted on an architectural aspect or equipment item, and receive energy from an environment around the sensor in a manner that allows the structure sensor 213 to quantify a condition within the environment. For example, a structure sensor 213 may receive environmental input 241 such as infrared energy into the sensor and based upon the receipt of environmental input 241, such as for example infrared energy, the structural sensor 213 may quantify surface temperatures of items within the structure 200. The items within the structure may include person(2) and the structural sensor may quantify a respective surface temperature of each person 201-201A. If a structural sensor 213 is positioned to receive environmental input, such as infrared energy 241 from a known area, the position of a person 201-201A may be determined via wireless communications (as discussed herein) and a quantified temperature may be correlated to a particular person based upon the location of the person 201-201A and the known area monitored and quantified by the structural sensor 213.

In another aspect, a location of Agent supported Transceivers 204-212 may be determined via wireless communications with Reference Point Transceivers 202A-D and used to designate a forward facing direction of a person 201 at a particular instance in time. Therefore, one or more of: triangulation, trilateration and determination of an angle of transceiving may be used to designate a forward facing position. For example, an AoD and/or AoA may be used to designate a frontward facing direction (or rearward, sideways facing direction) at a particular instance in time (and/or timeframe) while triangulation is used to generate a geospatial position during the same timeframe (or an overlapping timeframe).

As illustrated in FIG. 2, as well as in FIGS. 2A-2F, according to some embodiments of the present invention, sensors 214-236 are also placed in and/or on a wearable item 251-257. The sensors may quantify a condition in an environment that is ambient to the person 201 or quantify a condition experienced by the person 201. For example, a sensor worn in a wrist strap 253 type item, such as a watch or a compressive band or other type wrist strap 253 may include one or more sensor(s) that quantify a condition experienced by the person 201 by measuring physiological conditions experienced by the person, such as, for example: a body temperature, a heart rate, a skin temperature, shaking, falling, impact, vibration, acceleration, deceleration, remaining stationary, appendage movement, head movement, eye movement, and the like.

Sensors in other wearable items, may quantify similar or variant conditions. For example, an accelerometer or piezo device in a footwear 256 may quantify steps. A Transceiver in a ring 212 may quantify hand movement, such as a natural swing movement during walking or running, a rotational movement while operating a steering wheel, a vertical movement while lifting or climbing a ladder, etc., and in some embodiments may work in correlation with an image capture device, such as stereoscopic cameras in a head gear 251 to quantify hand and finger movements that may be processed and translated into control commands.

An eye covering 257 type item supported by the person may include, for example, eye glasses, goggles, an augmented reality (A/R) headset, a virtual reality (V/R) headset, facemask or other item that is generally placed in position in front of a person's 201 eyes may include one or multiple transceivers 205 that may transceive to help determine a position of the person 201 wearing the eye covering 257. The one or multiple transceivers 205 may also transceive in a manner that allows for determination of a forward direction of the eye covering 257 such that a designation of a direction the person 201 is facing may be correlated with the forward direction of the eye covering 257. The forward direction of the eye covering may be determined according to the methods and devices discussed herein for determining a direction, such as a direction of interest.

In another aspect, one or more sensors 237 mounted on the eye covering 257 may monitor and quantify eye movement and a direction of eye focus. A direction of eye focus quantified by the sensor 237 may assist in determining one or more of: a forward facing direction, what the eye is focused on, whether the person 201 is looking down or up, nystagmus movement or other health and/or performance condition.

As discussed above, Transceivers 212-236 may be mounted on a wearable item 251-257 such that as a wearable items with one or more Transceivers 212-236 and a Transceiver 204-212 may quantify a condition experienced by the person 201 wearing the wearable item 251-257. A condition experienced by the person may include one or more physiological state(s) of the person 201, such as, for example, a heartrate, a body temperature, a breathing rate, breathing pause, eye movement, body conductivity, body capacitance, or other biophysical and/or biochemical state or condition.

Sensors incorporated into a wearable item may therefore provide quantification of bodily conditions present in the wearer. The quantified body conditions may be transmitted via a wireless communication to a processor that is operative to identify a bodily condition. For example, the processor may check to ascertain if a quantified body condition is within thresholds determined to indicate a healthy condition of the body; or if the quantified body condition indicates a transitory state that may ultimately result in an unhealthy state; or if the quantified body condition indicates a present state of a human body that is in an unhealthy state.

As further discussed herein, a condition quantified by a sensor may precede execution of a remedial action based upon a value of a variable used to represent the condition quantified by the sensor. In those embodiments that include a body condition being quantified by a sensor worn in a wearable item 251-257 by a person 201, a remedial action may include, by way of non-limiting, one or more of: alerting the person 201 wearing the wearable item 251-257. An alert to the person 201 wearing the wearable item 251-257 may include, for example, a human audible alert, a kinetic action, such as a vibration or TENS (Transcutaneous electrical nerve stimulation), a visual indication (such as a light), or activation of another device perceptible by the person 201. An alert may also be generated that is communicated to a person other than the person 201 wearing the wearable item 251-257, or a server, processor, controller or other automation. For example, a supervisor in a processing plant may receive one or both of an email and a text message indicating that a person 201 wearing a wearable item 251-257 and working in the processing plant has a body temperature that exceeds 100° F. and an elevated heartrate. The supervisor may recognize that a fever and elevated heartrate may be indicative of a viral infection and therefore contact the person 201 wearing the wearable item 251-257 and direct the person 201 to be further assessed. In addition, because the person will also be associated with wireless position tracking via a transceiver included in a wearable wrist band, the present invention may determine where the person 201 has moved about while the person 201 has generated an indication of a fever, e.g. an elevated body temperature. Moreover, a position of a first person 201 may be determined relative to a position of a second person 201A during one or more time intervals. Additional remedial actions may be implemented if the first person 201 has been located at a position within a threshold distance 240 from the second person 201A. For example, both the first person 201 and the second person 201A may be placed in quarantine until such time as it is determined that both the first person 201 and the second person 201A are free of viral infection. Alternatively, in some embodiments, a comparison of a first pattern of wireless positions indicative of a path travelled by a first person 201 and a second pattern of wireless positions indicative of a path travelled by a second person 201A may indicate that the second person 201A is not likely to contract a virus from the first person 201 because the second person 201A did not come within a distance 240 determined to be statistically favorable to transfer of the virus.

In some embodiments, a Transceivers 212-236 may quantify almost any condition present in an area defined by a range of a Reference Point Transceiver 202A-202D communicating with a Transceivers 204-212 associated with a Transceivers 212-236. Embodiments will include an area of communication between the Transceiver 204-212 and the Reference Point Transceivers 202A-202D that includes an interior of a facility or other structure 200, and an area immediately surrounding the structure. As discussed above, a condition quantified by sensors within range of the Reference Point Transceivers 202A-202D may be a physiological state of a person 201. In addition, the condition quantified by sensors within range of the Reference Point Transceivers 202A-202D may include a condition in an environment within the area, such as an atmospheric environment and/or a condition in a structure 200 or an item of machinery.

As such, in some embodiments, a wearable item 251-257 that includes a wristband, headgear, vest, gown, footwear, or other capable of assessing a condition of a person 201 and an environment item, may include sensors 214-236 that quantify a condition present in the person 201 that wears the wearable item 251-257 or a condition ambient to the person 201 wearing the wearable item 251-257. Non-limiting examples of conditions ambient to a person include, temperature, humidity, visible light, IR light, UV light, other electromagnetic energy within a defined bandwidth, movement, vibration, impact, noise, motion or other quantifiable condition.

In some embodiments, one or more sensors 213 may be positioned other than as part of a wearable item 251-257. For example, a sensor 213 may be fixedly attached to a structure 200. The structural sensor 213 attached to the structure 200 may receive environmental input 241 descriptive of an environment surrounding a person 201-201A. The present invention is able to generate a position of a person 201-

201A, quantify a condition in an environment 238 surrounding the person 201-201A, quantify a condition present as a physiological state of the person 201-201A at multiple instances in time and store each position and quantified condition. In addition, the present invention may generate a user interface indicating a present status of the above listed conditions, a chronology of states of conditions and positions, a summary (including mathematical analysis, such as average, mean, weighted average, median etc.).

The present invention will also provide a user interface or other human discernable device, such as a light, audio instruction, mechanical actuation, video, narrative or other communication medium to indicate what actions the controller deems to be appropriate based upon a particular set of conditions quantified by the sensors 214-236 and algorithmic analysis, such as unstructured queries and artificial intelligence. For example, for a viral contagion, such as, for example, COVID-19, a close contact may be defined as anyone who was within six feet of an infected person for at least 15 minutes starting from 48 hours before the person began feeling sick, if it is known that the virus propagates well in an environment with certain temperature and humidity conditions and does not propagate well in an environment with other temperature and humidity conditions, then the present invention may provide an interface indicating a first value for remedial action, such as a distance 240 between persons 201-201A to maintain, or what should be considered "close contact" based upon a first set of environmental conditions that are quantified, and a second value for what should be considered "close contact" for a second set of environmental conditions.

More specifically, if an exemplary virus propagates well in an environment of less than about 10° C. and in humidity of less than about 75%; and the same virus has limited propagation in environments of over 20° C. and atmospheric humidity of about 80% or more, then the present invention may provide an interface or other indicator of a distance 240 defining a first value for a "close contact" based upon a temperature and humidity of an environment in which a people are situated; e.g. a first value defining a distance 240 between persons 201-201A for close contact as 6 feet or less and a second value defining a distance 240 between persons 201-201A for close contact as 12 feet or less. A choice of the first value for clos contact and the second value for close contact will be contingent upon measured quantifications of a temperature and humidity of an environment 238 in which a person 201-201A is situated. Other quantified environmental conditions may become a factor upon which user interface values are based.

In addition to a suggested distance 240 to maintain between persons 201-201A, the present invention provides to sequential position determination for persons 201-201A based upon wireless communication (position based upon wireless communication is discussed in more detail herein). According to the present invention, wireless communication including values of variables capable of determining a position of a transceiver supported by an Agent, such as a person 201-201A is conducted on a periodic and/or episodic basis. Periodic basis includes a times period between wireless communications, such as every t seconds, or every minute, or every five minutes or other time period appropriate to the circumstances, such as a likelihood of movement and power consumption. A wireless communication based upon an episodic basis may include wireless communicating as a response to an event, such as movement detected by a lower powered device, such as accelerometers, solid state magnetic sensors, gimbals and the like, or other relatively low powered device that is capable of detecting movement. Other events may also precede a wireless communication, such as a detection of another person within a defined distance 240, a change in another variable, such as temperature, carbon dioxide level, inert gas level, oxygen level, presence of a chemical, or almost any other measurable quantity. Essentially, if a threshold level of a quantifiable condition is reached, an onboard controller is programmed to conduct wireless communication and calculation of a position of a transceiver conducting the wireless communication.

In another aspect, environmental conditions and person conditions may be measured by sensors included in wearable items worn by a person, or by sensors located in a position conducive to quantifying a condition of one or both of an environment 238 in which the person 201-201A is located and a position conducive to quantifying a condition inherent in the person 201-201A. For example, a sensor 213, such as an infrared (IR), thermistor, thermocouple, or other sensor type may receive environmental input 241 that the sensor 213 may use to quantify a condition, such as, a temperature of the environment 238 or a condition of a person 201-201A. The sensor 214-236 may be located in a wearable item 251-257, or a sensor 213 may be fixed or removably fixed, in a position in a structure 200. Either way a sensor 213-236 may be operative to quantify a temperature condition of a person 201-201A or an environment 240. A value generated by a sensor 213-236 may be stored and/or processed by a controller. Processing may include a mathematical combination of a sensor reading with other sensor readings. A sensor reading may include a sensor generated value of a variable. Combining of values of variables may include aggregating and mathematically processing the sensor generated values of variables.

As illustrated, a wearable item 251-257 may include, by way of non-limiting example, headgear 251, such as a hat, hardhat, headband, skull cap, cap, A/R headset, V/R headset, surgical cap, scrub cap; an earring 252; an wrist strap 253, including an arm band, a watch, a bracelet, or other item that may be positioned around an arm; a torso covering 254, such as a vest, lab coat, scrub; hazmat suit, smock; a ring 255, footwear 256, such as a shoe, boot, sandal, slipper, cleat, sneaker, or other article fitted to a foot. As illustrated, each of the wearable items illustrated 251-257 has a Transceivers 204-212 associated with it. The Transceivers 204-212 may be fixedly attached, removably attached or incorporated into the wearable item.

In some embodiments, a wearable item 251-257, such as for example a ring 255, an earring 252, or any of the other wearable items may include a transceiver that engages in low power, short distance communication, such as for example, one or more of: LPWAN, WhiskerRF, ANT, Near Field Communications (NFC), Zigby, Bluetooth Low Energy, or other low energy type communication. The wearable item may then communicate sensor data to a higher powered smart device 239, such as one or more of: a communications Tag, a Node, a Smart Phone, a Smart headset, a smart watch and the like, wherein the higher powered smart device 239 may engage in wireless communication with one or more Reference Point Transceivers 202A-202D to determine a position of a person 201-201A and also convey through the wireless communications some or all of the digital content generated by sensors 214-236 included with the wearable item 251-257.

For example, in some embodiments a higher powered smart device 239 may receive from the lower powered sensor multiple values of a variable quantifying a condition present in a structure 200, each value of the variable quantifying a condition present in the structure associated with a chronological time value. Variables, and values for variables will depend upon a type of sensor made operative to quantify a condition. Sensors may be chosen based upon which conditions will be quantified. Similarly, a transceiver 202A-213 may vary based upon an environment in which the transceiver will be deployed.

Sensors 214-236 may include an accelerometer to quantify motion (movement, acceleration); magnetic sensor, which may include magnetic field sensors, Hall Effect Sensors and/or Anisotropic Magneto-Resistive (AMR) sensors, magnetometer (3-axis); ambient temperature sensor; ambient light sensor; specific wavelength of light sensor; viii) ambient humidity; Magnet detector (maintenance button, "docked" indication, etc.); ix) sound pressure level (SPL); optical proximity sensor; power source such as a rechargeable lithium polymer battery; USB connector for charging and/or data transfer; NFC (near field communications) (tag or reader); Battery voltage sensing; audio alert, such as a Beeper; Vibrator; LED indicator(s); manual switch such as a tactile button; Inductive charging; vibration detection; air quality sensing such as $CO_2$, VOC and the like; specific gas detection (CO, $CO_2$, $H_2S$, particulate); Gesture sensing (sense hand swipes over device); tap and double tap detection; Agent fall detection; freefall detection; shock and/or impact detection; IR (infrared) beacon TX and/or RX; pedometer; activity meter; processor enhanced audio monitoring (e.g. listen for fire alarm siren); heartrate monitor; blood oxygen sensing; OLED display; electronic ink display; and most any other electronic sensor of a quantifiable condition.

By way of non-limiting example Transceivers 202-212 may be operative to perform wireless communications suitable for real time location functionality and/or data transfer, transmitting and receiving capabilities using one or more modalities such as: UWB; Bluetooth, including BLE; WiFi RTT; infrared; ultrasonic; sonic; sub GHz; or other modality.

In some embodiments, communication between transceiver, such as those included in Tags, Nodes and/or Smart Devices may be achieved by a burst transmission protocol, such as low-power derivative of Gaussian pulses. In exemplary embodiments, the burst transmission protocol may transmit radio waves having a frequency of 3.0 GHz-11.0 GHz, with a high bandwidth of approximately 500 MHz-1.3 GHz. In some embodiments, the bandwidth may be based on a tolerance from an arithmetic central frequency; for example, if the central frequency for the burst transmissions is 6.0 GHz, then the bandwidth may be a relative tolerance, such as 20% of 6.0 GHz (i.e., 1.2 GHz). An interval between individual pulses may be uniform or variable, based on an implemented encoding scheme. In some exemplary embodiments, burst transmissions may lack carrier waves. Transceiving modalities that may be implemented using burst transmission protocol according to the present invention, include, ultra-wideband, sub-GHz, and industrial, scientific and medical ("ISM") radio bands within the frequency range of 6.7 MHz (megahertz) and 250 GHz.

In some exemplary embodiments, one or more pulses of wireless communication may be relatively short in duration (i.e., 0.01 ns-10 ns). The total pulse train may be written as the sum of individual, time-shifted pulses; i.e., $s(t) = \Sigma_{n=0}^{\infty} a_n p(t-\tau_n)$, where s(t) is the pulse train signal, p(t) is a characteristic pulse shape, $a_n$ is the amplitude of the nth pulse, and $\tau_n$ is the time-offset of the nth pulse.

When two nodes exchange burst transmissions, they may be able to detect a range or distance between the two nodes. This may be accomplished through a "time of flight" (ToF) measurement. The ToF measurement may be made by or supplemented with a time difference of arrival (TDOA) or time delay estimation (TDE). TDOA may rely on a measurement of the amount of time it takes for a signal transmitted by one node to reach a plurality of other nodes. Using multilateration techniques, a location of the transmitting node may be estimated.

Figure 2A:
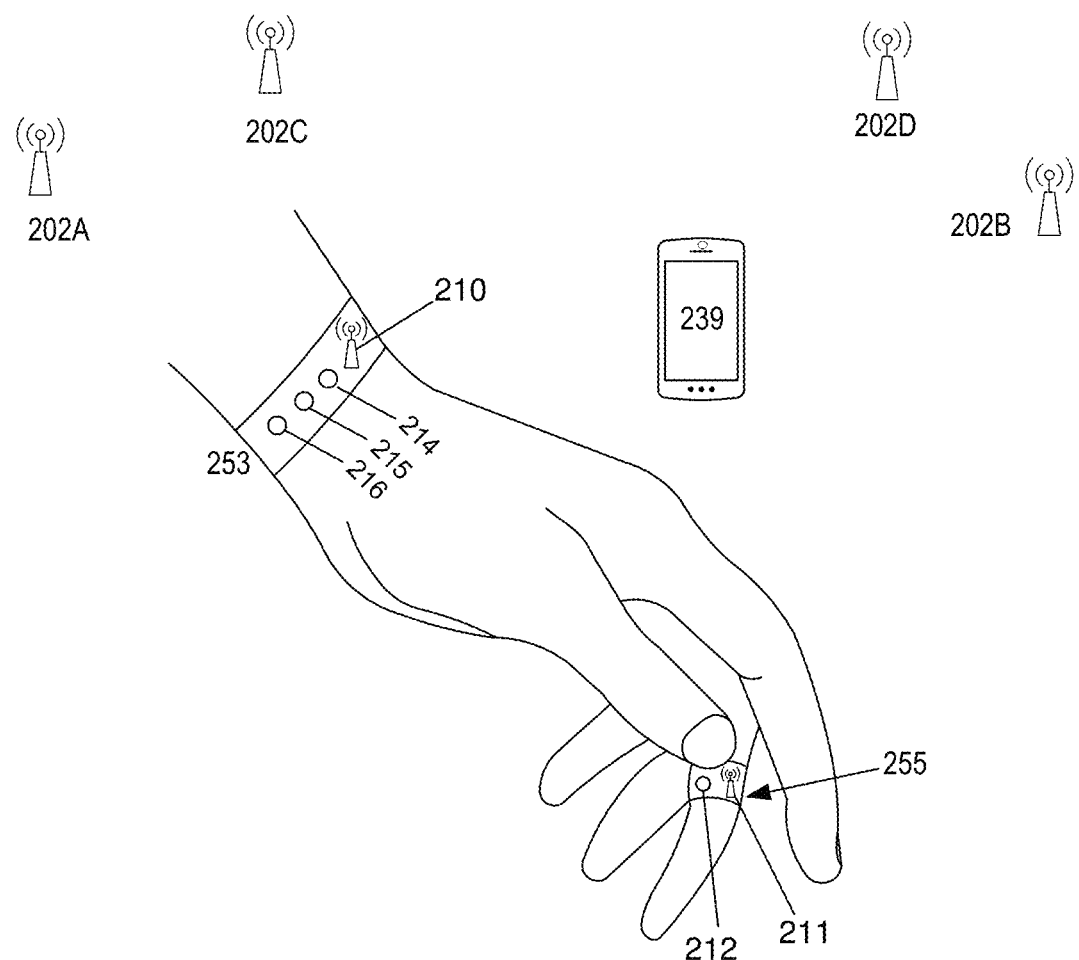
FIG. 2A illustrates wearable items with transceivers and sensors.
Figure 2B:
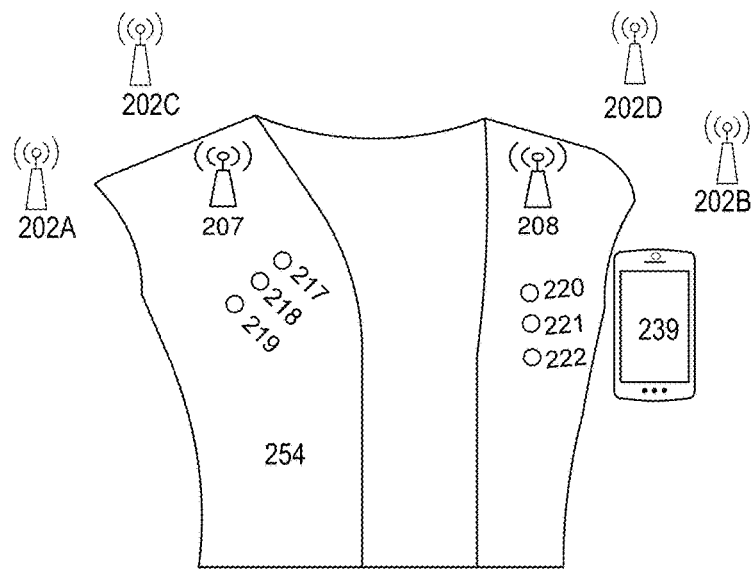
FIG. 2B illustrates a wearable item including vest type garment with transceivers and sensors
Figure 2C:
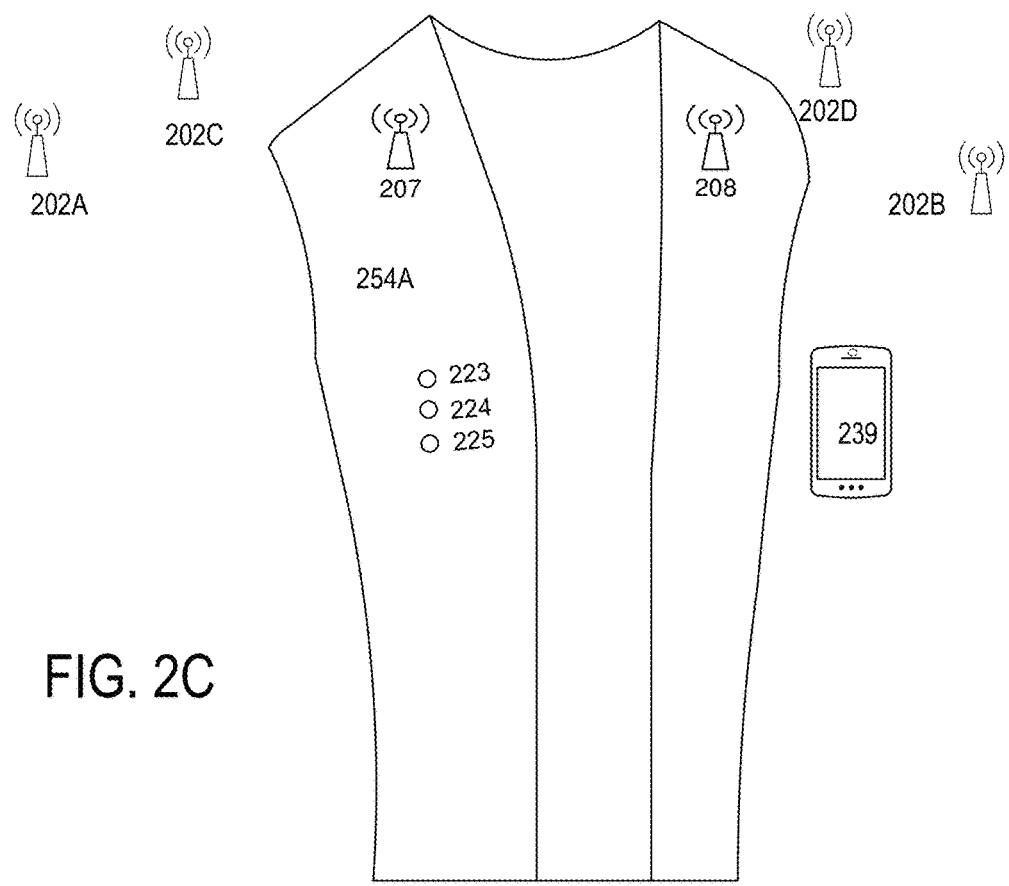
FIG. 2C illustrates a wearable item that is torso supported with transceivers and sensors.
Figure 2D:
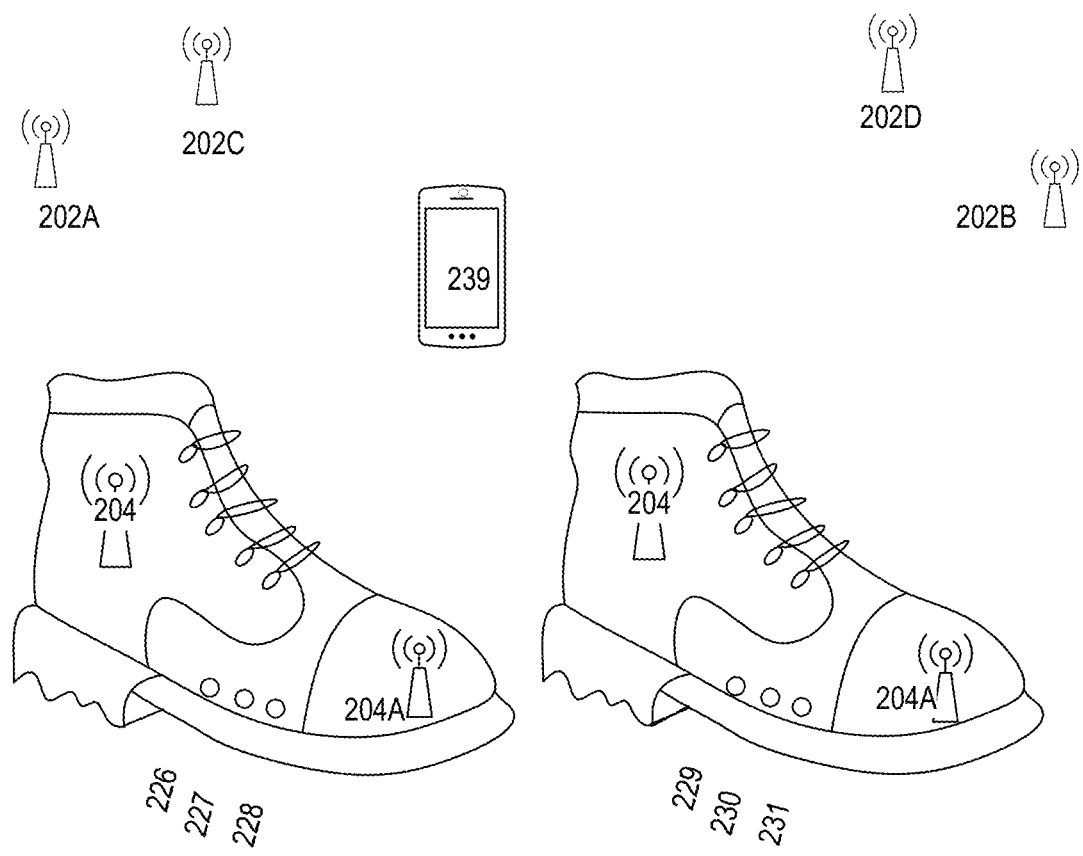
FIG. 2D illustrates wearable item including footwear with transceivers and sensors.
Figure 2E:
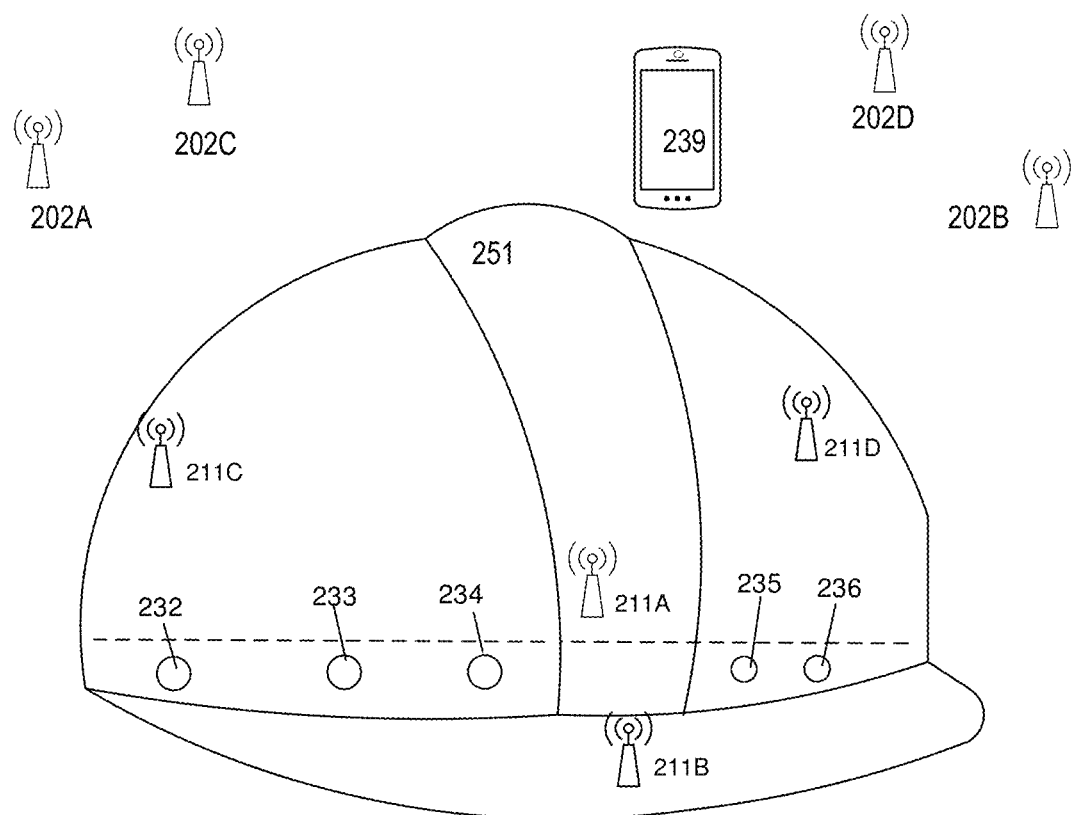
FIG. 2E illustrates a wearable item including headgear with transceivers and sensors.

Referring now to FIGS. 2A-2E, in various embodiments, a wearable item 251-256 may take appropriate forms adapted to be worn or otherwise supported by various parts of a human person 201-201A. For example, FIG. 2A illustrates an arm supported wearable item 253 which may be in the form of a wrist band or arm band or other item that is securable or otherwise supported on an arm of a human person. FIG. 2A also illustrates a finger supported wearable item 255 in the form a ring or other device securable upon a finger of a human person 201-201A. FIGS. 2B-2C illustrate torso supported wearable items 254-254A including a vest 254 and a lab coat 254A or other gown type apparel. FIG. 2D illustrates footwear 256 and FIG. 2E illustrates a wearable item in the form of a headgear 251.

Each wearable item 251-256 may include at least one wireless transceiver 204-212 and one or more sensors 213-236. As discussed herein, the wireless transceiver 204-212 may include a solid state components operable to transmit and/or receive wireless communications. The wireless communications may utilize any of the modalities discussed herein. The transceivers may wirelessly communicate with one or more Reference Point Transceivers 202A-202D and/or a smart device 239, such as a smart phone, smart tablet, smart headgear and the like. Wireless communications may include relatively higher powered and longer range modality, such as UWB, Bluetooth, WiFi, cellular or satellite communications and/or lower powered and shorter range communication modality, such as Zigby, ANT, BLE, or other low power protocol.

Those wearable items 251-256 that are capable of supporting more than one wireless transceiver may be operative to engage in wireless communications with Reference Point Transceivers 202A-202D and generate positional coordinates for each transceiver 204-212 (as illustrated wearable items 251, 254, 256 include multiple transceivers, but any wearable item with a large enough area may include multiple transceivers 204-212). Two or more sets of positional coordinates may be referenced to generate a direction of interest. In the present invention a direction of interest may include a direction a person 201-201A is facing. Accordingly, a headgear 251, a vest 254 and/or a shoe 256 may include multiple transceivers 211A-211D, 207-209 and 204-204A respectively for which corresponding positional coordinates may be generated based upon values of variables transceived according to the methods an apparatus described herein. The multiple positional coordinates may be used in turn to generate a direction of interest, such as, a forward facing direction. A forward facing direction may be important in certain safety situations, such as in the case of a contagion that may be spread by a cough, sneeze of exhale. It may be important to know a separation distance 203 between a first person 201 to a second person 201A in the forward direction. A separation distance 203 in a rearward direction may not have as short a critical distance.

In some embodiments, Sensors 213-236 are hardwired or otherwise in physical logical communication with connected to transceivers 204-212 included in a same wearable device. In physical logical communication may include, by way of non-limiting example, on a same printed circuit board (PCB); in a same semiconductor chip; connected by a circuit tracer or wired connection; or other physical logic pathway capable of conveying a digital value.

Transceivers 213-236 may be operative to engage in wireless communication with one or more of: Reference Point Transceivers 202A-202D; a smart device 239, such as a Smart Phone, Smart Tablet or Smart Headgear; a cellular network; a satellite network; a mesh network or other logical network.

Figure 2F:
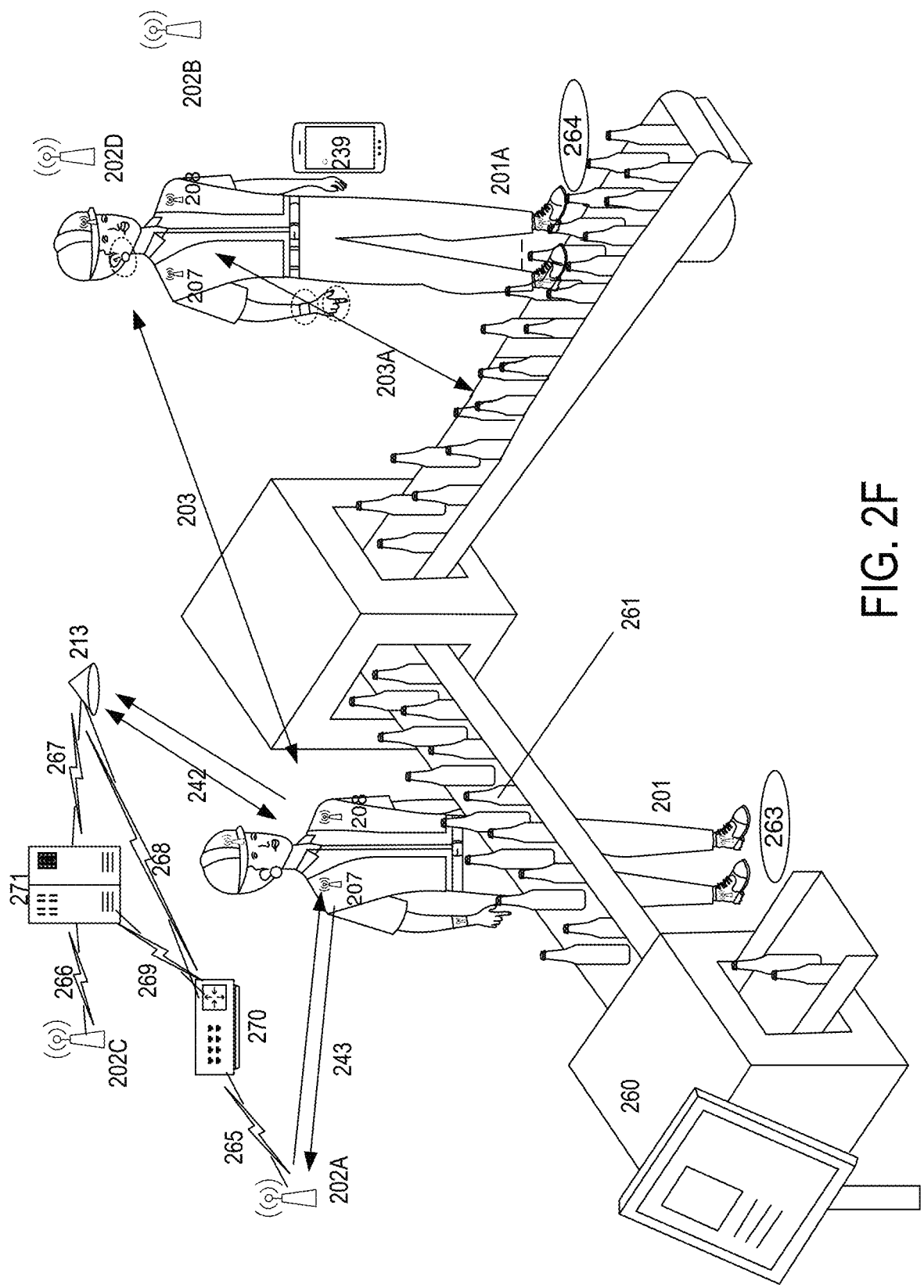
FIG. 2F illustrates a processing plant environment with persons and sensors and transceivers.

Referring now to FIG. 2F, a first person 201 and a second person 201A are illustrated in place to interact with processing equipment 260. Transceivers 207-208 may be supported by the persons 201-201A and engage in wireless communications 243 with one or more Reference Point Transceivers 202A-202D, and values for variables included in the wireless communications 243 may be used to generate location coordinates indicating a respective location 263-264 for the persons 201-201A. Various communications 265-269 are illustrated. Respective locations 263-264 may be referenced to determine separation distance 203 between persons 201-201A and also a separation distance between a person 201A and an item of equipment 260 or other item surface, such as a surface of a product 261. For products such as food items or pharmaceuticals, contamination with a contagion may be particularly sensitive. Separation distance 203-203A may be used to determine a risk on contamination with a contagion. A length of time may also be determined based upon a sequence of wireless communications 243 at known time intervals, wherein the wireless communications are used to generate a location 263-264 of an Agent, such as a person 201-201A.

Ongoing determination of a location 263-264 of an Agent, such as a person 201-201A may also be used to ensure that the person 201-201A does not traverse and area designated as a contaminated area, such as a raw food area, or a chemically contaminated area, and then proceed to a controlled area, such as a non-contaminated area, such as an area with food or other product ready for distribution to the public.

Devices involved in the generation and/or storage and/or transmitting of digital content, such as, one or more of: agent supported transceivers 207-208, reference point transceivers 202A-202D, gateways 270, and servers 271 may each engage in direct logical communications and/or in logical communications with an intermediary device. For example, a reference point transceiver 202A-202D may engage in logical communication with a gateway 270 or other intermediary device and the gateway 270 may engage in logical communication 269 with a server 271; or the reference point transceiver 202A-202D may engage in logical communication 267 directly with the server 271. In various embodiments of the present invention, any or all of the devices (e.g. sensors, transceivers, gateways, servers) involved in generation and/or storage and/or transmitting of digital content, may aggregate, store and or process digital content that the device has access to.

Also, variations on a location of a sensor and a transceiver are within the scope of the present invention. As discussed above, a Sensor 204-213 may be located on a wearable item 251-257 or a sensor 213 may be positioned at a point extraneous to a person 201-201A, such as mounted on an architectural aspect (such as, for example, a doorway, a hall entrance, a turnstile or other crowd movement control device; and receive sensor input 242 from a person 201 useful to quantify a condition of the person 201. Transceivers 207-208 may determine a location of a person 201-201A that correlates with a sensor 213 quantification of a condition present with the person 201-201A based upon input 242 received from the person 201-201A. Based upon a location 263 of a person 201, a processor (such as those present in a gateway 270, server 271 or smart device 239) which person is associated with a condition quantified by the sensor 213 mounted on an architectural aspect.

Some embodiments may also include a sensor 213 capable of receiving input 242 sufficient to quantify biometric based identification of the person 201, and/or a physiological state present in the person 201. For example, sensor 213 may receive input enabling facial recognition of the person 201 and correlate input from a sensor 204-213 to quantify a physiological condition and a facial recognition identification. Transceivers 207-208 may engage in wireless communications sufficient to determine a location 263 of the person 201 when the physiological condition and a facial recognition identification took place via other sensors than those co-located with the transceivers supported by the Agent.

Figure 3:
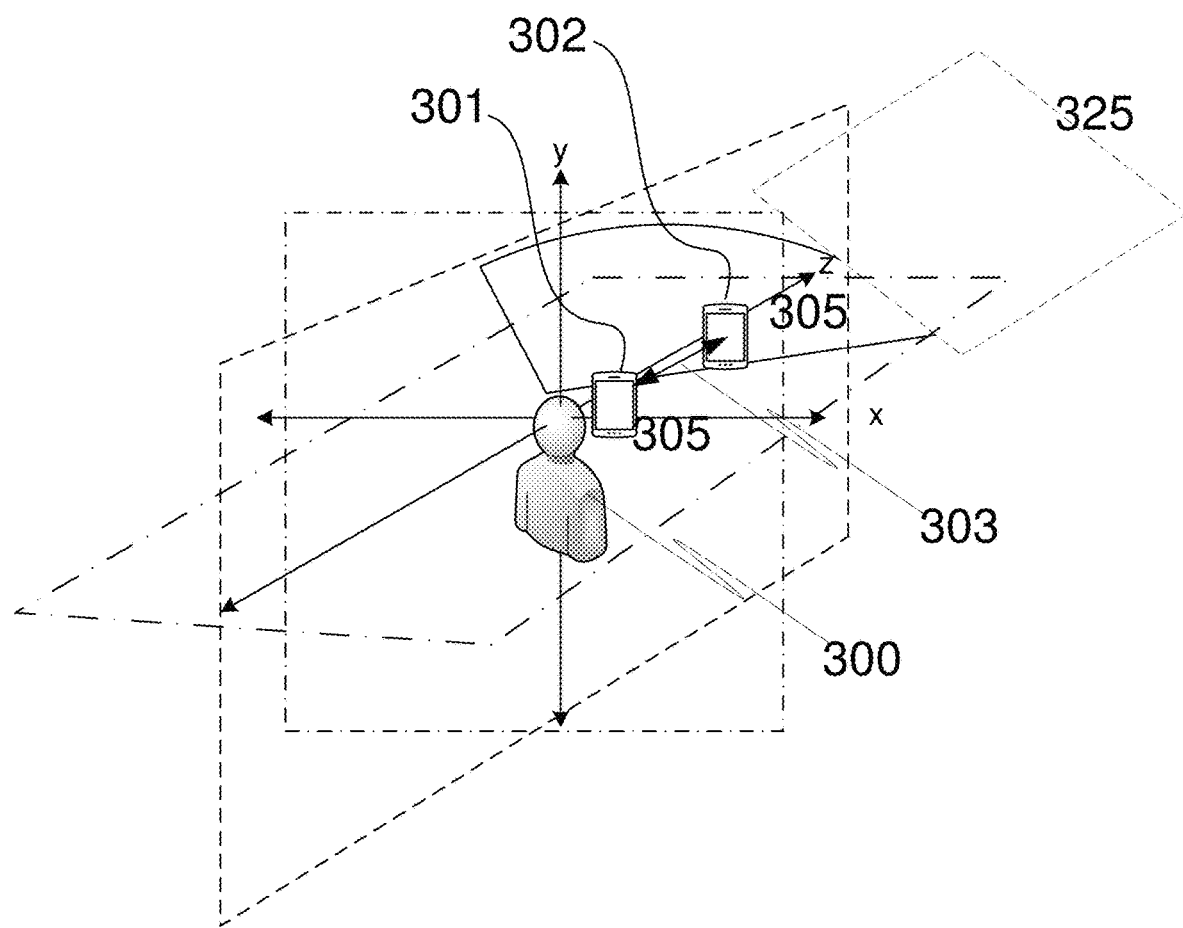
FIG. 3 illustrates methods of orienteering by device movement.

Referring now to FIG. 3, methods and devices for determining a direction that may be referenced for one or both of data capture and data presentation of a particular portion of the virtual representation of surroundings of a user. An Agent 300 may position a Transceiver 305 in a first position 301 proximate to a portion in a space of interest 325. The first position 301 of the Transceiver 305 may be determined and recorded. The Agent 300 may then relocate the Transceiver 305 to a second position 302 in a general direction of the portion in space of interest. With associated position information obtained for the first and second positions a controller in an external system or in an associated Transceiver 305 may generate one or both of a ray and a vector towards the portion of a space of interest.

In some embodiments, the vector may have a length determined by a controller that is based upon a distance to a feature of interest in space as represented in a model on the controller in the direction of the generated vector. The vector may represent a distance 303 from the second position 302 to the space of interest 325 along the axis defined by a line between the first position 301 and the second position 302. In contrast, a ray may include just a starting point and a direction.

In still other embodiments, a device with a controller and an accelerometer, such as mobile phone, tablet or other Smart Device that includes a Transceiver 305, may include a user display that allows a direction to be indicated by movement of the device from a determined location acting as a base position towards an point in a direction of interest or representing a center of an RTA of the device. The movement may occur to a second location in an extended position. In some implementations, the Smart Device determines a first position 301 based upon triangulation with the reference points. The process of determination of a position based upon triangulation with the reference points may be accomplished, for example via executable software interacting with a controller in the Smart Device, such as, for example by running an app on the Transceiver 305.

An array of antennas positioned at a user reference point may allow for the accurate receipt of orientation information from a transmitter. As discussed earlier a combination devices with arrays of antennas may be used to calculation a position. A single Node with an array of antennas can be used for orienteering and determining a direction of interest. Each of the antennas in such an array receiving a signal from a source may have different phase aspects of the received signal at the antennas due to different distances that the emitted signal passes through. The phase differences can be turned into a computed angle that the source makes with the antenna array.

Referring to FIGS. 4A-D a series of exemplary devices employing matrices (or arrays) of antennas for use with Nodes that communicate wirelessly, such as via exemplary UWB, Sonic, Bluetooth, a Wi-Fi or other modality, is illustrated. Linear antenna arrays 401 are illustrated in FIG. 4A. Rectangular antenna arrays 402 are illustrated in FIG. 4B. Circular antenna arrays 403 are illustrated in FIG. 4C, other shapes for arrays are within the scope of the invention. In addition, an antenna array may be omni-directional or directional.

In some embodiments, see FIG. 4D item 404, a Smart Device 405 may include one or more Nodes 406 internal to the Smart Device 405 or fixedly attached or removably attached to the Smart Device 405. Each Node 406 may include antenna arrays combined with a power source and circuitry to form complete self-contained devices. The Nodes 406 or a controller may determine an RTT, time of arrival, AoA and/or AoD or other related angular determinations based upon values for variables involved in wireless communications. For example, a composite device 404 may be formed when a Node 406 with a configuration of antennas, such as the illustrated exemplary circular configuration of antennas 407, is attached to a Smart Device 405. The Node 406 attached to the Smart Device 405 may communicate information from and to the Smart Device 405 including calculated results received from or about another Node 406, such as a Node 406 fixed as a Reference Point Transceiver or a Node with dynamic locations, wherein the wireless communications are conducive to generation of data useful for determination of a position (e.g. timing data, angles of departure and/or arrival, amplitude, strength, phase change, etc.). A combination of angles from multiple fixed reference points to the antenna array can allow for a location of a user in space. However, with even a single wireless source able to communicate with the antenna array, it may be possible to determine a direction of interest or a device related field of view.

An array of antennas positioned at a reference point may allow for the accurate receipt of orientation information from a transmitter. As discussed earlier a combination devices with arrays of antennas may be used to calculation a position. A single Node with an array of antennas can be used for orienteering and determining a direction of interest. Each of the antennas in such an array receiving a signal from a source will have different phase aspects of the received signal at the antennas due to different distances that the emitted signal passes through. The phase differences can be turned into a computed angle that the source makes with the antenna array.

Figure 5A:
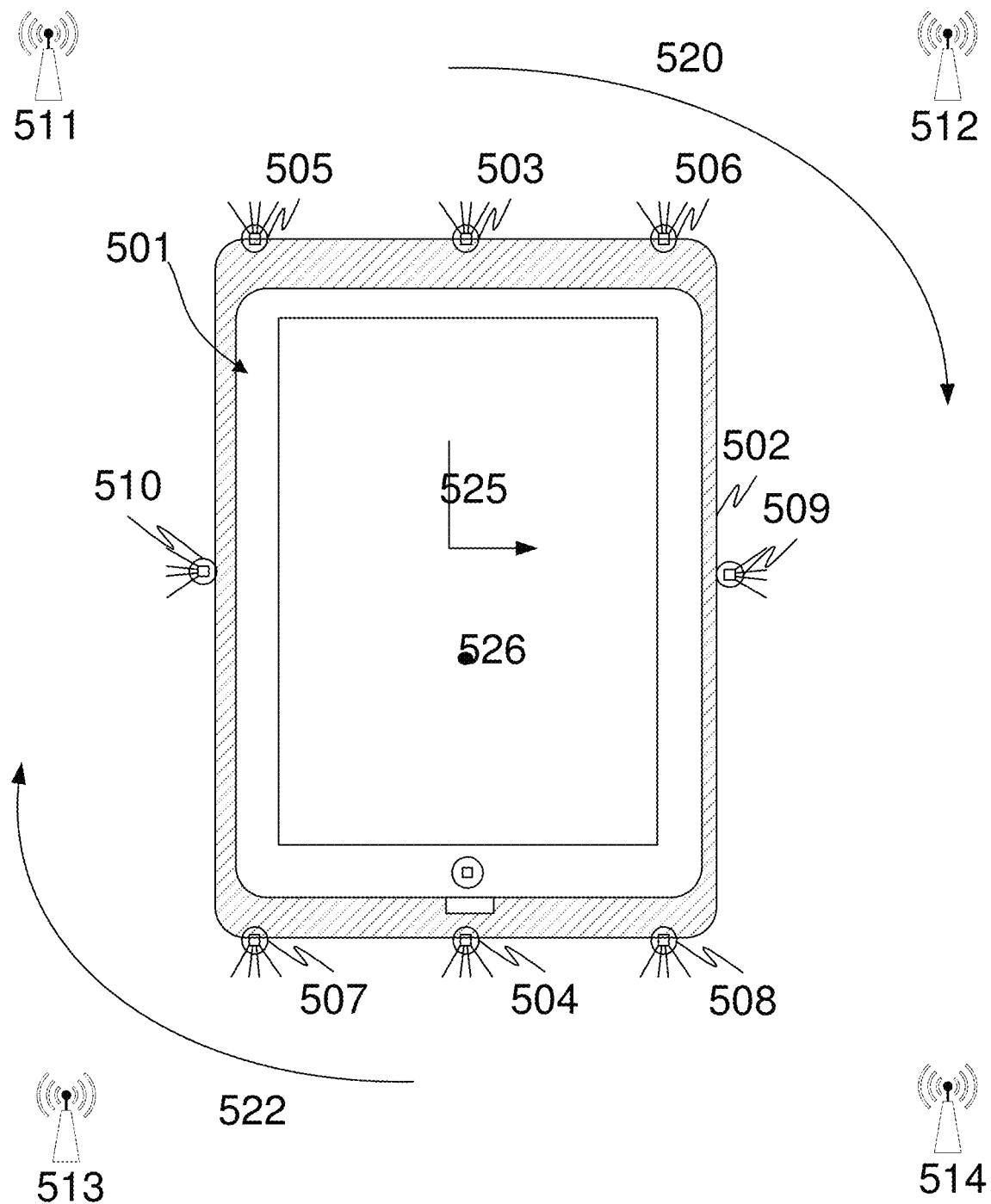
FIG. 5A illustrates an exemplary Smart Device with an array of antennas.

Referring now to FIG. 5A, in some embodiments, one or both of a Smart Device 501 and a Smart Receptacle 502 may incorporate multiple Transceivers 503-510 and a direction of interest may be ascertained by generating a vector 526 passing through a respective position of each of at least two of the transceivers (as illustrated through transceiver 505 and 507). The respective positions of each of the Transceivers 503-510 supported by the Smart Device 501 and/or Smart Receptacle 502 may be ascertained according to the methods presented herein, including for example via triangulation, trilateration, signal strength analysis, RTT, AoD, AoA, topography recognition, and the like. Reference Position Transceivers 511-514 may be fixed in a certain location.

In some embodiments, one or both of the Smart Device 501 and the Smart Receptacle 502 incorporating Transceivers 503-510 may be rotated in a manner (such as, for example in a clockwise or counterclockwise movement 520, 522 relative to a display screen 515) that repositions one or more Transceivers 503-510 from a first position to a second position. A vector 526 may be generated at an angle that is zero degrees with a plane of a display screen 515 or perpendicular 525 or some other designated angle in relation to the Smart Device 501 and an associated display screen 515. In some embodiments, an angle in relation to the Smart Device 501 is perpendicular 525 to a display screen 515 and thereby viewable via a forward-looking sensor (or other CCD or LIDAR device) on the smart device. In addition, a mirror or other angle-altering device may be used in conjunction with a CCD, LIDAR or other energy receiving device.

Movements of a Smart Device 501 equipped with an antenna array can be determined via relative positions of the antenna and/or via operation of an accelerometer within the Smart Device 501 or Smart Receptacle 502. Rough movement sense may be inferred with a single source to the antenna array. However, with multiple sources, the positional movement of each of the antennas can be used to sense many types of movements including translations and rotations.

A user may position the Smart Device 501 such that an object in a direction of interest 525 is within in the CCD view. The Smart Device 501 may then be moved to reposition one or more of the Transceivers 503-510 from a first position to a second position and thereby capture the direction of interest 525 via a generation of a vector 526 in the direction of interest 525.

In addition to movement of the Smart Device 501 and/or the Smart Receptacle 502 may include a magnetic force detection device 523, such as a magnetometer. A registration of a magnetic force may be determined in relation to a particular direction of interest 525 and a subsequent determination of magnetic force referenced or provide a subsequent orientation of the Smart Device 501 or Smart Receptable 502.

In some embodiments, the magnetic force detection device 523 may be used combination with, or in place of directional movement of the Smart Device Transceivers 503-507 to quantify a direction of interest 525 to a user. Embodiments may include an electronic and/or magnetic sensor to indicate a direction of interest 525 when a Smart Device 501 and/or Smart Receptacle 502 is aligned in a direction of interest 525. Alignment may include, for example, pointing a specified side of a Smart Device 501 and/or Smart Receptacle 502, or pointing an arrow or other symbol displayed upon a user interface on the Smart Device 501 towards a direction of interest 525.

A magnetic force detection device 523 may detect a magnetic field particular to a setting that a Smart Device is located. For example, in some embodiments, a particular structure or other setting may have a magnetic force that is primarily subject to the earth's magnetic field or may be primarily subject to electromagnetic forces from equipment, power lines, or some other magnetic influence or disturbance. An initial quantification of a magnetic influence at a first instance in time may be completed and may be compared to a subsequent quantification of magnetic influence at a later instance in time. In this manner an initial direction of interest indicated by a position, orientation, pitch and yaw of a Node, such as a Smart Device may be compared to a subsequent position, orientation, pitch and yaw of the Smart Device.

In some embodiments, an initial position, pitch and yaw of a Smart Device 501 may be described as a relative angle to a presiding magnetic force. Examples of presiding magnetic forces include, magnetic influences of electrical charges, Earth's magnetic field, magnetized materials, permanent magnetic material, strong magnetic fields, ferromagnetism, ferrimagnetism, antiferromagnetism, paramagnetism, and diamagnetism, or electric fields that are generated at reference nodes at known positions which may be locally used to indicate a direction of interest.

Smart devices may include electronic magnetic sensors as part of their device infrastructure. The magnetic sensors may typically include sensing elements deployed along three axis. In some examples, the magnetic sensors may be supplemented with electronic accelerometers, such as MEMS accelerometers.

In some examples the magnetic sensors may measure a sensed magnetic field perpendicular to the body of the sensor through a Hall effect sensor. In some examples, a Hall effect sensor may be built into silicon to generate a relatively sensitive sensing capability for magnetic fields. In some Hall effect sensors, electrons and holes flowing in a region of the silicon may interact with the regional magnetic field and build up on the fringes of the conduction region, thus generating a measurable voltage potential. In other examples, anisotropic magnetoresistance sensors may sensitively detect the magnetic field at the device as a significant change in resistance of structure elements in the device.

In still further examples, giant magnetoresistance (GMR) sensors may detect the magnetic field. In some of these examples, the GMR sensors may detect a magnetic field with a current-perpendicular-to-plane (CPP) GMR configuration. In other examples, a current-in-plane (CIP) GMR sensor configuration may be used. The resulting three-axis magnetic sensors may perform a sensitive compass function to determine a direction of a specified portion of the Smart Device and/or an edge of the smart device relative to the local magnetic field environment. A specified portion of the Smart Device may be indicated via a user interface presented on a screen of the Smart Device.

Figure 5B:
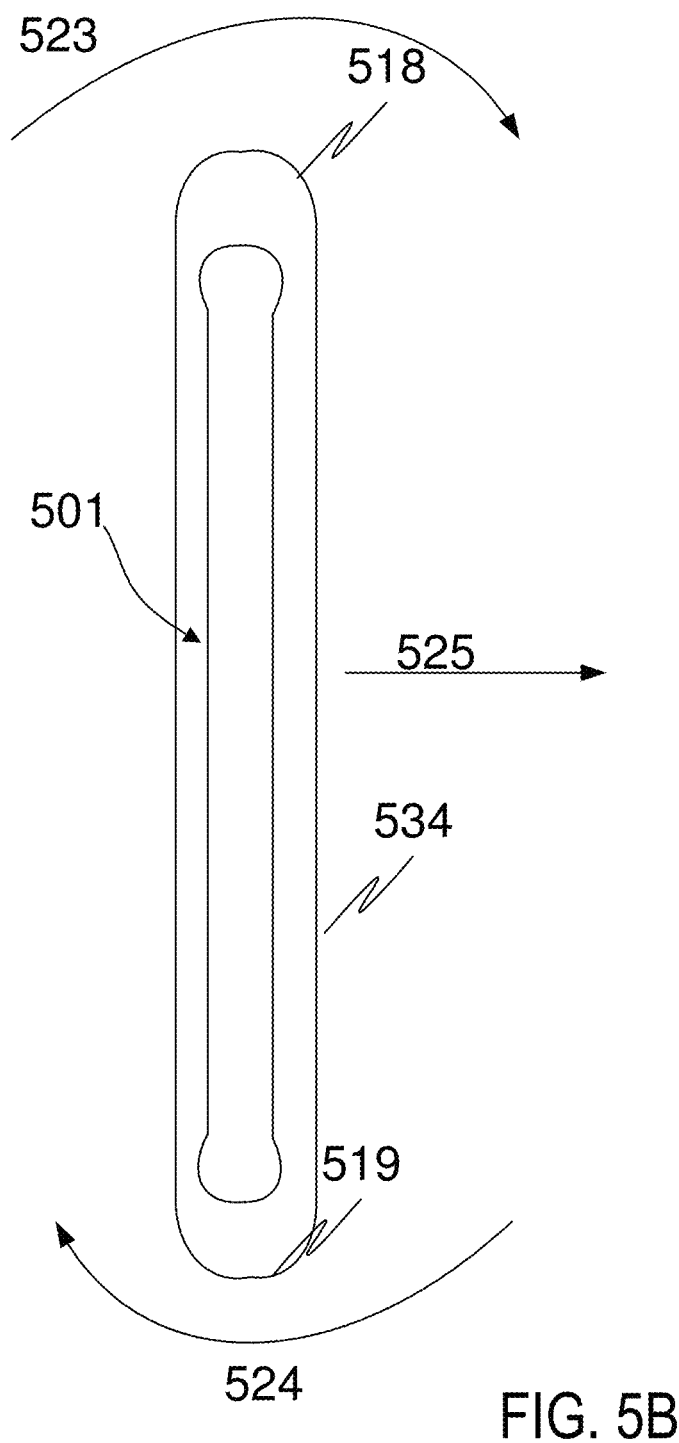
FIG. 5B illustrates exemplary methods of indicating directions with Smart Devices and antenna arrays.

Referring now to FIG. 5B, as illustrated, a vector in a direction of interest 525 may be based upon a rocking motion 523-524 of the Smart Device 501, such as a movement of an upper edge 518 in a forward arcuate movement 523. The lower edge 519 may also be moved in a complementary arcuate movement 524 or remain stationary. The movement of one or both the upper edge 518 and lower edge 519 also results in movement of one or more Transceivers 503-510 (Shown in FIG. 5A) and/or registration in an onboard accelerometer 534. The movement of the Transceivers 503-510 (Shown in FIG. 5A) will preferably be a sufficient distance to register disparate geospatial positions based upon wireless transmissions and/or sufficient to register movement via the accelerometer 534.

As presented herein, a direction dimension may be based upon one or more of: a wireless position of two or more transceivers, a movement of a device, a magnetic force determination, a LIDAR transmission and receiving, CCD energy determinations and other assessments of an environment containing the Smart Device and/or Smart Receptacle. For example, a device with a controller and an accelerometer, such as a mobile Smart Device, may include a user display that allows a direction to be indicated by movement of the device from a determined location acting as a base position towards a feature in the intended direction where the movement results in an extended position. In some implementations, the Smart Device may first determine a first position based upon triangulation with the reference points and a second position (extended position) also based upon triangulation with the reference points.

As described above, facing a mobile device towards an area in a Structure and movement of the mobile device in a particular pattern may be used to ascertain a specific area in space to be interpreted by various methods.

Figure 5C:
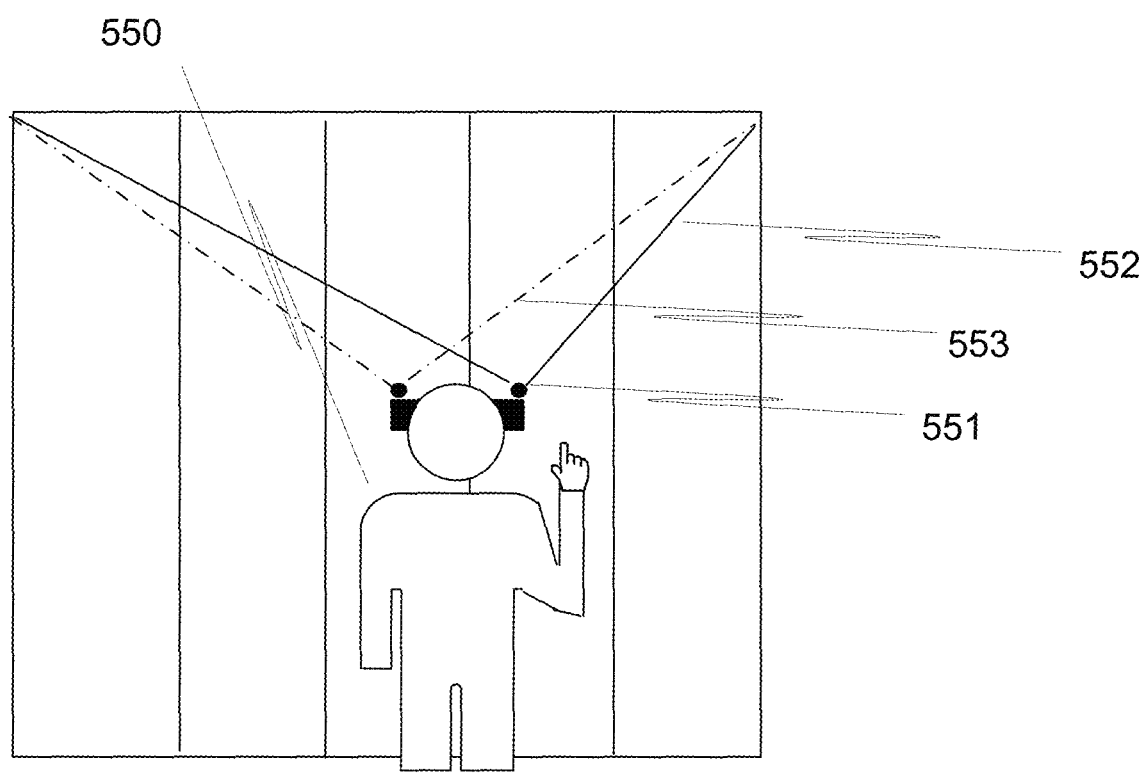
FIG. 5C illustrates an exemplary method of a user utilizing an oriented stereoscopic sensor system to orient a direction of interest.

Referring to FIG. 5C, an illustration of an Agent 550 utilizing an oriented stereoscopic sensor system 551 to orient a direction of interest is shown. The stereoscopic sensor system 551 may obtain two different images from different viewpoints 552-553 which may be used to create topographical shape profiles algorithmically. A controller may obtain the image and topographic data and algorithmically compare them to previously stored images and topographic data in the general environment of the user. The resulting comparison of the imagery and topography may determine an orientation in space of the Agent 550 and in some examples determine a device field of view. The controller may utilize this determined field of view for various functionality as described herein.

Figure 6:
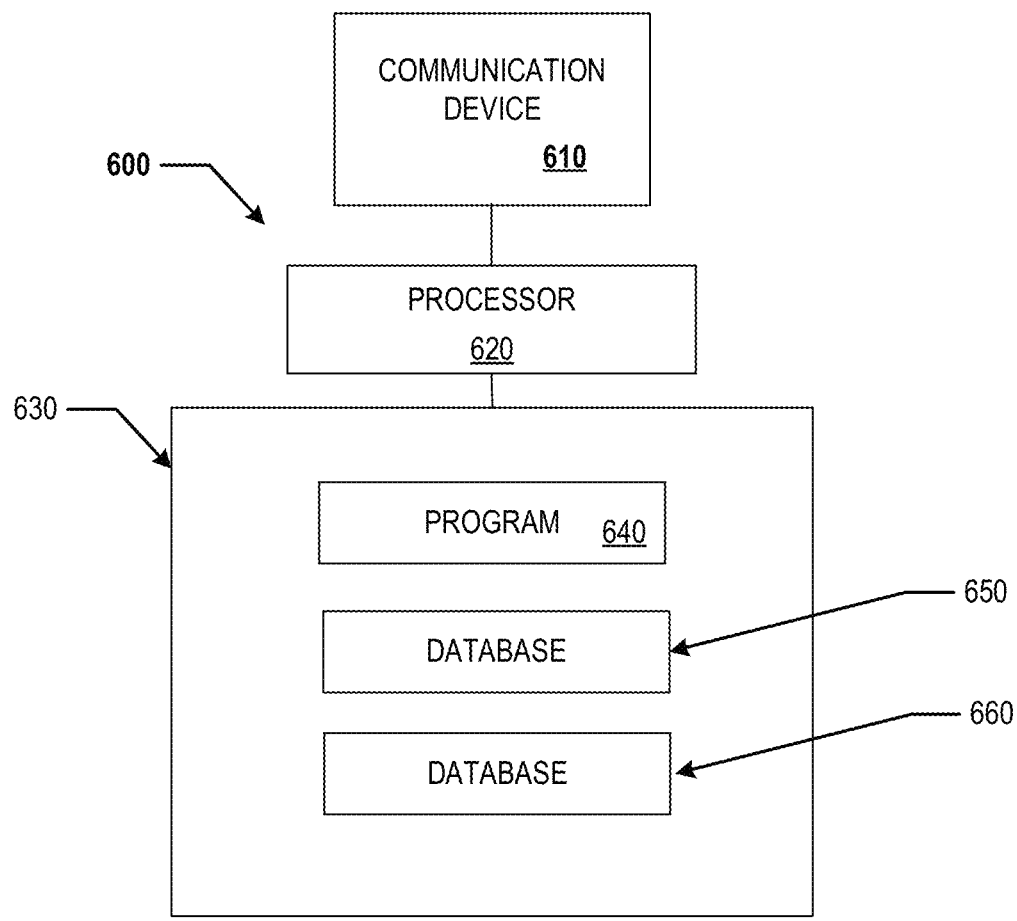
FIG. 6 illustrates apparatus that may be used to implement aspects of the present disclosure including executable software.

Referring now to FIG. 6 an automated controller is illustrated that may be used to implement various aspects of the present invention, in various embodiments, and for various aspects of the present invention, controller 600 may be included in one or more of: a wireless tablet or handheld device, a server, a rack mounted processor unit. The controller may be included in one or more of the apparatus described above, such as a Smart Device, Smart Tablet, Headgear, Smart Watch, Smart Ring or other Smart Device. The controller 600 includes a processor unit 620, such as one or more semiconductor based processors, coupled to a communication device 610 configured to communicate via a communication network. The communication device 610 may be used to communicate, for example, via a distributed network such as a cellular network, an IP network, the Internet or other distributed logic communication network.

The processor unit 620 is also in communication with a storage device 630. The storage device 630 may comprise any appropriate information storage device, including combinations of digital data storage devices (e.g., solid state drives and hard disk drives), optical storage devices, and/or semiconductor memory devices such as Random Access Memory (RAM) devices and Read Only Memory (ROM) devices.

The storage device 630 can store a software program 640 with executable logic for controlling the processor unit 620. The processor unit 620 performs instructions of the software program 640, and thereby operates in accordance with the present invention. The processor unit 620 may also cause the communication device 610 to transmit information, including, in some instances, control commands to operate apparatus to implement the processes described above. The storage device 630 can additionally store related data in a database 650 and database 660, as needed.

Figure 7:
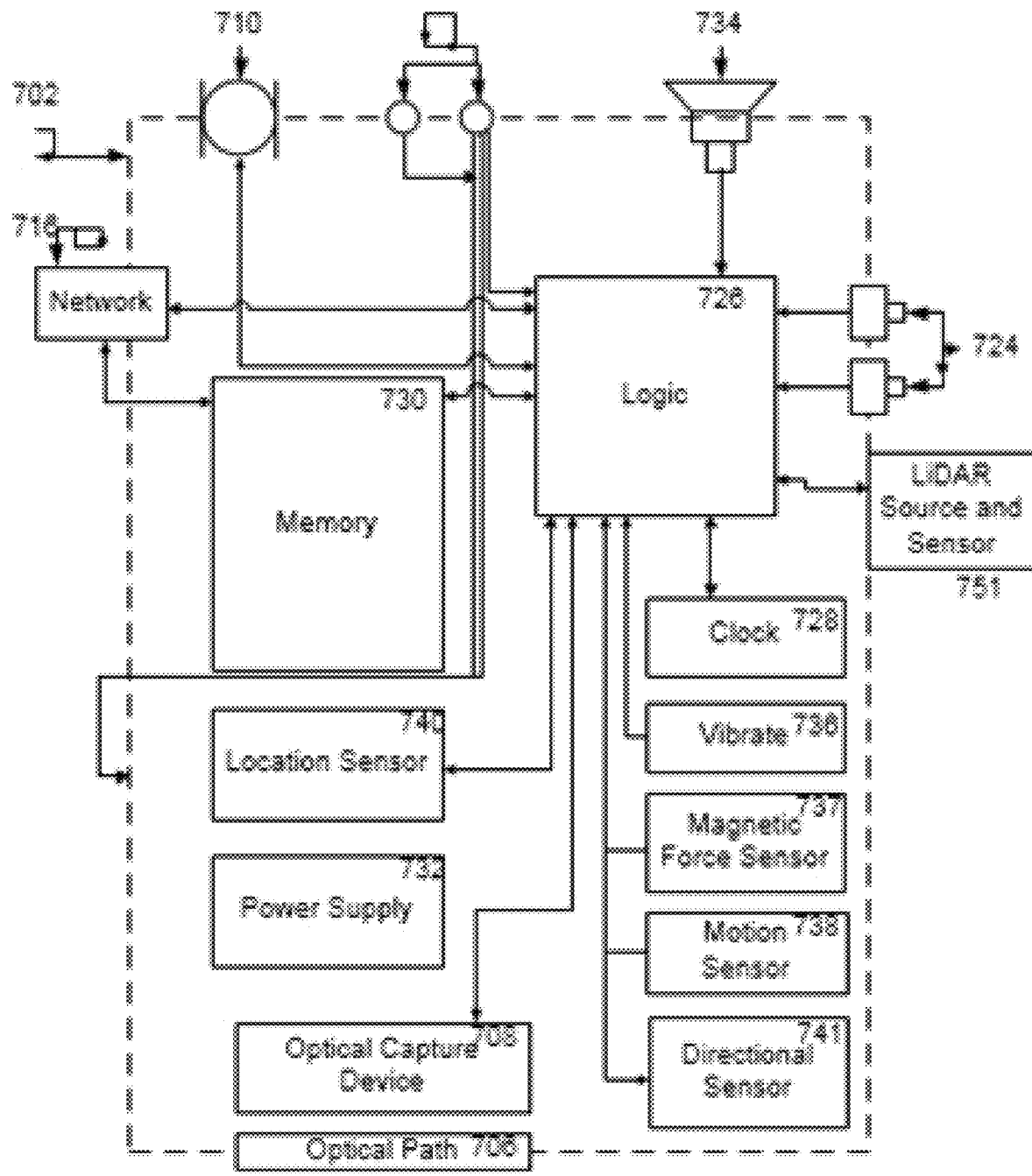
FIG. 7 illustrates an exemplary handheld device that may be used to implement aspects of the present disclosure including executable software.

Referring now to FIG. 7, a block diagram of an exemplary Smart Device 702 is shown. Smart Device 702 comprises an optical capture device 708 to capture an image and convert it to machine-compatible data, and an optical path 706, typically a lens, an aperture or an image conduit to convey the image from the rendered document to the optical capture device 708. The optical capture device 708 may incorporate a CCD, a Complementary Metal Oxide Semiconductor (CMOS) imaging device, or an optical Sensor 724 of another type.

A microphone 710 and associated circuitry may convert the sound of the environment, including spoken words, into machine-compatible signals. Input facilities may exist in the form of buttons, scroll wheels, or other tactile Sensors such as touch-pads. In some embodiments, input facilities may include a touchscreen display.

Visual feedback to the user is possible through a visual display, touchscreen display, or indicator lights. Audible feedback 734 may come from a loudspeaker or other audio transducer. Tactile feedback may come from a vibrate module 736.

A magnetic force sensor 737, such as a Hall Effect Sensor, solid state device, MEMS device or other silicon based or micro-electronic apparatus.

A motion Sensor 738 and associated circuitry converts motion of the Smart Device 702 into a digital value or other machine-compatible signals. The motion Sensor 738 may comprise an accelerometer that may be used to sense measurable physical acceleration, orientation, vibration, and other movements. In some embodiments, motion Sensor 738 may include a gyroscope or other device to sense different motions.

A location Sensor 740 and associated circuitry may be used to determine the location of the device. The location Sensor 740 may detect Global Position System (GPS) radio signals from satellites or may also use assisted GPS where the mobile device may use a cellular network to decrease the time necessary to determine location. In some embodiments, the location Sensor 740 may use radio waves to determine the distance from known radio sources such as cellular towers to determine the location of the Smart Device 702. In some embodiments these radio signals may be used in addition to GPS.

Smart Device 702 comprises logic 726 to interact with the various other components, possibly processing the received signals into different formats and/or interpretations. Logic 726 may be operable to read and write data and program instructions stored in associated storage or memory 730 such as RAM, ROM, flash, SSD, or other suitable memory. It may read a time signal from the clock unit 728. In some embodiments, Smart Device 702 may have an on-board power supply 732. In other embodiments, Smart Device 702 may be powered from a tethered connection to another device or power source.

Smart Device 702 also includes a network interface 716 to communicate data to a network and/or an associated computing device. Network interface 716 may provide two-way data communication. For example, network interface 716 may operate according to the internet protocol. As another example, network interface 716 may be a local area network (LAN) card allowing a data communication connection to a compatible LAN. As another example, network interface 716 may be a cellular antenna and associated circuitry which may allow the mobile device to communicate over standard wireless data communication networks. In some implementations, network interface 716 may include a Universal Serial Bus (USB) to supply power or transmit data. In some embodiments, other wireless links may also be implemented.

As an example of one use of Smart Device 702, a reader may scan some coded information from a location marker in a facility with Smart Device 702. The coded information may include for example, a hash code, bar code, RFID or other data storage device. In some embodiments, the scan may include a bit-mapped image via the optical capture device 708. Logic 726 causes the bit-mapped image to be stored in memory 730 with an associated time-stamp read from the clock unit 728. Logic 726 may also perform optical character recognition (OCR) or other post-scan processing on the bit-mapped image to convert it to text. Logic 726 may optionally extract a signature from the image, for example by performing a convolution-like process to locate repeating occurrences of characters, symbols or objects, and determine the distance or number of other characters, symbols, or objects between these repeated elements. The reader may then upload the bit-mapped image (or text or other signature, if post-scan processing has been performed by logic 726) to an associated computer via network interface 716.

As an example of another use of Smart Device 702, a reader may recite words to create an audio file by using microphone 710 as an acoustic capture port. Logic 726 causes audio file to be stored in memory 730. Logic 726 may also perform voice recognition or other post-scan processing on the audio file to convert it to text. As above, the reader may then upload the audio file (or text produced by post-scan processing performed by logic 726) to an associated computer via network interface 716.

A directional sensor 741 may also be incorporated into Smart Device 702. The directional device may be a compass and be based upon a magnetic reading, or based upon network settings. The magnetic sensor may include three axes of magnetic sensitive elements and may also be coupled with an accelerometer in the directional sensor 741.

A LiDAR sensing system 751 may also be incorporated into Smart Device 702. The LiDAR system may include a scannable laser light (or other collimated) light source which may operate at nonvisible wavelengths such as in the infrared. An associated sensor device, sensitive to the light of emission may be included in the system to record time and strength of returned signal that is reflected off of surfaces in the environment of Smart Device 702. Aspects relating to capturing data with LiDAR and comparing it to a library of stored data (which may be obtained at multiple angles to improve accuracy) are discussed above.

Physical world and virtual-world based imagery related to the environment of a user may be presented via a user interface that may display on a Smart Device screen or other interactive mechanism, or in some embodiments, be presented in an augmented of virtual environment, such as via a VR or AR headset. The imagery displayed upon these devices may represent a composite of image data reflective of a real-world data stream as well as digitally added/superimposed image data from a virtual or digital source data stream. A user may be presented a typical image as it would look to the user's eyes physically, upon which digital shapes representing virtual "Tags" may be superimposed to represent the presence of digital information that may be accessed by a user. In other examples, the digital information may be directly displayed as a superposition. In some examples, the real-world and virtual-world environments may be displayed separately on a screen or separately in time.

In some examples, the "physical world image" may also be digitally formed or altered. For, example, an imaging device may obtain images where the sensing elements of the imaging device are sensitive to a different frequency of electromagnetic radiation, such as in a non-limiting sense infrared radiation. The associated "real-world image" may be a color scale representation of the images obtained in the infrared spectrum. In still further examples, two different real-world images may be superimposed upon each other with or without additional virtual elements. Thus, a sensor image may have an IR sensor image superimposed over part or all of the image and a digital shape representing a virtual Tag may be superimposed.

In some implementations, a virtual reality headset may be worn by a user to provide an immersive experience from a vantage point such that the user may experience a virtual representation of what it would be like to be located at the vantage point within an environment at a specified point in time. The virtual representation may include a combination of simulated imagery, textual data, animations and the like and may be based on scans, image acquisition and other Sensor inputs, as examples. A virtual representation may therefore include a virtual representation of image data via the visual light spectrum, image data representing image scans obtained via infrared light spectrum, noise and vibration reenactment. Although some specific types of exemplary sensor data have been described, the descriptions are not meant to be limiting unless specifically claimed as a limitation and it is within the scope of this disclosure to include a virtual representation based upon other types of captured sensor data may also be included in the AVM virtual reality representation.

It should be noted that although a Smart Device is generally operated by a human Agent, some embodiments of the present disclosure include a controller, accelerometer, data storage medium, Image Capture Device, such as a CCD capture device and/or an infrared capture device being available in an Agent that is an unmanned vehicle, including for example an unmanned ground vehicle ("UGV") such as a unit with wheels or tracks for mobility and a radio control unit for communication. or an unmanned aerial vehicle ("UAV") or other automation.

In some embodiments, multiple unmanned vehicles may capture data in a synchronized fashion to add depth to the image capture and/or a three-dimensional and four-dimensional (over time) aspect to the captured data. In some implementations, UAV position may be contained within a perimeter and the perimeter may have multiple reference points to help each UAV (or other unmanned vehicle) determine a position in relation to static features of a building within which it is operating and also in relation to other unmanned vehicles. Still other aspects include unmanned vehicles that may not only capture data, but also function to perform a task, such as paint a wall, drill a hole, cut along a defined path, or other function. As stated throughout this disclosure, the captured data may be incorporated into a virtual model of a space or Structure.

Referring now to FIGS. 8A-8G, exemplary Wireless Communication Areas (WCA) and Radio Target Areas (RTAs) are illustrated. In general, a WCA is an area through which wireless communication may be completed. A size of a WCA may be dependent upon a specified modality of wireless communication and an environment through which the wireless communication takes place. In this disclosure (and as illustrated), a WCA may be portrayed in a representative spherical shape; however, in a physical environment, a shape of a WCA may be amorphous or of changing shape and more resemble a cloud of thinning density around the edges. In general, a RTA is an area from which an energy-receiving Sensor will receive energy of a type and bandwidth that may be quantified by the energy-receiving Sensor. The RTA shape and size may be affected by an environment through which the energy must be conveyed and further effected by obstructions.

According to the present invention, a WCA and RTA may be used to provide an augmented reality user interface indicating a location of various persons within the WCA and RTA and indications of sensor readings related to those persons as well as links to further information.

Figure 8A:
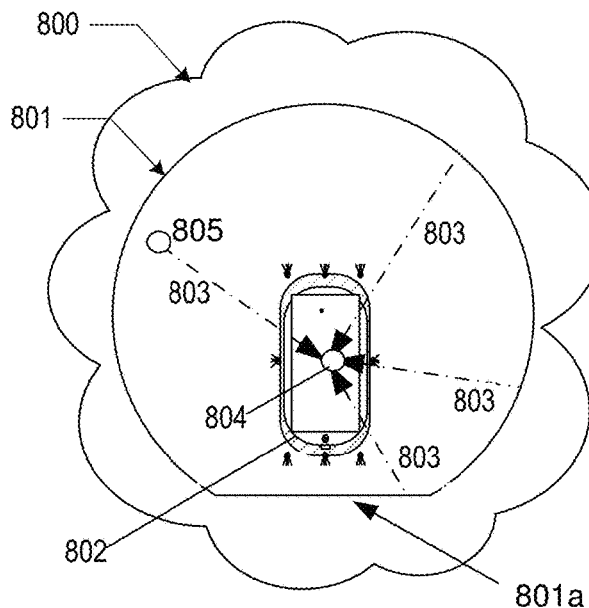
FIGS. 8A-8G illustrate aspects of the determination of directions of interest and Fields of View and information display.

Referring now to FIG. 8A, a side view illustrates a WCA 800 surrounding a Node, such as a Smart Device 802. Energy 803, which is illustrated as rays, is received by one or more energy-receiving Sensors 804 in the Smart Device 802 (energy-receiving Sensors may also be in a Smart Receptacle associated with the Smart Device, though this is not illustrated in FIG. 8A). An exemplary ray 803 proceeds from a position 805 within RTA 801 boundary to the energy-receiving Sensor 804.

As illustrated, a portion 801a of the RTA 801 may flatten out in response to a ground plane, wall, partition, or other obstruction encountered. A Node 806 may be located on or within a surface that makes up a relevant obstruction and the Node 806 may appear to be along a perimeter of the RTA 801. Similarly, a Virtual Tag may be associated with location coordinates that appear on or within a floor, wall, partition, or other article acting as a radio frequency obstruction and thereby appear to be a part of the obstruction, however, since it is virtual, the Virtual Tag will not effect the physical properties of the obstruction. Essentially, a Virtual Tag may have location coordinates that correspond to anywhere in the physical real-world. In some examples, a software limit or setting may limit location coordinates of Virtual Tags to some distance from a base position or a distance from a designated position, such as a location of a designated Physical Tag, Reference Point Transceiver or other definable position.

In addition to obstructions, a topography of an environment within an RTA 801 may also limit wireless conveyance of energy within an RTA 801 to an energy-receiving Sensor 804. Topography artifacts may include, for example, a terrain, buildings, infrastructure, machinery, shelving or other items and/or other structures that may create impediments to the receipt of wireless energy.

Energy received 803 into the energy-receiving Sensor 804 may be used to create aspects of a user interface that is descriptive of the environment within the RTA 801. According to the present invention, environmental aspects, Nodes 806, Tags (both physical Tags and Virtual Tags) and the like may be combined with user interactive mechanisms, such as switches or other control devices built into a user interactive device, and included in a user interactive interface. For example, energy levels received into an energy-receiving Sensor 804 may be combined with location coordinates of Physical Tags and/or Virtual Tags and a user interactive device may be positioned in an interactive user interface at a position correlating with the position coordinates and be surrounded with a visual indicator or the received energy levels.

In this manner, a single user interface will include a static image representative of received energy levels at an instance in time; a visual representation of a location(s) of Physical and/or Virtual Tag(s), and devices with user interactive functionality. In some embodiments, the devices with user interactive functionality may be positioned at a location in the user interactive interface correlating with the position(s) of the Physical and/or Virtual Tag(s).

This disclosure will discuss RTAs 801 that are frustums of a generally conical shape, however, RTAs 801 of other volume shapes are within the scope of the invention. For example, if an energy-receiving Sensor 804 included a receiving surface that was a shape other than round, or had multiple receiving surfaces, each of a round or other shape, the RTA 801 associated with such an energy-receiving Sensor 801 may have a shape other than a frustum of generally conical shape.

Figure 8B:
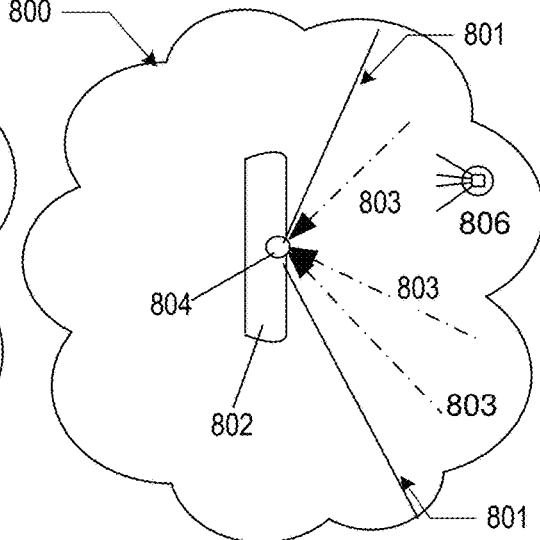

Referring now to FIG. 8B, a top-down view of a RTA 801 is depicted. A RTA 801 will include some portion of a WCA 800. As illustrated, the WCA 800 includes a space with irregular boundaries encompassing 360 degrees around the Smart Device 802. Aspects such as topography, strength of signals and atmospheric conditions (or other medium through which a wireless communication will travel) may affect and/or limit a perimeter of the WCA 800. A location of the RTA 801 may be referenced to determine which Tags (Physical and/or Virtual) such as node 806 are included within an interactive user interface. Generally, preferred embodiments may only include Tags with location coordinates with the RTA 801 in the interactive user interface. However, embodiments may include Tags external to the RTA 801 in a particular interactive user interface.

Figure 8C:
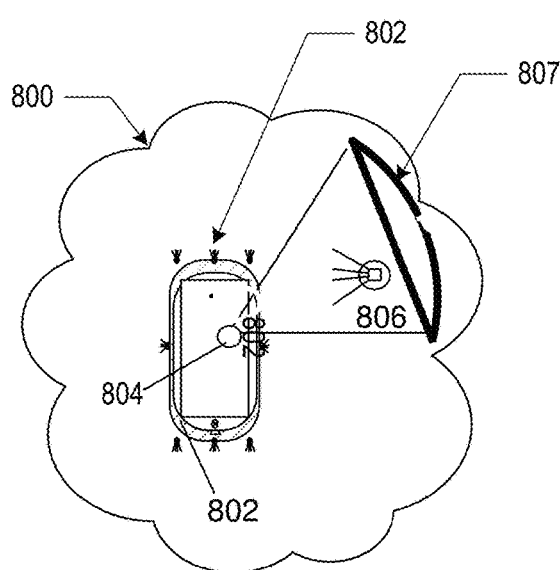

Referring now to FIG. 8C, a side view of a WCA 800 is presented where an energy-receiving Sensor 804 is capable of quantifying a particular form of energy, such as a particular bandwidth of energy received from a user selected RTA 807. A Smart Device 802 may incorporate or be in logical communication with multiple energy receiving devices 804, each energy receiving device capable of quantifying a limited energy spectrum in an environment defined by the RTA 807 selected by the user.

Some embodiments include a RTA 807 that varies according to a type of energy receiving device 804 receiving a corresponding type of energy. For example, an energy-receiving Sensor 804 that receives energy in a lower bandwidth may have an RTA 807 that extends a greater distance than an energy-receiving Sensor 804 that receives energy in a higher bandwidth. Similarly, some energy-receiving Sensors 804 may be effected by forces outside of the RTA 807, such as a magnetometer which may be sensitive to signal interactions around all of the WCA 800, and a RTA 807 associated with a magnetometer may accordingly be the same as the WCA 800.

By way of non-limiting example, a RTA 807 for a CCD-type energy receiver may be represented as a frustum with an expansion angle of approximately 60 degrees in shape. Accordingly, the RTA 807 subtends only a portion of the universal WCA 820.

Figure 8D:
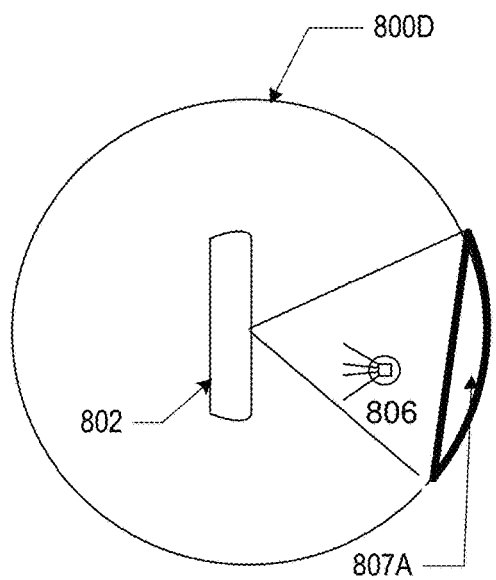

Referring now to FIG. 8D, a top view of a WCA 800D is illustrated with a RTA 807A comprising a frustum with an expansion angle of approximately 60 degrees. A Smart Device with an energy receiver 802 that quantifies a specified bandwidth of energy from the RTA 807A may generate a user interface with an image based upon energy quantified from RTA 807A.

In FIG. 8D, the WCA 800D is represented as a spherical area. A WCA 800D may be designated that is less than an entire area of possible radio communication using a specific designated wireless communication modality. For example, WCA 800D may be spherical and stay within boundaries of a modality based upon a UWB wireless communication protocol.

A user interface based upon quantified energy in an RTA 807, 807A, may present a representation of energy within the respective RTA 807, 807A as quantified by an energy-receiving Sensor 802. Energy levels of other three-dimensional spaces within the WCA 800 may be quantified by energy receivers and presented in a user interface by directing energy from a selected three-dimensional space into the energy receivers and thereby defining a different RTA. In this manner, energy levels may be quantified from essentially any area within the WCA 820 380 and represented as part of a user interface. Quantified energy levels may vary based upon a receiving Sensor. For example, a CCD Sensor may quantify visible light spectrum energy, and a LIDAR receiver a broad spectrum, an infrared receiver may quantify infrared energy levels, and energy-receiving Sensors. A particular feature present in a particular portion of the electromagnetic spectrum quantified by an energy-receiving Sensor may have a unique physical shape which characterizes it and which may be associated with a corresponding virtual-world aspect and Tag associated with the location.

In some examples, as has been described, quantification of energy levels associated with aspects of the physical world may be for one or more of: characterizing an RTA 807, 807A by quantifying energy levels and patterns existing at an instance in time, determining a location and/or orientation of a Smart Device 802 or other Node, such as node 806; and verifying a location and/or orientation of a Smart Device. In some examples, energy levels associated with aspects of the physical world may be communicated by the Smart Device to a remote controller for further processing, and the remote controller may communicate information back to the Smart Device or to another user interface. Information communicated from the controller may include, for example, an orientation of physical and/or virtual aspects located within the universal RTA in relation to the Smart Device; quantified energy indicating of or more of: a topographical feature, a surface temperature, a vibration level, information associated with a Virtual Tag, information associated with a physical Tag, sensor data, or other information associated with the RTA 807A.

A view of a Radio Target Area 807-807A may be a relatively small portion of the entire WCA that surrounds a Smart Device. An area of energy to be quantified by a sensor (sometimes referred to herein as the Radio Target Area) may be displayed surrounded by the WCA 830.

Figure 8E:
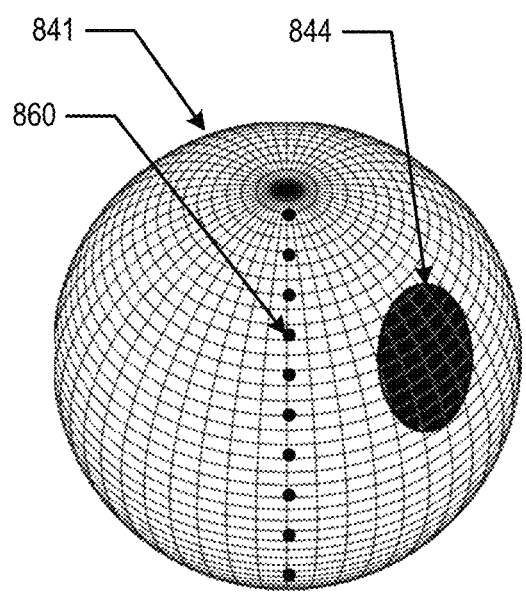

Referring now to FIG. 8E, an exemplary presentation of a RTA 844 superimposed upon a representation of a WCA 841 is illustrated. The WCA 841 is illustrated with a perspective view of a spheroid with an alignment feature 860 such as a spheroid dividing arc, or a line. A blackened ellipsoid feature is a representation of the RTA 844 associated with a particular Smart Device which would be located at a center of the spheroid WCA 841. If desired, one or more energy receiving devices associated with or incorporated into a Smart Device may be repositioned or have a changed orientation in space to ultimately scan all of the accessible universal Radio Target Area space.

Figure 8F:
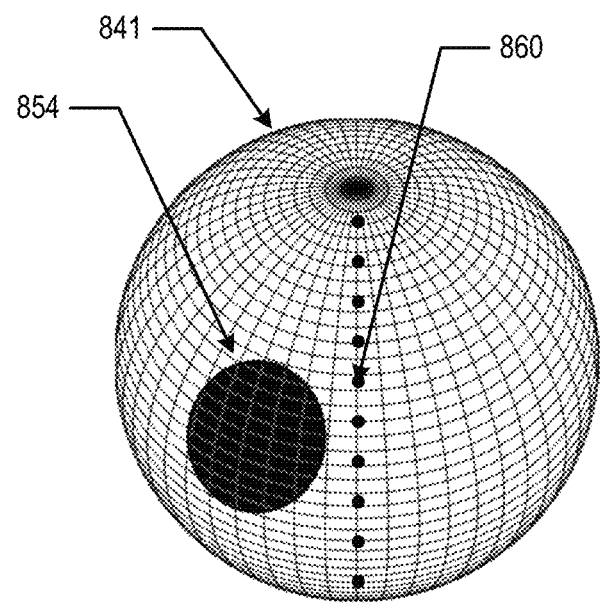

Referring to FIG. 8F, an illustration of how moving the one or more energy receiving devices around in space may alter an area defined as the RTA 854. The same orientation of the universal WCA 841 may be noted by a same location of the alignment feature 860. Relative movement of the ellipsoid feature illustrates a change in an area designated as RTA 854.

Figure 8G:
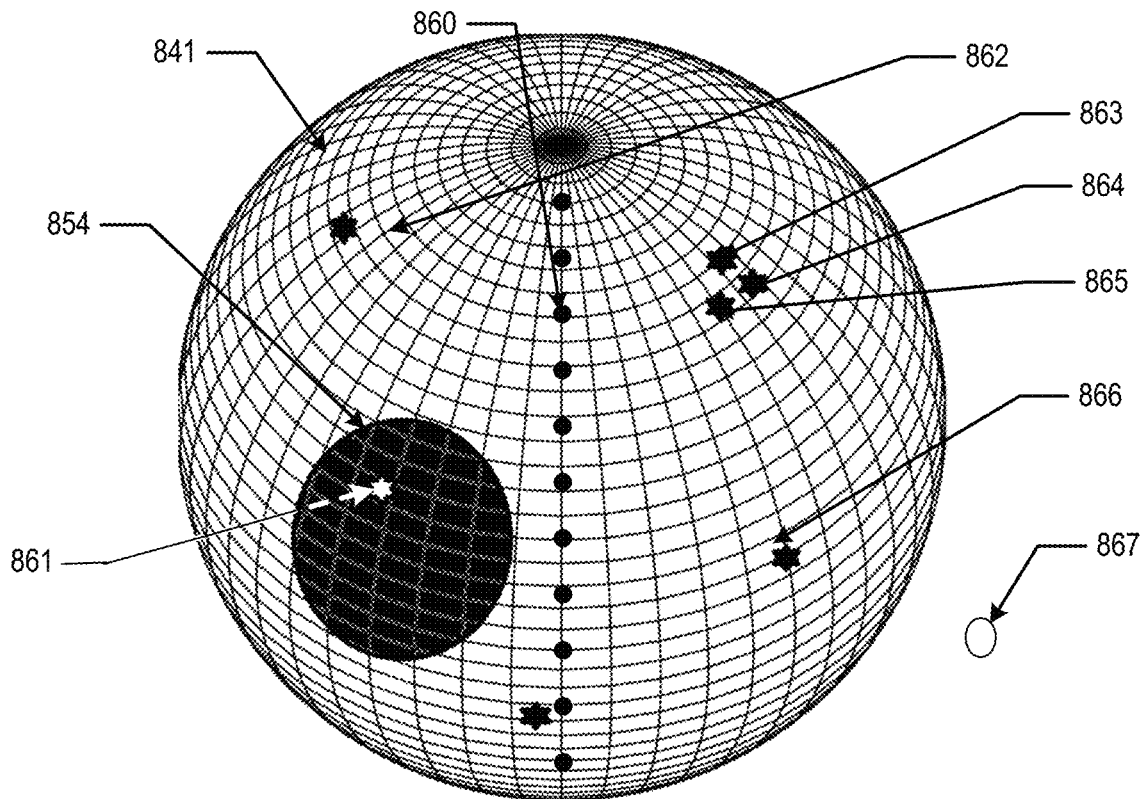

Referring to FIG. 8G, an illustration of adding Tag locations (which may be Physical Tags or Virtual Tags) to a mapping of the WCA 841 is provided. A Tag may be represented in the WCA, for example, as an icon (two- or three-dimensional) positioned in space according to a coordinate system, such as Cartesian coordinates, polar coordinates, spherical coordinates or other mechanism for designating a position. Coordinates may specify one or both of physical real-world Tags and Virtual Tags.

A location of a real-world Tag or Virtual Tag may be in either RTA 861, the WCA 841 or external to both the RTA 861 and the WCA 841. Examples of Tags outside the RTA 861 and within the WCA 841 include Tags 862-866. An example of a Tag in the device RTA is Tag 861. A Tag located external to of the WCA 841 and the RTA 861 includes Tag 867.

In some examples, a display on the user's Smart Device may illustrate image data captured via a CCD included in a Smart Device. Portions of the image data captured via a CCD may be removed and replaced with an icon at position correlating to a position in space within the RTA 861. The icon may indicate of a Tag 861 located within the RTA 861, or at least the direction in the RTA 864 along which the Tag 861 may be located at an instance in time. In addition, an area of a user interface portraying the Icon may user interactive device such that when the device is activated, the Smart Device is operative to perform an action.

The actual positions of the Tags in real-world space (or the digital equivalent in the real-world space) may be stored and maintained in a database. Positions of physical Tags may be determined via techniques based upon wireless communication and be updated periodically. A period of update may be contingent upon variables including, user preference, Tag movement, change in environmental conditions, User query or other variable that may be converted into a programmable command. In another example of some embodiment, an Agent may interact with a user interface and understand the presence of Tags that are outside of the RTA 861 and adjust one or both of a position and direction that the Smart Device to cause the Smart Device to be positioned such that the RTA 861 encompasses a position of the Tag of interest.

Figure 9A:
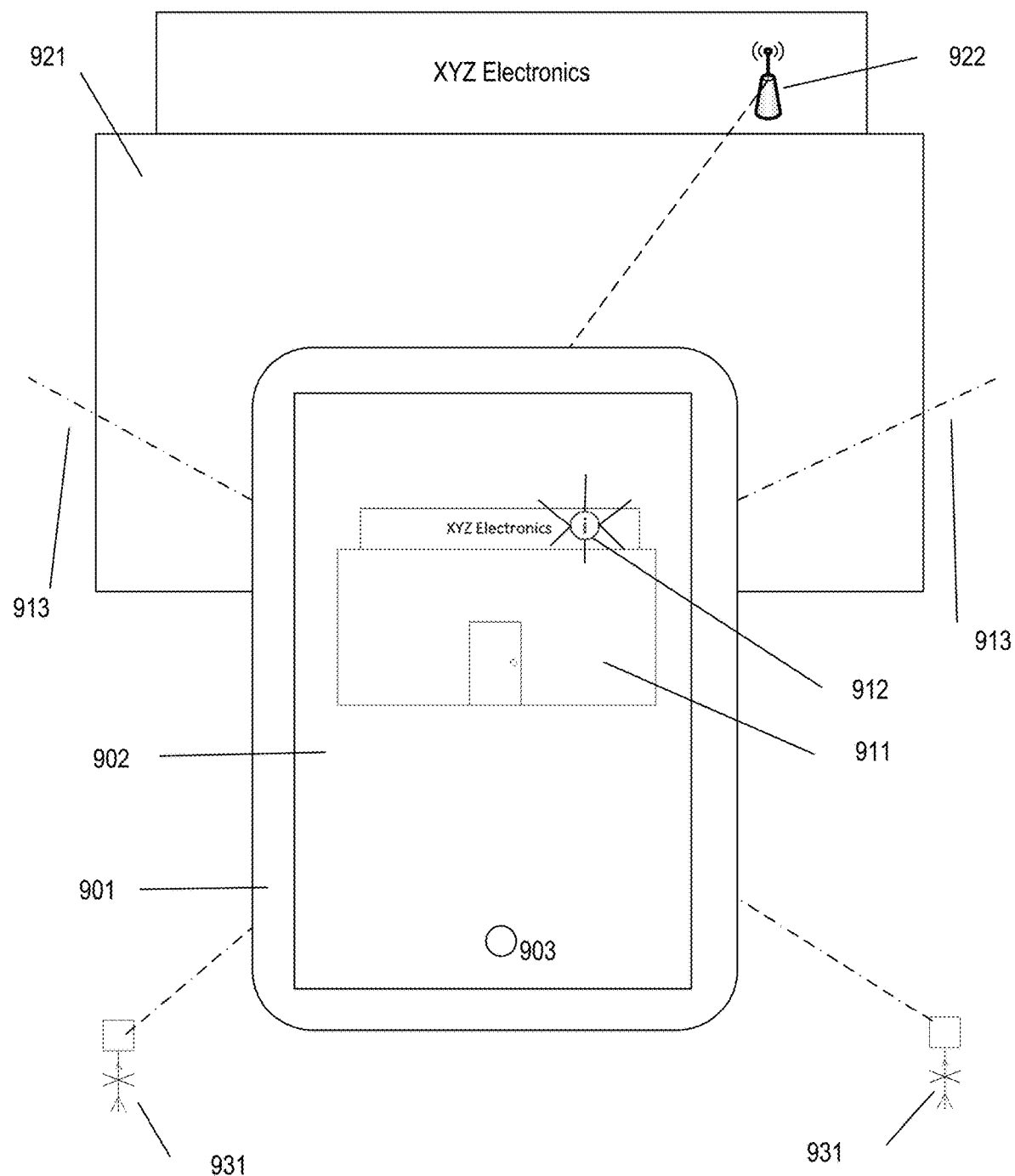
FIGS. 9A-9C illustrate additional aspects of information display.

Referring to illustration FIG. 9A, an exemplary apparatus for effectuating the methods described herein is shown, wherein Smart Device 901 has within its Radio Target Area a Structure 921. Smart Device 901 may display a user interface 902 based upon data generated by an energy-receiving Sensor 903 incorporated into the Smart Device or operative in conjunction with the Smart Device 901. The energy-receiving Sensor 903 may produce data representative of an area from which the energy-receiving Sensor 903 received energy. A user interface 902 may be generated that is based upon relative values of some or all of the data produced by the energy-receiving Sensor 903.

Smart Device 901 may have its position and direction determined using the orienteering methods described herein, with reference to Reference Point Transceiver 931. The position may be determined relative to a Base Node, which may operate as an origin in a coordinate system associated with Structure 921 and its surroundings. The position-determination step may be aided with reference to transmitter 922, which in some embodiments, may be a Reference Point Transceiver. In this example, transmitter 922 is positioned proximate to the Structure 921.

A receiver on Smart Device 901 may be operative to receive a wireless logical communication from transmitter 922. This communication may be in one of a variety of modalities, such as Bluetooth, ultra-wideband, radiofrequency, etc. Based upon the signal, Smart Device 901 may transmit to a server, a database query based upon a determined set of coordinates of transmitter 922.

If the database contains an entry comprising, as a data structure, a set of coordinates proximate to the set of coordinates of transmitter 922, then Smart Device display 902 may display icon 912 proximate to the location of transmitter 922, as displayed on Smart Device display 902, or otherwise on the virtual representation of the shop 911. In this way, a user of Smart Device 901 may be alerted to the presence of information associated with structure 921 in which the user may be interested.

In some embodiments, icon 912 may be displayed on Smart Device display 902 only if Smart Device 901 can transmit appropriate permissions to the database. For example, icon 912 may only display if Smart Device 901 is on a certain Wi-Fi network or if the user of Smart Device 901 has input the appropriate credentials. In other embodiments, icon 912 may display on any Smart Device display 902 (if the Radio Target Area Cone 913 includes transmitter 922), but further functionality may be based upon inputting a password (or, in some embodiments, correctly input the answer to a question).

In some embodiments, the appearance of icon 912 may change based upon an identity of the user or based upon some other dynamic. For example, if the user has a certain UUID, and the database includes a message specifically intended for a user with that UUID, then the icon may flash to indicate the presence of a message. This message may be displayed textually, visually, audibly, or by a hologram. Similarly, the database may record each instance in which it is accessed by a query from a Smart Device. Such a record may include a time stamp. If data related to structure 921 has changed since the last time stamp, then icon 912 may turn red (for example) to indicate such a change. In addition, digital content may be appended to any content already in the database, such as additional alphanumeric annotation, an audio file, an image file, a video file or a story file.

Activation of an interactive user device encompassing icon 912, additional functionality may be provided to the user of the Smart Device 901. For example, selecting icon 912 may display information about Structure 921, such as shop hours or discounts. Alternatively, activating the interactive user device associated with icon 912 may generate a control panel, which may allow the user to control aspects relating to sensors or other electronics within structure 921. For example, upon confirmation that Smart Device 901 has the appropriate permissions, selecting icon 912 may allow the user to turn off the lights within structure 921.

The Smart Device 901 may also display other functional buttons on its display 902. In some examples, one such function may be to show displays of the sensor RTA 913 in the context of the universal Radio Target Area surrounding the user. By activating the functional button, the user may be presented with a set of options to display the universal Radio Target Area.

Figure 9B:
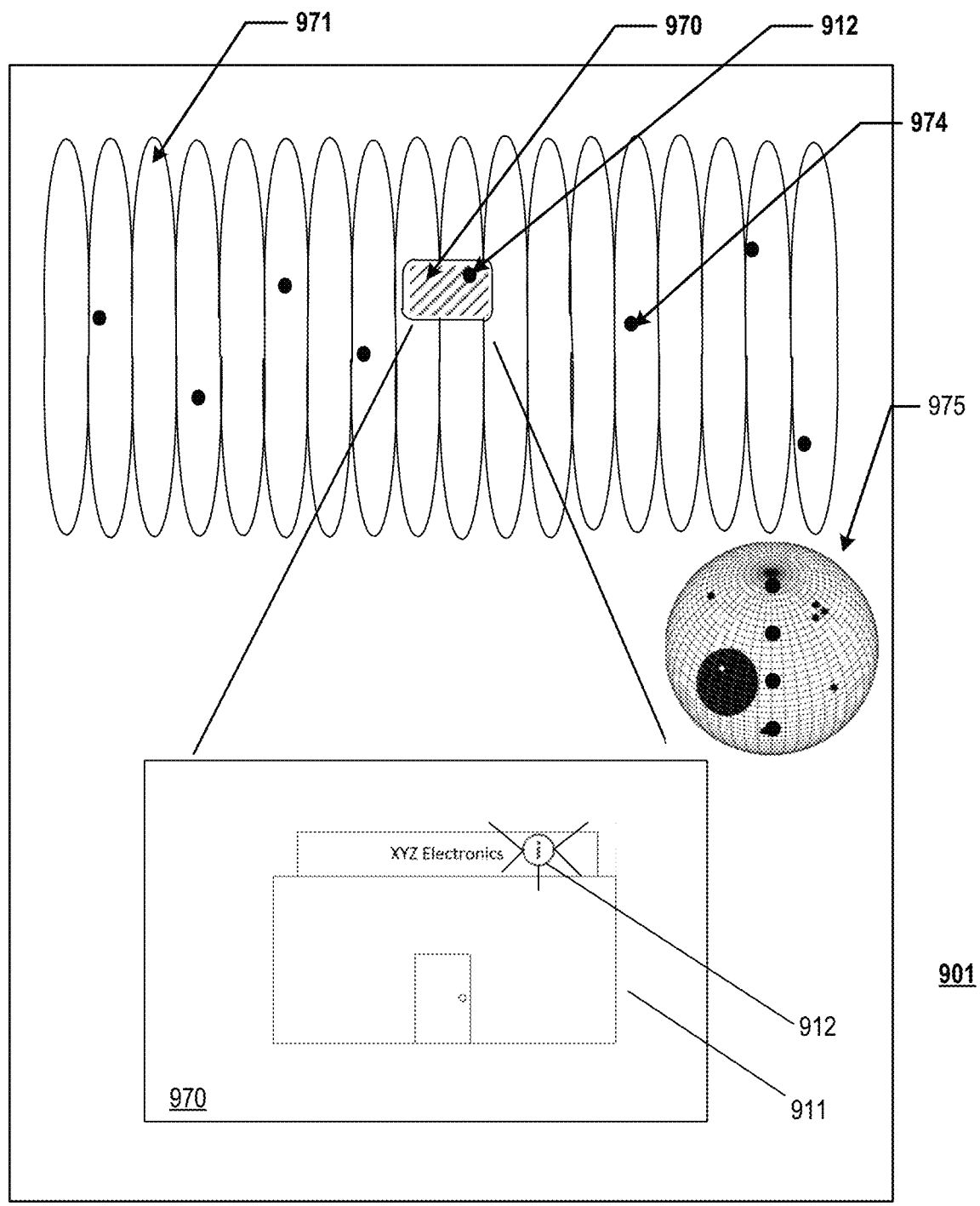

Referring to illustration FIG. 9B, an example of a means of illustrating a RTA 970 is provided. The display screen of the Smart Device 901 may display a number of information components. A similar illustration as FIG. 8G may be included as inset 975. However, a different illustration of the RTA 970 may be formed by flattening the surface of the illustrated sphere into a flat depiction where each of the surface regions may be flattened into a segment 971. The RTA 970 may be illustrated on the flat segments. A Tag or icon 912 may be located within the device RTA 970 showing structure 911. The icon 912 may also be included in the real time display of a representation of data generated by an energy-receiving Sensor. Tags may also be located outside of the RTA 970. An Agent may move around the Smart Device to locate an RTA that encompasses Tag 974.

Figure 9C:
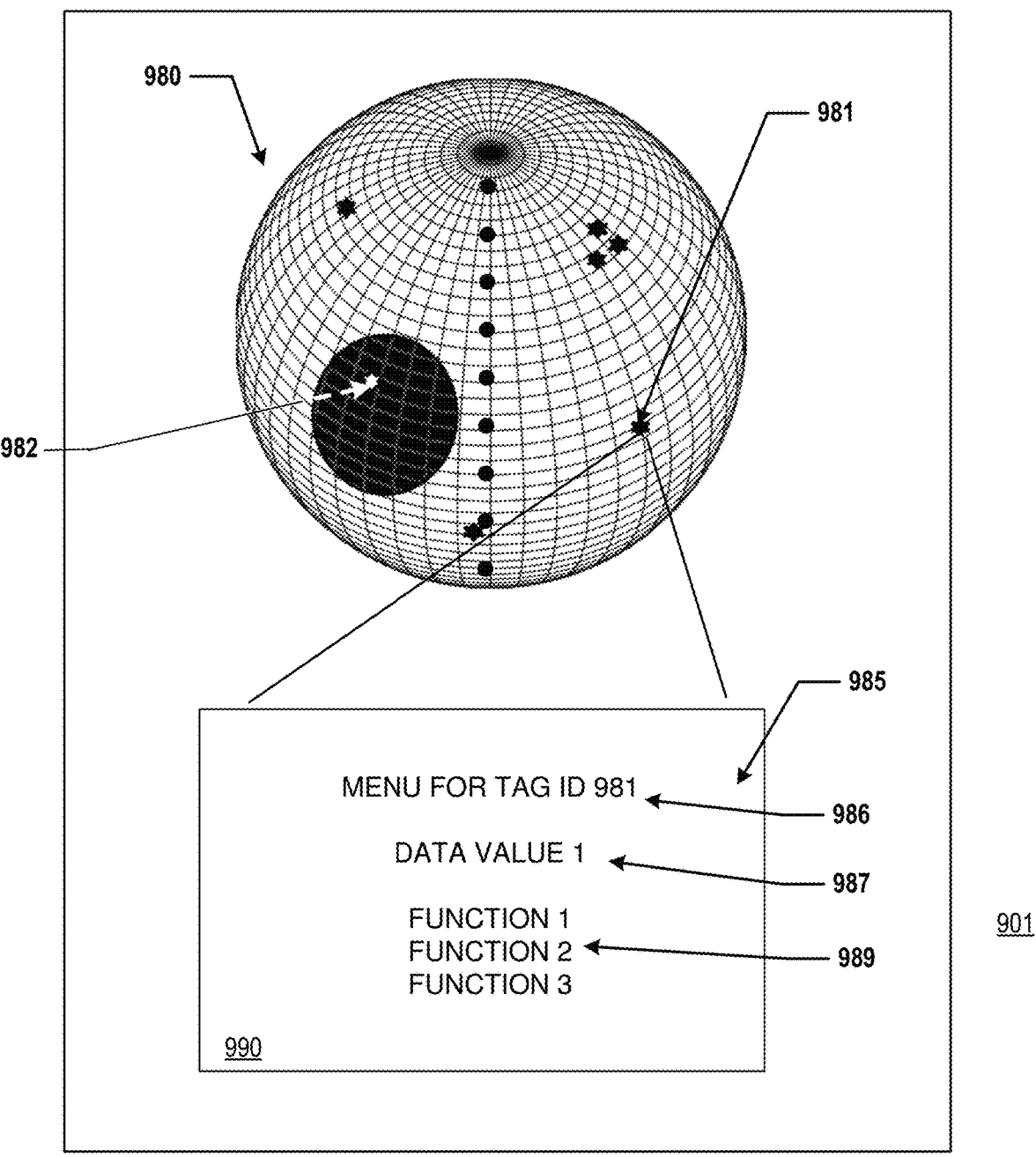

Referring to FIG. 9C, item 980, an exemplary display screen 990 for Smart Device 901 that may be displayed when a user activates a Tag at a location outside the RTA 982 is illustrated. When the user activates the exemplary Tag 981, a menu 985 may display. Amongst the various information such as text, imagery, video content and the like that may be displayed an identification of the Tag 986, associated textual information and data 987 as well as functional buttons 989 may be displayed on the user interface and may be used by the user to activate additional function including new display layers, content integration and control function such as in a non-limiting sense a control to revert to a previous menu display.

In some examples, a Smart Device may function as a Tag. The Tag functionality may include providing location-related information as broadcasted digital content. In providing such broadcasted digital content, the Smart Device tab may employ numerous forms of security protocols for the protection of the information and authorization of its use which may include sign-in/password protocols, sharing of encryption keys and the like. In similar methods, a central server may provide content related to a Tag and may manage security protocols and the like where a Smart Device acting as a Tag may merely share an identification phrase that a user could use with applications running or connecting with the central server could use to be authorized for additional content. Location may be determined by the various means as described herein including wireless communication with position Nodes by GPS, Cellular, Wi-Fi, Ultrawideband, Bluetooth and the like. If the Smart Device is operating in a mesh Node, the mesh could communicate within Nodes relative and absolute location information which the Smart Device may share as its role as a Tag. In addition to location, other sensor data at the Smart Device such as temperature, vibration, sensor imagery, LiDAR scan imagery, sound sensing.

In addition to real-world data, the Smart Device Tag may also provide virtual content associated with itself and its connected environment. The Smart Device may provide content stored within its memory devices and may provide dynamically calculated results of processing on content stored in its memory devices. The virtual content may also correspond to a user interface of the Smart Device Tag that may be used to initiate or authorize function of the Smart Device including real-world activities such a communication via internet protocol, text, phone, or video.

In some embodiments, an energy-receiving Sensor may receive energy associated with a LiDAR transmission and/or other functionality involved in LiDAR scanning which can be used to interrogate the local environment for physical shapes. In a Smart Device Tag function, the Smart Device may stream its video and scanning data directly or through a server model. Some Smart Devices may be configured to operate as a smart security monitoring systems and may provide the video, topographic, audio, and other sensor streams as Tag related content. There may be numerous manners that a Smart Device could function as a Tag in an environment.

A Smart Device with either a single- or multiple-sensor system may also have a LiDAR scanning capability or other three-dimensional scanning capability. The Smart Device may utilize a number of systems to refine and improve its accuracy in determining the location that it is at. In an example, a Smart Device may utilize a GPS or cellular system to get an approximate location of the device. In a next step, a user may initiate the Smart Device to take a series of image and scanning data acquisitions of its environment. For example, the user may move the phone by hand to different directions while maintaining their feet in a fixed location. The phone may use one of the orientation methods as have been discussed to determine its orientation as it is moved to different vantage points. The Smart Device may either process those images and compare against a database in its memory, or it may communicate the data to a server to do the comparison. With an approximate location, the orientation information, and the streams of video and/or topographic information, a calculation may be performed to match the image/topographic information to a more exact positional location. In alternative examples, the device may use the image and/or topographic information to determine the orientation of the device itself.

In some examples, the Smart Device may act as a receiver of one or multiple types of wireless energy input. For example, the acquisition of data based upon a visual light spectrum (approximately 380 to 700 nm wavelength) may be modelled as spatially-characterized electromagnetic energy. Electromagnetic energy in the visible band may enter a focusing lens and be focused up an array of devices. The devices may be CMOS-active pixel sensors, CMOS back-illuminated sensors, or CCDs, as non-limiting examples, to receive the energy and convert it into spatially-arrayed pixel data.

In some examples, the Smart Device may have an energy-receiving Sensor incorporated or attached which may quantify energy levels for frequencies outside the visible spectrum. Any optics employed in such sensors may be different from the previously discussed CMOS and CCD Sensors since some of those energy receiving devices may have filters or lenses that absorb wavelengths outside of the visible spectrum. Sensors with infrared capabilities may have specialized optics and may use different materials for the CMOS and CCD elements—such as indium gallium arsenide-based sensors for wavelengths in the regime of 0.7-2.5 μm.

Alternatively, entirely different sensing elements, such as bolometers, which sense temperature differences of the incoming radiation, may be employed for longer wavelengths in the regime of 7-14 μm and may include filters that remove other wavelengths. A display of an infrared Sensor, which senses incoming energy in the infrared band, may be rendered on a typical visual display, but the colors of such displays may have no direct physical meaning. Instead, a color scheme may be instituted to represent different infrared wavelengths with different visible colors. Alternatively, the colors may be used to represent different intensities of infrared energy received across bands of infrared wavelengths.

In some examples, a Smart Device may both project and receive energy. For example, a Smart Device may scan the topography of its surroundings by use of LiDAR. In LiDAR a laser may be used to emit energy into the environment. The energy may be emitted as pulses or continuous trains, and the light source may be scanned across the environment. Light emitted from the Smart Device may proceed into the environment until it is absorbed or reflected. When it is reflected and subsequently received at the Sensor, the transit time can be converted to distance measurements of the environment. Many different wavelengths of light may be used to scan an environment, but numerous factors may favor certain choices such as invisibility to human/animal eyes, safety, absorption by the airspace surrounding the user and the like. Atmospheric gases may absorb significant amounts of infrared transmissions at certain frequencies; therefore, for LiDAR to be effective in the infrared spectral region, certain bands of emitted frequencies may be favored. A standard LiDAR system may operate at a band from 900-1100 nm infrared wavelength or at a band centered at approximately 1550 nm. As discussed previously, select optic components and materials may be useful for these wavelengths and the detectors may have improved function based on materials such as "black" silicon, germanium, indium phosphide, gallium arsenide, and indium gallium arsenide as exemplary detector materials.

In an example, a laser light source may be rastered across a dimension of forward looking positions of a Smart Device, which may be represented by a conic section or Radio Target Area in front of the Smart Device. As the light is raster across the surface it can address, it may be pulsed on or off. As the light travels out along a collimated path, it may interact with a surface and a portion of the intensity may be reflected backwards.

A resulting reflected ray may come back to the Smart Device and be received by a Sensor in the device. Since the emitted light source may be orders of magnitude more intense than the surroundings, reflected light may dominate a background intensity and the signal detected may be compared with the time of the leading edge of the laser pulse. The repeated acquisition of the timing signals in the various directions can be used to form a point cloud that represents the distance to reflective features from the Smart Device.

As mentioned previously sound may be reflected off of surfaces and the transit time may be used to characterize a distance between a focused ultrasonic transducer and a reflective surface. In similar manners, points or lines of focused sound emissions may be pulsed at the environment and a sensor or array of sensors may detect the reflected signals and feed the result to a controller which may calculate point cloud representation or other or topographic line representations of the measured surface topography. In some examples, ultrasonic focused and scanned soundwaves in the frequency range of hundreds of megahertz may result in small focused sources whose reflections may be detected by magnetic or piezoelectric sound transducers as non-limiting examples.

A Smart Device may have numerous different types of energy-collection devices which may characterize data values with spatial relevance. As mentioned before, infrared imaging may be performed on some Smart Devices, and a user may desire to view a spatial representation of the infrared imaging that represents the data as it may appear if the user's eyes could perceive the energy. In some examples, data values for the wireless energy sensing of infrared energy may be assigned color values and displayed in an image format. For examples, low levels of infrared energy, which may relate to colder temperatures in the imaged regions, may be assigned blue color values, and high levels of infrared energy, which may relate to warmer temperatures, may be assigned red color values. Other color assignments to data values may be used. A legend for the conversion of the color values to the data values may be provided.

In some examples, the data descriptive of spatially descriptive energy levels quantified by an energy-receiving Sensor data may be portrayed in a user interface. In some user interfaces, representations based upon spatially representative energy levels of different wavelengths may be aggregated or otherwise combined in one or more related user interfaces. Such a combination may allow a user to understand the regional nature of various quantified energy.

In some examples, a user interface may allow for display of the positional location image points. In some examples, a location of a pixel element chosen by a user may be converted to a real-world location within the RTA which may be represented in Cartesian coordinates (X,Y,Z) or in other coordinate systems such as polar coordinate systems involving angles and distances as discussed previously. In some examples, topographic data obtained by scanning an area with a RTA may be used quantify topography within the RTA. A user interface based upon such quantified energy levels may include virtual presentations of the quantified energy levels from different perspectives and may allow for coordinate grids (Cartesian or other) to coordinate placement of facets of a user interface based upon combinations of energy level data, Tag locations and perspective relevance.

In some examples, distinct structures within the RTA may be highlighted and assigned positional coordinates. In some examples, this may occur by image processing directly, in other examples a user interface may allow for a user to pick items/regions of interest in a RTA presentation.

In other examples, real and virtual Tags may exist within the RTA. A physical Tag may include a position Node, another Smart Device, or any device with communication capability that can communicate with either a position Node or with the Smart Device of the user directly. Such physical Tags may be located in numerous manners. In some examples, the physical Tag may have a direct determination of its location either because it is stationary and has been programmed with its location or because it has the capability of determining its own position with the various methods as have been described herein. In other examples, a physical Tag may be able to communicate with Nodes such as Reference Point Transceivers and a location may be determined based upon an exchange of data, such as timing values, in the wireless communications. A Node may also be functional to determine, store and communicate a location of other Tags. The Smart Device of the user may gain access to the locations of Tags, either because they are publicly available or because the user has established rights digitally to obtain the information from some or all of these physical Tags.

There may also be virtual Tags that are associated with positional coordinates. The distinction of these Tags over physical Tags is that there may be no physical presence to the virtual Tag. It may be a digital or virtual-world entity that has an association with a real-world positional coordinate. Except for this distinction, a virtual Tag and a real-world Tag may behave similarly with respect to their association with a physical coordinate.

In these examples, an interactive user interface based upon energy levels and Tags located with a RTA may have icons associated with the placement of Tags. The user interface may include an icon positional designation and a graphic to indicate the presence of a Tag. It may be apparent that, in some cases, multiple Tags may lay along a single direction from a given Smart Device location and RTA, and thus multiple icons may be included within a user interface in close proximity. The user interface may indicate multiple Tag icons by color changes, blinking or other indicators. As a RTA is changed, Tags along a same perspective may resolve into different directions for Tags with different positional coordinates.

The Tag icon may indicate to the user a digital functionality associated with a real-world or virtual Tag. For example, the icon may allow a user to choose the functionality of the icon by moving a cursor over the icon and making a keystroke or mouse click or for touch screens by pressing the display location of the Tag icon. The choosing of the Tag icon may activate user interface dialogs to allow the user to control subsequent functionality. In cases of superimposed Tag icons on a same pixel location in a user display, a first functionality may allow the user to choose one of the multiple Tag icons to interact with. In some examples, a Tag icon may be displayed with an associated ID/name and a user may select the icon with voice commands rather than physically selecting the icon as described previously. Displays of these Tags may follow similar protocols as have been discussed in reference to FIGS. 9A-9D.

Referring now to FIG. 10A, a method for generating an augmented-reality Radio Target Area for a Smart Device is shown. At step 1001, wireless energy of a first wavelength is received into a wireless receiver. In exemplary embodiments, this step may include receiving image data based on visible light into a sensor of the Smart Device. The wireless energy may be dispersed over a one-, two-, or three-dimensional space in a defined physical area, and may be received into a one-, two-, or three-dimensional array in the receiver. The wireless energy may take the form of electromagnetic radiation, such as light in the human-visible light spectrum (generally having a wavelength between 380 nm-740 nm), ultraviolet light (generally having a wavelength between 10.0 nm-400 nm), or infrared light (generally having a wavelength between 740 nm-2.00 mm) as examples. The set of wireless energy available to the wireless receiver is the Smart Device's Radio Target Area.

The wireless receiver may be a Smart Device sensor, including a CMOS active pixel sensor, a CMOS back illuminated sensors, CCD, or a LIDAR apparatus, including a solid-state/MEMS-based LIDAR. The wireless receiver may comprise an array or other plurality of other wireless receivers. The wireless receiver may be operative to receive the wireless energy into an array of an appropriate dimension for subsequent display (possibly after processing) on the Smart Device. For example, where the wireless receiver is a Sensor, the Sensor may be operative to translate the wireless energy into a two-dimensional array.

At step 1002, a pattern of digital values is generated based upon receipt of wireless energy into the wireless receiver. This pattern of digital values may be based on one or more qualities of the received wireless energy, including its intensity, spatial dispersion, wavelength, or angle of arrival. The pattern may be placed into an appropriate array. For example, if the display of the Smart Device is a two-dimensional display, then the pattern of digital values may comprise a two-dimensional representation of the image data received. In some embodiments, the pattern of digital values may be based on an aggregated set of values from an array of receivers. For example, if the basis of the digital values is the intensity of the wireless energy received into the receiver, then the digital value assigned to a given entry in the array may be based on a weighted average of intensity of wireless energy received at a plurality of the receivers in the array. Optionally, at step 1003, the wireless receiver may receive the wireless energy as an analog signal (for example, if the wireless receiver is a black-and-white sensor or an unfiltered CCD), and convert the analog signal to digital values through filtration or other analog-to-digital conversion. The set of digital values within the Radio Target Area is the Digital Radio Target Area.

With the Smart Device wireless receiver's Radio Target Area determined, the Smart Device's position should be determined as well, along with the positions of any items of interest in a given space. Collectively, the Smart Device and the item of interest may comprise wireless Nodes. Accordingly, at step 1004, coordinates representative of a wireless Node may be determined relative to a base Node. These coordinates may be determined in any appropriate coordinate system (such as Cartesian, polar, spherical polar, or cylindrical polar) and may be determined via RTLS or the orienteering-triangulation methods with various wavelengths or modalities, such as ultra-wideband, Bluetooth, etc. Additionally, the coordinates may be determined using an angle of arrival or angle of departure of a signal to or from the base Node, along with the distance from the base Node. By way of non-limiting example, this could produce a dataset that correlates the coordinates of three elements with the identities of those elements: {(0,0,0), BaseNode; (1,1,1), SmartDevice; (2,2,2), ItemOfInterest}. While this example may be used throughout the following discussion, it is understood to be non-limiting, as a given space may include a plurality of items of interest. Note that, in some embodiments, the Smart Device itself may become a dynamic database entry with a continuously (or periodically) updating set of coordinates. This may be useful in allowing a plurality of Smart Devices engaged with the system at the same time to interact with one another.

At step 1005, the position of the Base Node is determined relative to the defined physical area. In exemplary embodiments, this may include establishing the Base Node as an origin in the coordinate system and determining vectors from the Base Node to boundaries and items of interest (i.e., the distance from the Base Node and the direction from the Base Node to the boundaries and items of interest). In some examples, the Base Node may have an established reference relative to a global coordinate system established.

At step 1006, a Target Area is generated within a controller of the Smart Device. The Target Area may be the set of coordinates (relative to the Base Node) within the Radio Target Area of the wireless receiver. The Target Area may be limited by physical boundaries of the given space, such as walls, floors, ceilings, occlusions, etc. The Target Area may also be limited by distances that various types of signals may travel. For example, a sensor of audio signals may not be able to practically pickup signals over a background noise level that originate more than 1000 feet from a user position, purely as an example. In such a case, the Target Area for such signal types may be limited to that dimension.

At step 1007, respective positions of one or more wireless Nodes within the Target Area are determined. These positions may be determined relative to the physical Target Area or the Radio Target Area. The determination may be made with reference to the dataset discussed at step 1005, or it may be made dynamically based upon one or more Base Nodes and/or the Radio Target Area. Moreover, the determination may additionally be based on receipt of a wireless signal into the Smart Device from the wireless Node. This signal may indicate a position using the orienteering methods described herein.

At step 1008, a user interface may be generated on the Smart Device based upon the pattern of digital values generated at step 1002. The user interface may comprise a plurality of pixels, wherein each pixel comprises a visible color based upon the pattern of digital values generated at step 1002. For example, if the digital values were based upon receipt of visible light into the wireless receiver (e.g., a sensor), then the display may reflect a reasonably accurate color photograph of the Radio Target Area of the wireless receiver. If the digital values were based upon an intensity of received light from, for example, LIDAR, then the display may reflect a scan of the Radio Target Area. In some embodiments, the pixel may include an intensity of energy received into the receiver. In this way, aspects of the Radio Target Area characterized by an intensity of energy may be emphasized. For example, this may produce a LIDAR relief of an area or a heatmap of an area.

At step 1009, an icon may be generated in the user interface. Preferably the icon will be placed at a position relative to data quantifying received energy levels. In some embodiments, the icon location in a user interface will be indicative of a position of a Tag (Virtual or Physical). This position may be quantified via positional coordinates, such as Cartesian Coordinates, Polar Coordinates, Spherical Coordinates and the like. The icon may be based upon an input from a user, stored data, quantified environmental conditions or other criteria related to an aspect of the Radio Target Area.

For example, an icon may indicate information about an Item of Interest located at a given set of coordinates within the Radio Target Area or Digital Radio Target Area. In another embodiment, the user may indicate on the display a position in which the user wishes to place an icon and add information about an Item of Interest (thus creating a new entry in the database, which may be populated with the coordinates of the indicated position). Moreover, the icon may change colors based upon the pattern of digital values. The icon may be overlaid on top of the display. The icon may resemble the letter "i", a question mark, a thumbnail, or any other suitable image from a library. In some embodiments, the icon may change depending on one or more attributes of its corresponding database entry. For example, if the icon located at (4,4,4) relates to a restaurant menu, then the icon may resemble the letter "i" or a thumbnail of a menu. On the other hand, if this database entry is modified so that the corresponding database entry is a message, then the icon may update to a picture of an envelope.

In some embodiments, the icon-generation step may be based upon an inquiry to a database that uses the Digital Radio Target Area as an input. For example, upon generation of the Digital Radio Target Area, an associated set of coordinates in one or more dimensions may be generated. This may then be submitted to a database. An associated display may be as illustrated in FIG. 9A. In some embodiments, the icon-generation step may be based upon an inquiry to a database that uses the user's position coordinates as an input. In these embodiments, both the Digital Radio Target Area based on a RTA as well as the universal Radio Target Area may be included in an inquiry submitted to the database. An associated display may be as illustrated in FIG. 9C. In some examples, the user may have an option to limit or filter the types of database entries that may be queried for, such as in a non-limiting sense, the existence of real-world Tags, virtual Tags, sensor data values and streams from a particular class of sensors and the like.

Continuing with the example from step 1004, the Digital Radio Target Area may comprise the set of coordinates: ([1.5,10], [1.5,10], [1.5,10]). In this example, the database may return information about the Item of Interest, but not about the Base Node. The Digital Radio Target Area may update when the Smart Device position changes, or by user input, the Digital Radio Target Area may remain static after a certain instance in time.

Figure 10B:
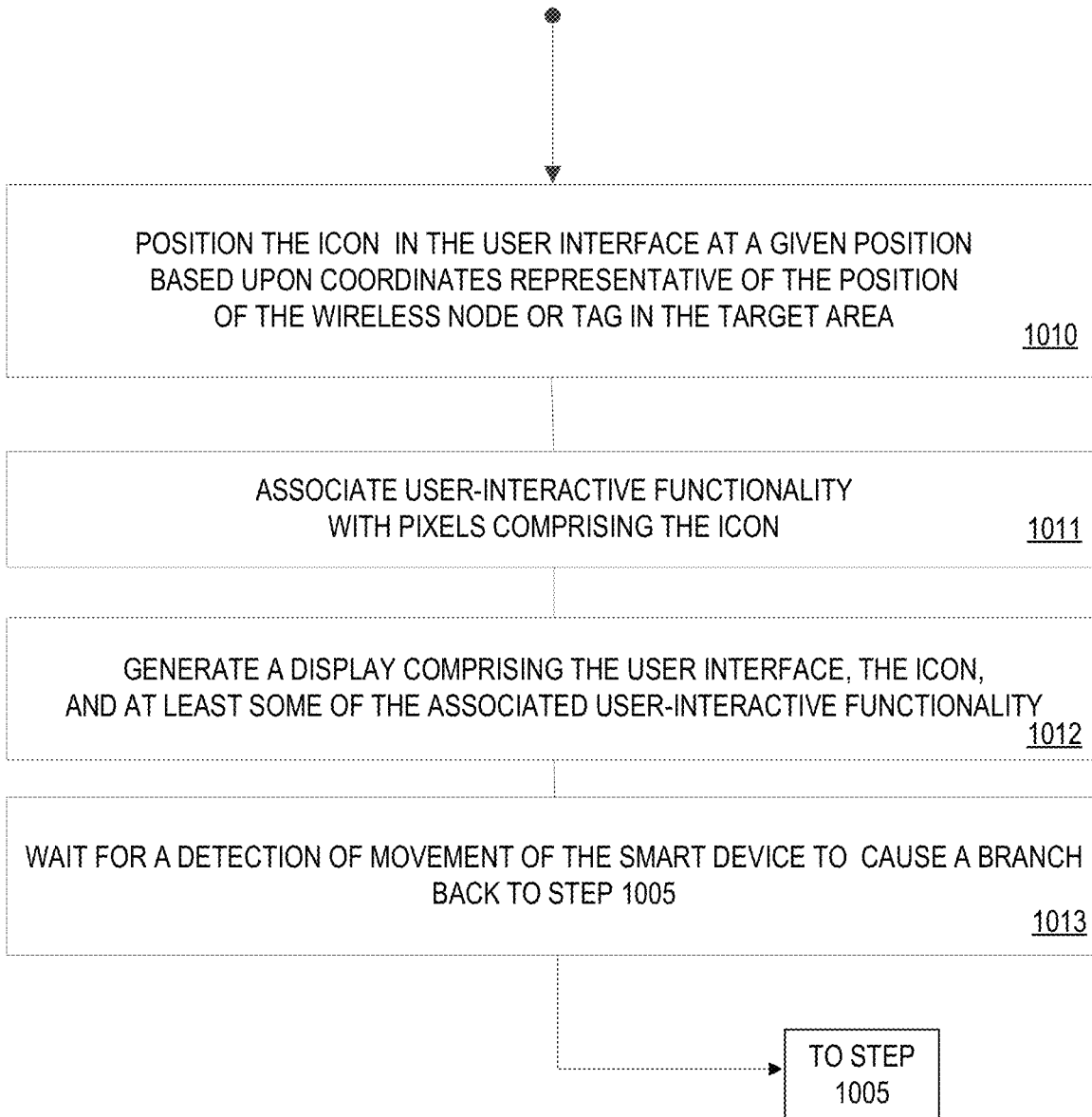

Continuing with FIG. 10B, at step 1010, the icon may be positioned in the user interface at a given position based upon coordinates representative of the position of the wireless Node or Tag in the Target Area. This may comprise a selection of a multitude of pixels related to the position of the wireless Node or Tag, and changing those pixels from the digital values determined at step 1002 to a second set of pixels to indicate the presence of an icon. In some embodiments, the icon may be dynamically updated based upon movement of the Smart Device (and, accordingly, the wireless receiver). In some embodiments, the icon may be permanently associated with a set of coordinates. In such embodiments, the icon may be generated whenever a Smart Device with appropriate permissions includes in its Radio Target Area the set of coordinates of Nodes or Tags associated with the icon.

At step 1011, user-interactive functionality may be associated with the pixels comprising the icon. This may allow the user to "select" the icon by means of an input device (e.g., mouse, touchpad, keyboard), touchscreen, digital input, etc. Upon selection, the icon may be operative to interact with the user in one or more ways, including: displaying a message intended for the user (by text, audio, video, hologram, etc.); requesting credentials from the user to verify permissions (e.g., a password), displaying information about an item associated with the icon, prompting the user to update information about an item associated with the icon, etc. The user-interactive functionality may display static information (e.g., dimensions of the item), display dynamic information (e.g., an alarm state or sensor information relating to the item; for example, if the item is a refrigerator, internal temperature may be displayed), or produce a control panel that allows the user to issue control commands (e.g., remotely operating an automated apparatus by resetting an alarm state, taking remedial action based upon a sensor state as described herein, etc.) or to issue menu control commands such as to invoke a different user interface or screen of a user interface.

This may be useful in geospatial applications, or in procedurally generated activities. For example, a first user may generate a positional designation on a user interactive device, such as, for example an augmented-reality display to leave a narrative, icon or other input associated with the first use. Additionally, the same or another user may log positional coordinates and upload an image that could be displayed submitting a database query including those coordinates. Entry of the coordinates and essential credentials may provide access to the content associated with the positional coordinates.

At step 1012, the preceding steps may be integrated by generating a display comprising the user interface, the icon, and at least some of the associated user-interactive functionality. In embodiments, in which a plurality of Smart Devices are themselves part of the database, this may allow various users to send messages, images, etc. to each other.

At step 1013, detection of movement of the Smart device may cause a branch back to step 1005. Based upon that movement of the Smart Device, a defined physical area from which wireless energy is received (i.e., the Radio Target Area based upon the Target Area) may be changed. The movement may be detected using input from wireless communications, magnetic field sensors, an accelerometer, feature-recognition software, or other similar apparatus and algorithms. In other examples, the position of the Smart Device may be dynamically obtained using any of the techniques of position determination, such as triangulation with reference nodes. Here, too, a change of position detected in this manner may cause a branch back to step 1005. The Target Area may be based upon the position of the Base Node, the relative positions of the wireless Nodes, and the Smart Device.

Figure 11:
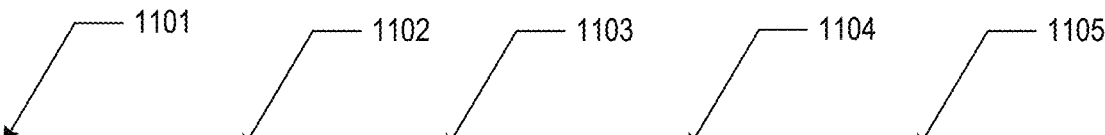
FIG. 11 illustrates an exemplary database structure according to the instant specification.

Referring now to FIG. 11, an exemplary database structure usable in conjunction with the present disclosure is shown. In this non-limiting example, the database has five sets of information: coordinates 1101 associated with an action, permissions 1102 associated with the action, the type 1103 of action, attributes 1104 for the action, and notes 1105. The example shown in FIG. 11 may suppose the following: the augmented-reality system is deployed in an enclosed space, definable by a coordinate system set relative to a Base Node having an origin point (0,0,0); the enclosed space spans, in that coordinate system, ([0, 10], [0, 10], [0, 10]) (using traditional set notation; in other words, each coordinate can take on any number between 0 and 10, inclusive); and the Radio Target Area is ([1, 10], [1, 10], [1,10]).

The bolded entries in the database shown in FIG. 11 represent the database responses to the query given by the Radio Target Area of the Smart Device; i.e., all entries having a Coordinate value within the Radio Target Area. In some embodiments, the database may sort through all coordinates within the Radio Target Area and then return any entries for which the Smart Device has appropriate permissions. In other embodiments, the database may sort through all entries for which the Smart Device has appropriate permissions and then return any entries with coordinates within the Radio Target Area. The latter approach may be beneficial in circumstances in which there are numerous database entries with varying permissions; for example, if a database has 10,000,000 entries, but a given user might only have access to five of those entries, sorting by permissions first may be more beneficial.

The ActionType variable may include any action for which interactivity with an icon may be desirable. In FIG. 11, the ActionType variables shown include Information, Message, Action, and Directions. Each of these represents functionalities within the scope of this disclosure. For example, Information may relate to information that the Smart Device user may find helpful. Continuing with the shop example from FIG. 9A, Information may include store hours, discounts, reviews, etc. Similarly, Message may be a message to the general public (e.g., an announcement), or a message tailored to a specific user. In the latter case, permissions may operate to ensure that only the specific user (or set of users) may access the Message.

Action may relate to any action that a sensor, electronic device, or other apparatus connected to the database may take. For example, Action may include changing a temperature, measuring a temperature, turning off lights, activating an emergency sprinkler system, opening a door, etc. In some embodiments, prior to taking the Action, a password may be requested as part of the permission check.

Directions may show a user how to navigate (using, in exemplary embodiments, orienteering methods) from the current position to a desired position. For example, upon scanning an entry on a map, virtual arrows may be generated to guide the user to a chosen store.

The ActionAttributes may have attributes based on the ActionType. For example, if the ActionType is Information or Message, then the ActionAttributes may be a text string or a stored audiovisual file containing the message. Similarly, if the ActionType requires a sensor or other electronic device to take an Action, then the ActionAttributes may include a command or subroutine to effect such an Action. In the example shown here, the ActionType Directions comprises an ActionAttribute that includes a command to the Smart Device (i.e., show directions in the form of green arrows).

Figure 12:
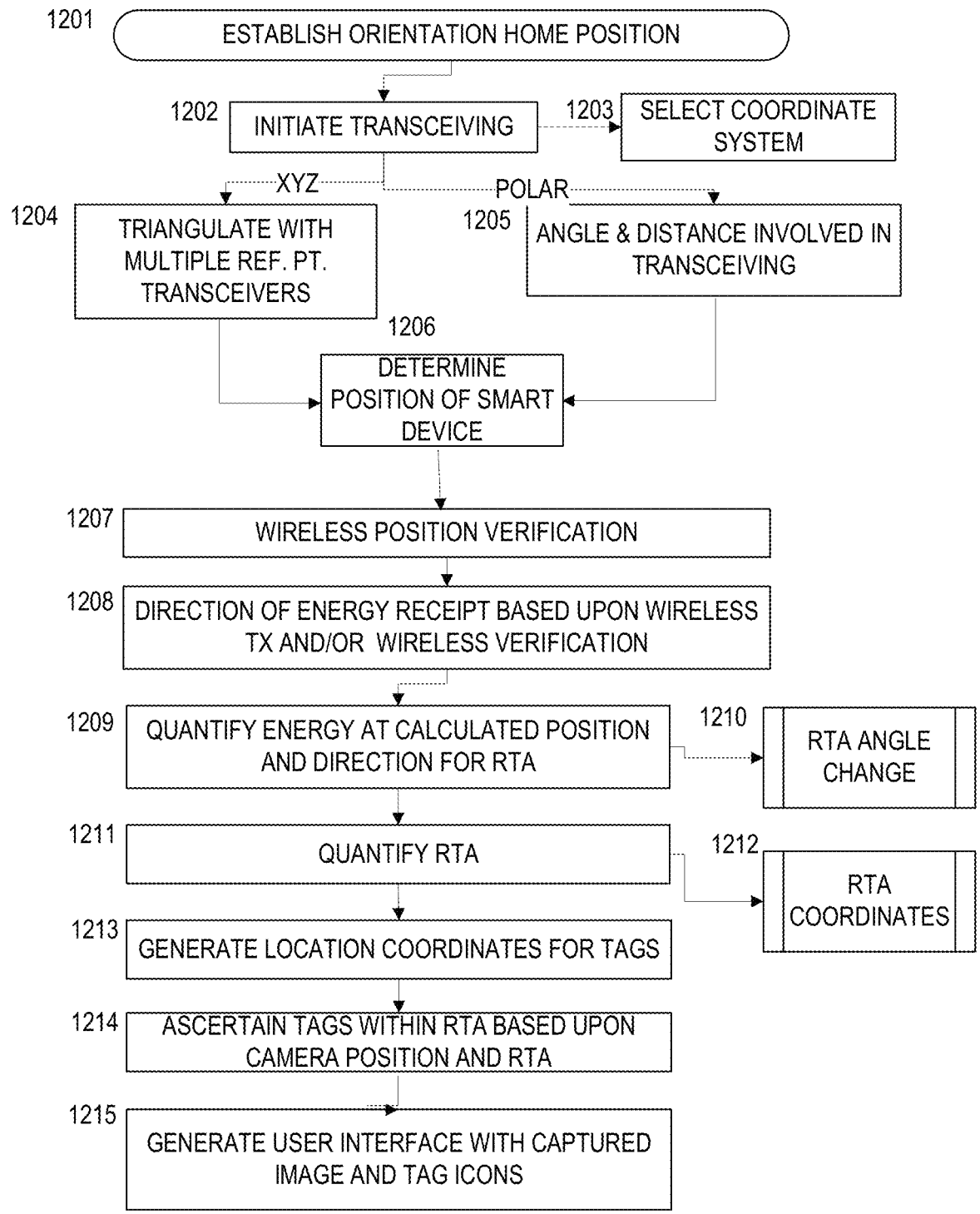
FIG. 12 illustrates additional exemplary method for displaying Radio Target Areas with Smart Devices.

Referring to FIG. 12, an illustration of alternative methods for display of information relating to RTA is provided. At the beginning of the process, a system of components which may include a smart device with a user of the smart device may be established. Amongst the various components a Home Position may be established for all the components at step 1201. The system may proceed by establishing and initiating transceiving of data and information at step 1202.

In some examples, the user may be prompted to choose a desired coordinate system for the display at step 1203. In other examples, a user interface of the system may have a setpoint function which the user may invoke to gain access to user settable parameters which may include they type of coordinate system to use, such as for example Cartesian or spherical coordinates.

In still further examples, the system may decide to default to a particular coordinate system depending on the nature of the type of data its positional reference devices may be obtaining or providing.

At step 1204, if the coordinate system was chosen as Cartesian coordinates, the system may utilize triangulation amongst multiple reference point transceivers. Alternatively, at step 1205 if the coordinate system was chosen as polar coordinates, the system may utilizes positioning systems that utilize angles and distances involved in transceiving and location. In either event, at step 1206, the position of a Sensor attached to the smart device of the user may be determined. In some examples, the system may have multiple and redundant location system. A combination of such position determinations may result in superior accuracy of an aggregated position result. Accordingly, at optional step 1207, a wireless position determination may be performed with the smart device to establish a verification of the position of the Smart Device and the Sensor attached. Referring now to step 1208, a direction that the sensor is facing in may be determined. Although there may be a number of different manners of determining orientation as have been described herein, in an example, the orientation may be determined based upon wireless transmission and/or wireless verification.

Referring now to step 1209, an energy-receiving Sensor included in the Smart Device or in logical communication with the Smart Device may be used to quantify energy levels perceivable at the position and in the direction of the Smart Device. The resulting quantification may depend on aspects of the Sensor device, but the resulting data will quantify a characteristic for the RTA.

In some embodiments, an optional step 1210 may be performed by an element of the system such as the smart device or a server in communication with the Smart Device. The element of the system may compare one or more of position information, orientation information and the image data itself to calculate an estimate of whether the RTA angle has changed for the sensing element.

In general, at step 1211, the RTA of the Sensor device used to capture the image in step 1209 may be quantified. In an optional step 1212, coordinates relating to the instant RTA of the image may be established. In some examples, this may relate to a range of three-dimensional coordinates that are addressed by the RTA of the Sensor element. In general, at step 1213, the system may look up, or in some cases generate, location coordinates for Tags that are determined to be within the quantified RTA. In some database systems that the system may have access to, real-world or virtual-world tags may be tracked in a coordinate system with a certain origin.

If the current origin established at step 1201 is offset from a particular database related origin, then one or both the coordinate system values may be converted to each other to align their respective origins. At step 1214, the Tags in an aligned coordinate system may have their positions compared to the current RTA and a selection for the set of Tags that are within the RTA may be made.

In some alternative examples, a display of all Tags that are authorized for access to the user regardless of whether they are in the RTA may be made using associated aligned coordinates as discussed in reference to step 1213.

Referring now to step 1215, in an example, the Smart Device of the user may be used to generate and display a user interface to the user based upon the captured image and the associated tag icons within the RTA. These associated Tag icons may have at least the functionality as has been discussed in reference to FIGS. 10A and 10B.

Figure 13:
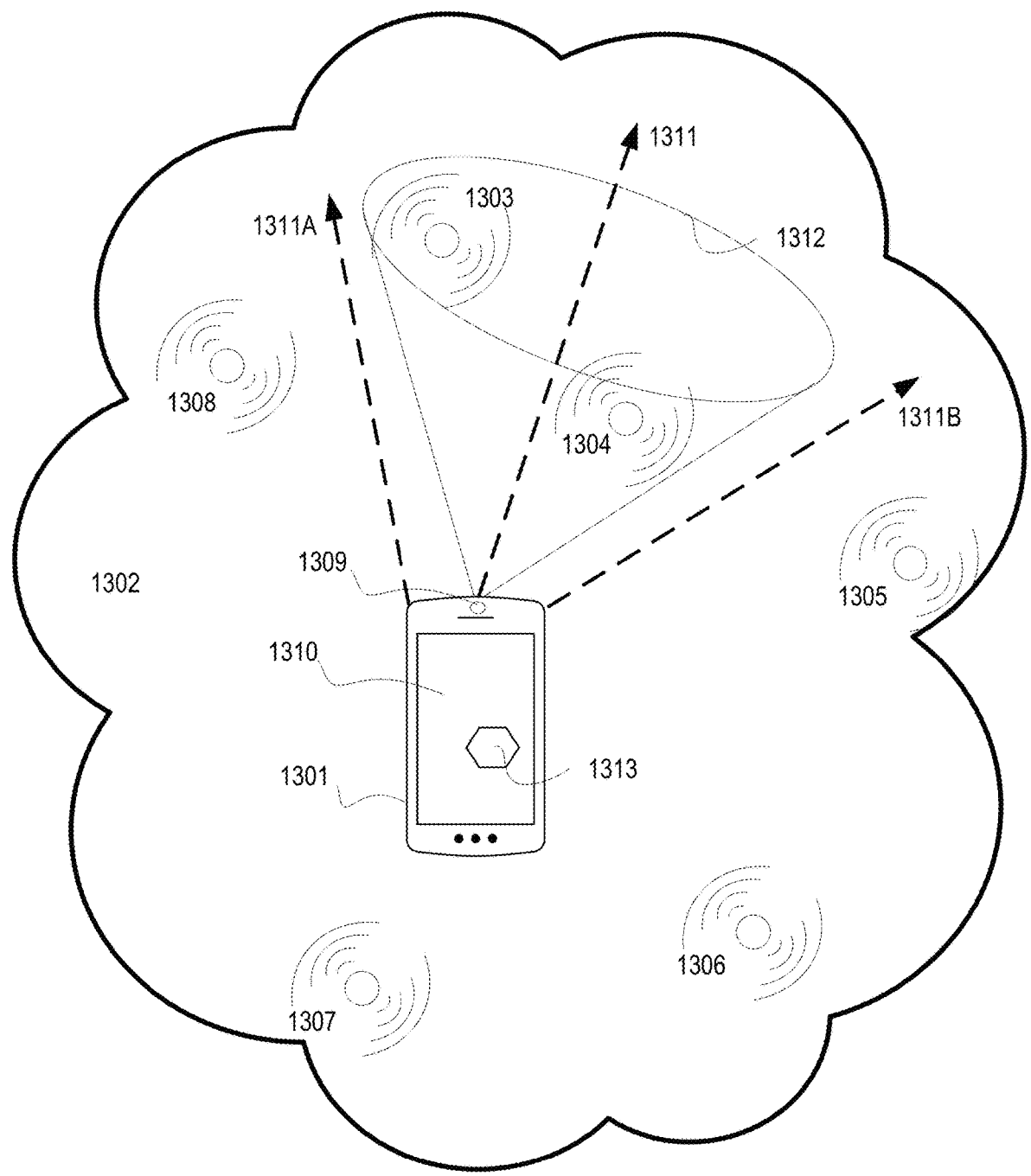
FIG. 13 illustrate exemplary aspects of Wireless Communication Areas in Radio Target Area display.

Referring now to FIG. 13, a Smart Device 1301 is illustrated within a WCA 1302. The extent of the particular WCA 1302 may be defined according to a select bandwidth and/or a particular modality of the wireless communication the Smart Device 1301 uses to transmit and receive information.

For example, bandwidths may include those associated with UWB, Wi-Fi, Bluetooth, ANT, ultrasonic, infrared and cellular modalities of communication. In general, unless otherwise constrained by physical modification such as the use of a directional antenna, or the presence of radio frequency interference from a physical object (such as objects with significant metallic content; objects with high water content; electrical fields; etc.), a WCA 1302 may include spherical area(s) emanating from one or more transceivers and/or transceiver antennas operated by the Smart Device 1301.

As discussed extensively herein, and in patent applications referenced by this application, the location of the Smart Device may be determined based upon wireless communication to and/or from the Smart Device 1301; and described via a coordinate system, such as via generation of Cartesian coordinates, or other coordinates such as: polar coordinates, spherical coordinates, and cylindrical coordinates. Modalities of wireless communications that may be referenced to generate location coordinates may include one or more of: RTT (round trip time), time of flight, RSSI (received signal strength indicator); angle of arrival, angle of departure, and other methods, equipment and modalities as have been described herein.

With the location of the Smart Device 1301 determined, a location of the WCA 1302 may be extrapolated based upon the location of the Smart Device and a range or transceiving distance the Smart Device may be capable of.

According to the present invention, a portion of the WCA 1302 may be selected as a radio target area (RTA) 1312 from which the Smart Device 1301 may receive specific bandwidths of electromagnetic radiation. In preferred embodiments, the RTA 1312 may include a frustum expanding outward in a conical shape from one or more energy receivers 1309 included in the Smart Device 1301. The frustum shaped RTA 1312 may overlap with a portion of the generally spherically shaped WCA 1302. Other shapes for a radio target area 1302 are also within the scope of this specification.

In some embodiments, a shape of the RTA 1312 may be based upon receiving capabilities of the one or more energy-receiving Sensors 1309 incorporated into or in logical communication with the Smart Device. For example, an energy-receiving Sensors 1309 with a charge coupled device (CCD) or complementary metal oxide semiconductor (CMOS) receiver may have a single plane receiving surface and be best matched with a frustum of a generally pyramidal or conical shape. Whereas, an energy receiver 1309 with multiple receiving surfaces (e.g. with multiple CCD and/or CMOS devices) may be arranged to enable a more complex shaped RTA 1312.

In some preferred embodiments, a direction of interest 1311 may intersect the RTA 1312. As discussed herein, the direction of interest 1312 may be represented by a ray or vector 1311. In addition, the direction of interest may be represented as a direction of interest area, such as a frustum defined by multiple rays or vectors 1311, 1311A, and 1311B. In various embodiments, the direction of interest 1311 area may encompass the RTA 1312 or be a subset of the RTA 1312.

A direction of interest may be determined for example via the methods and devices described herein and in referenced patent applications and may be associated with a direction based upon a ray or vector indicative of a direction of interest 1311, a direction based upon a magnetic field sensor, an accelerometer, a light beam, correlation between two Tags or Nodes, Agent gestures, or other Smart Device recognized apparatus and/or method.

One or more transceivers 1303-1305 (typically included within a Smart Device, Tag, or Node) may be located within an area defined by the RTA 1312. According to the present disclosure, a position of the transceiver 1303-1305 may be determined and a user interactive mechanism may be generated at a position of the transceiver 1303-1305 within a graphical user interface emulating aspects of the RTA 1312 on the Smart Device 1301 or another user interactive interface screen (not shown, and perhaps at a site remote to the RTA 1312).

According to the present disclosure, some portion of the RTA 1312 (which may include the entirety of the RTA 1312) may be portrayed on an Agent interface 1310, including, in some embodiments, a human-readable graphical user interface (GUI). The interface 1310 may include a representation 1313 of a particular level of electromagnetic energy received via the energy receiver 1309 and associated with a particular area of the RTA 1312. For example, energy levels of an infrared wavelength that has emanated from or reflected off of an item in the WTA 1312 and received via an infrared receiver in the Smart Device 1312 may be used to generate a heat map type interface display. Similarly, energy that has emanated from or reflected off of an item in the RTA 1312 in the 400 nm to 700 nm range and been received via a charge-coupled/or CMOS image sensing device in the Smart Device 1301 may be portrayed as a human visible image of items in the area included in the RTA 1312.

Other embodiments may include a point cloud derived from electromagnetic energy bouncing off of or emanating from items included in the RTA 1312 or a series of polygons generated based upon a LIDAR receiver in the Smart Device 1312. An Agent interface 1310 may be presented in a modality understandable to an Agent type. For example, an interface presented to a UAV or UGV may include a digital pattern and an interface presented to a human Agent may include multiple pixels or voxels generating a pattern visible to a human being.

The wireless location methods and apparatus described herein may be deployed in conjunction with one or more Transceivers 1303-1305 or Tags and/or Nodes 1306-1308 located with the WCA 1302 to generate location coordinates for the one or more Transceivers 1303-1305 or Tags and/or Nodes 1306-1308. A controller or other device operating a processor may determine which one or more Transceivers 1303-1305 or Tags and/or Nodes 1306-1308 located within the three-dimensional space included in the RTA 1312 based upon a) the location of the one or more Transceivers 1303-1305 or Tags and/or Nodes 1306-1308; and b) the location of area included in the RTA 1312.

In another aspect of the present disclosure, in some embodiments, some energy levels may not be represented in the Agent interface 1310. For example, in some embodiments, energy levels reflected off of a particular item may not be included in the Agent interface 1310. Other embodiments may only represent energy levels that have reflected off of selected items within the RTA 1312 thereby emphasizing the presence of the selected items and ignoring the presence of other items within the RTA 1312.

Figure 14:
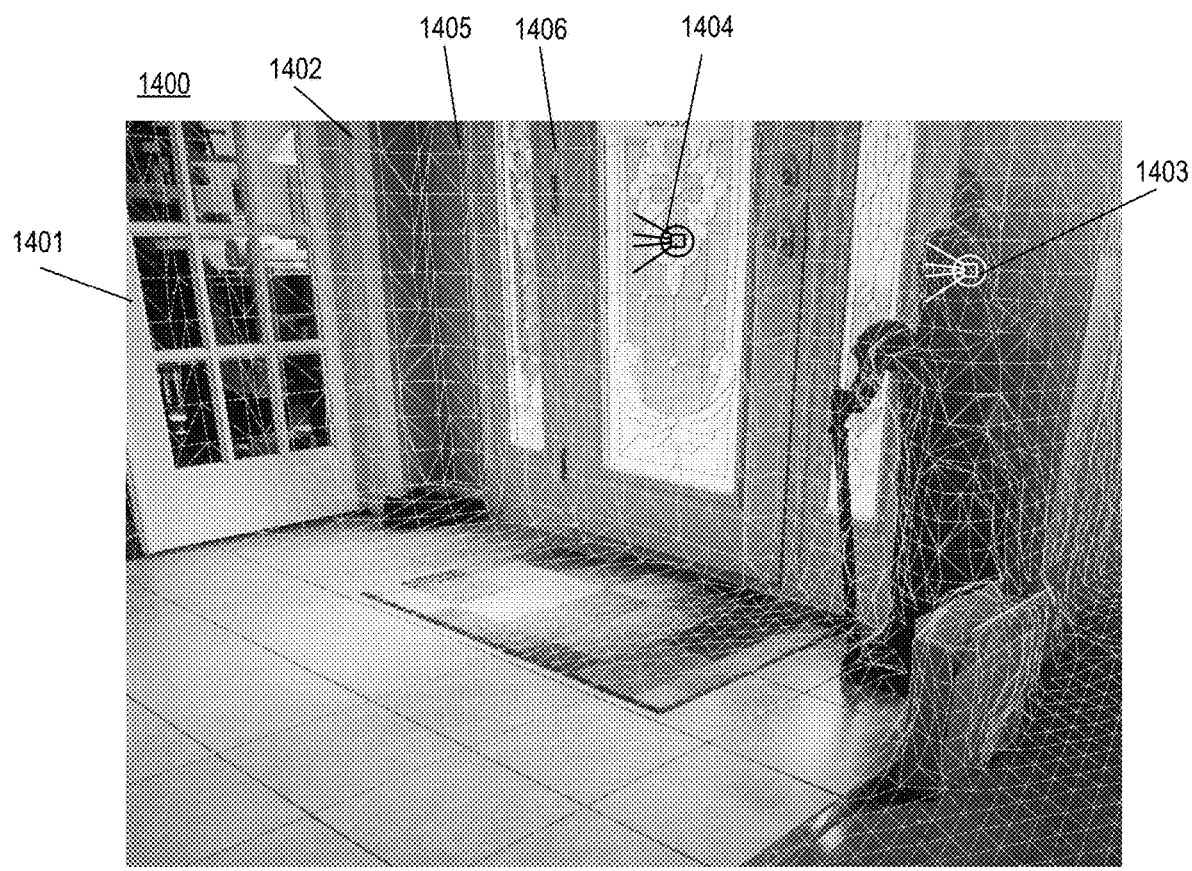
FIG. 14 illustrates a set of polygons generated via LIDAR that may be used for geospatial recognition.

As described above, some portion of the RTA 1312 may be portrayed on an Agent interface 1310, including, in some embodiments, a human readable graphical user interface (GUI), as a point cloud derived from electromagnetic energy bouncing off of or emanating from items included in the RTA 1312 or a series of polygons generated based upon a LIDAR receiver in the Smart Device 1312. An example of such a representation is shown in FIG. 14. In this example, the GUI includes a human visual image 1401 of an RTA 1400 overlaid with a series of polygons 1402 generated based upon a LIDAR receiver in the Smart Device. The LIDAR sensor illuminates the RTA 1400 with laser light and then measures the reflection with a sensor. The resulting polygons 1402 represent differences in laser return times, which provides a topographical representation of objects in the RTA In this example, Virtual Tags 1403 and 1404 are created by the Smart Device by methods described herein and icons may be present on the GUI to identify the position of the Virtual Tags 1403 and 1404. The Virtual Tags 1403 and 1404 may, for example, represent various locations of interest in the RTA, such as an object of interest (1403) or an exit or entrance (1404). The icons associated with the Virtual Tags 1403 and 1404 may be engaged or "clicked" or otherwise activated to be made operational; for the Smart Device to receive (e.g., retrieved from a database) additional information associated with the object or location of interest.

For example, if the object of interest is a statue, clicking on the icon associated with the Virtual Tag 1403 associated therewith may provide information regarding the statue, such as the history, origin, and the like. If, for example, the Virtual Tag 1404 is associated with an exit of the room, clicking the Virtual Tag may provide information on what is present in the adjacent room, or where the Smart Device is in relation to exiting the building, or any other desired information.

In some embodiments, mathematical data associated with a LIDAR rendering, such as parameters of triangles formed by various LIDAR points 1405-1406 within an associated RTA may be stored and a relative position of a smart device with the RTA 1400 may be determined based upon the recognition of similarities of the LIDAR point 1405-1406 patterns. A resolution of laser scanning involved in generation of data based upon LIDAR techniques may influence a number of date points within a selected RTA, but in general, pattern recognition and determination of an orientation of a smart device based upon LIDAR data may be much more efficient, than, for example image data based pattern recognition. In addition, the LIDAR based patterns may be formed in a "fingerprint" of an RTA, wherein it would be very rare, if not impossible to replicate the LIDAR point patterns at two disparate locations. Therefore, recognition of a point pattern may be used to identity a location of a particular RTA.

Figure 15A:
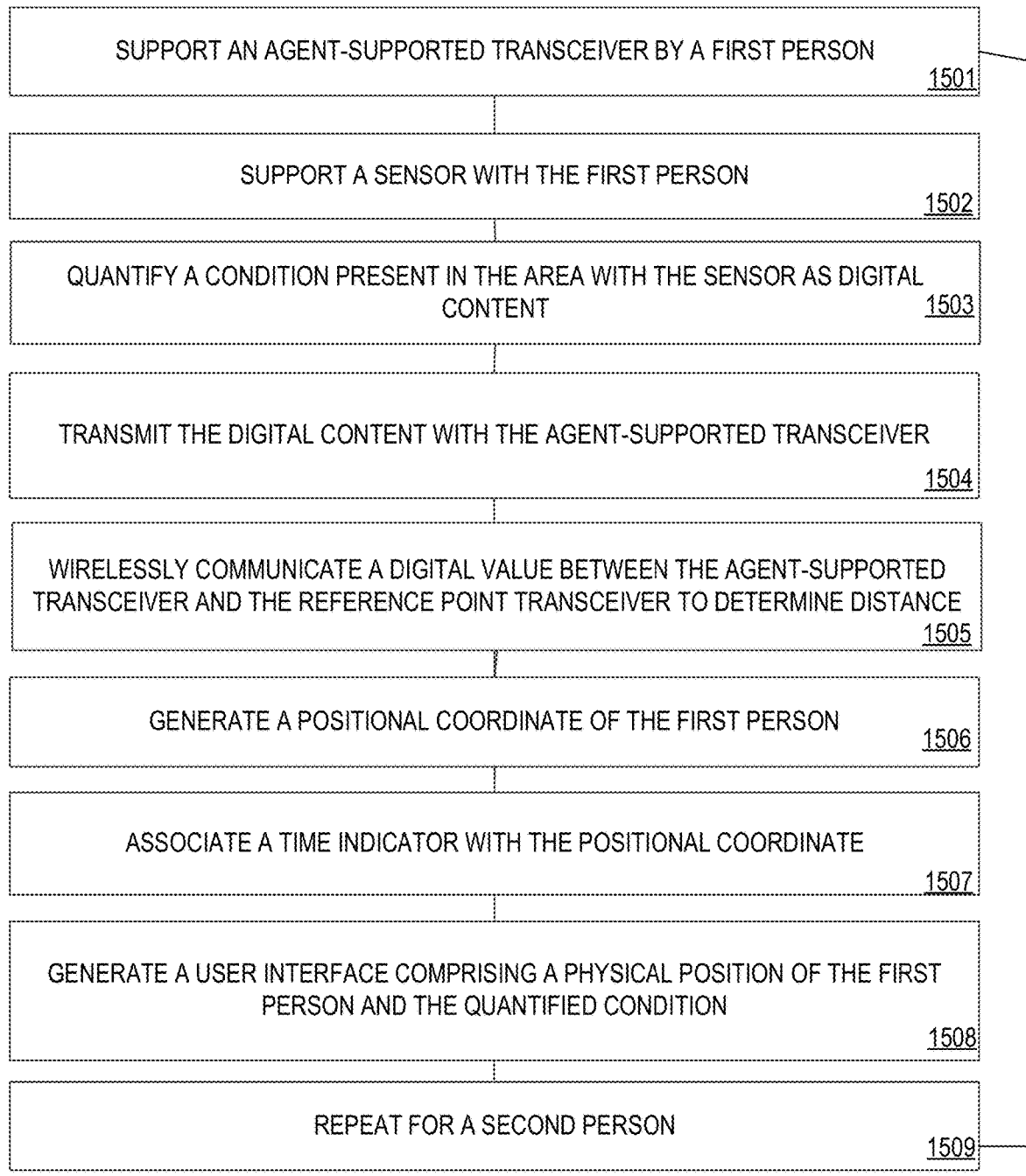
FIGS. 15A-15B illustrate method steps that may be implemented in some embodiments of the present invention.
Figure 15B:
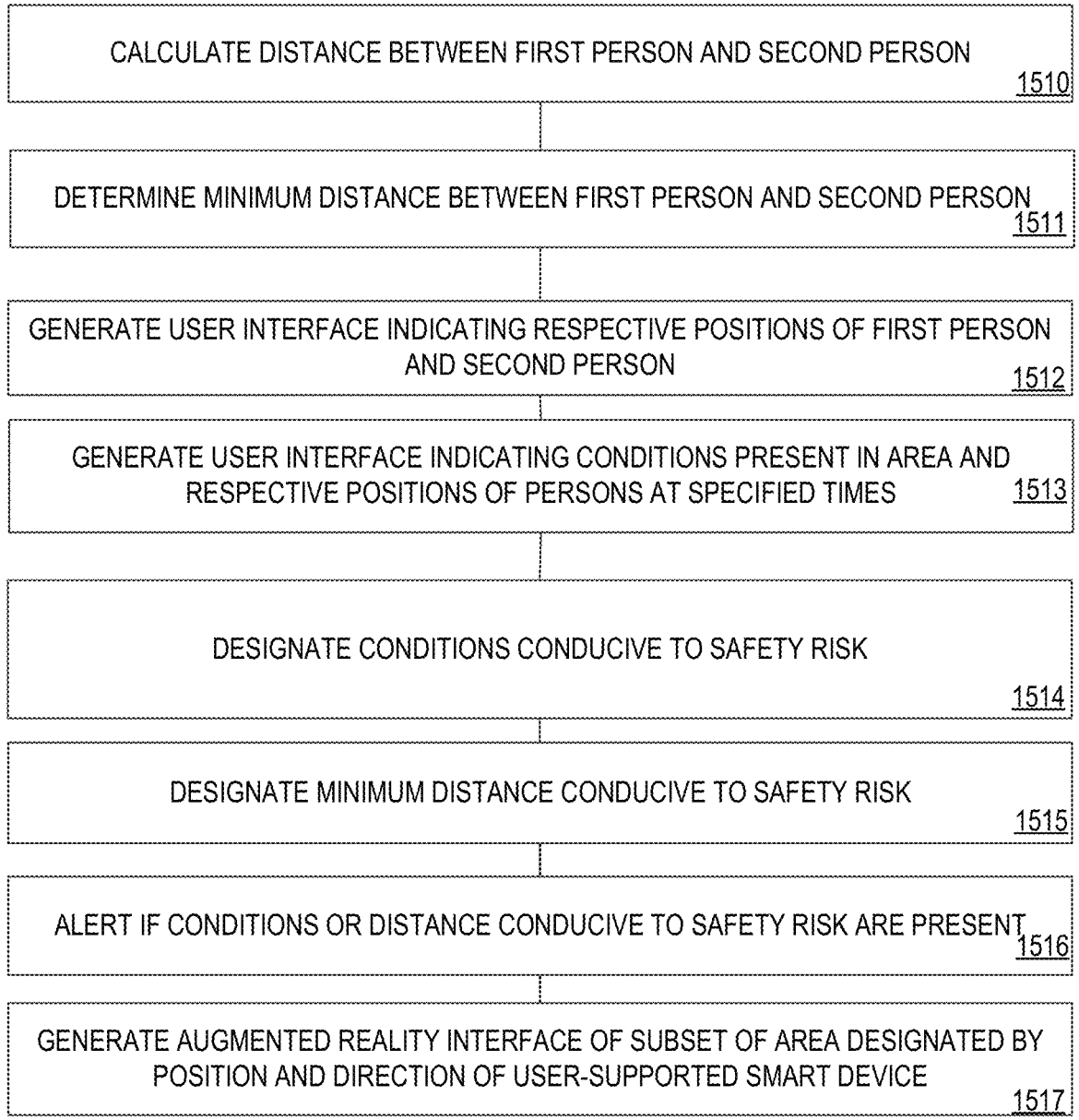

Referring now to FIGS. 15A-B, a flowchart illustrating an exemplary embodiment of a method of tracking the safety of an area is shown. At step 1501, an agent-supported transceiver may be supported by a first person. The agent-supported transceiver maybe operative to wirelessly communicate with one or more reference point transceivers. This wireless communication may be made by burst transmission, such as by ultra-wideband. As discussed above, ultra-wideband communications may determine a distance or engage in other communications with the reference point transceivers by using time-delayed signals or other burst impulses. The wireless communication may also be made by other protocols, such as Bluetooth, including Bluetooth 5.1, or other protocols enabling measurements from an antenna array associated with the transceiver, such as AoD or AoA.

At step 1502, a sensor may be movably supported by the first person. The sensor may move with the person as the person (or a portion thereof) moves. Accordingly, the sensor may change physical location as a portion of the person changes physical location. For example, if the agent-supported transceiver is a smart watch or other device worn by the first person, the agent-supported transceiver would move through a room (or other physical location) as the first person does. The sensor may be any of the sensors discussed herein, including any of the physiological sensors that may be appropriate to measure a physical characteristic of the first person, such as the first person's temperature or heart rate. In exemplary embodiments, the sensor may be in logical communication with the agent-supported transceiver.

In some embodiments, a person may be provided with a wearable item with sensors operative to quantify a physiological state in the person at a time period, such as three or seven days prior to an event. An event may include, for example, coming into contact with other persons, such as for a doctor's appoint, business meeting, sporting event, social event and the like. In this manner as the person appears at a venue for the event, accumulated data of the physiological state of the person may be analyzed and the person be granted access to the event, or directed to another destination, such as a location for further evaluation.

At step 1503, a condition present in the area may be quantified with the sensor as digital content. The condition may include a physiological state of the first person, such as temperature or heart rate, and may include a physical state of the environment accessible to the sensor. In some embodiments, this may help control for a physiological state of the person that is caused in part by an environmental state. For example, a sensor that only detects the temperature of the first person may read an elevated temperature of the first person as a fever. However, if the sensor also detects that the environmental temperature is 120° F., then the first person and/or sensor may simply be hot. In addition, the condition may be associated with a recorded time indicating a time of quantifying the condition.

At step 1504, the digital content quantifying the condition present in the area may be transmitted by the transceiver to an appropriate recipient of the condition. For example, the appropriate recipient may be a controller (including a controller on the agent-supported transceiver). The appropriate recipient may be a smart device. In exemplary embodiments, the transmission by the agent-supported transceiver to the smart device may be made via a low-power, wireless communications protocol, such as Zigby, ANT, Bluetooth Low Energy (or Bluetooth 5.1), near-field communications, or ultra-wideband. Additionally, the appropriate recipient may be a reference point transceiver. In this case, the transmission may be effected by ultra-wideband (or similar burst transmission protocols) or by Bluetooth, including Bluetooth 5.1.

At step 1505, a digital value may be wirelessly communicated between the agent-supported transceiver and the reference point transceiver. This digital value may be any appropriate value used to calculate a distance between the reference point transceiver and the agent-supported transceiver. The digital value may be sensor data or it may be timing data, such as RTT or TDOA. The digital value may relate to an angle of arrival or an angle of departure of the signal (or other means of transmitting the digital value). Where the transmission is made by burst transmission, such as ultra-wideband, the digital value may relate to a time of flight communication, such as TDOA or TDE. A second time indicator may be generated corresponding to the time at which the digital value was wirelessly communicated. This time indicator may be absolute (e.g., the communication occurred at 11:16:01.123456 on Jul. 21, 2020) or relative (e.g., the communication occurred 1.123456 seconds after the first time indicator). In some embodiments, a sensor or other controller may be precise enough to record into a data structure time indicators on the order of picoseconds or nanoseconds. This may be desirable for burst transmission protocols such as ultra-wideband, which may require such precise time measurements.

At step 1506, a positional coordinate of the first person may be generated based upon wireless communications, as described herein and in the patents and patent applications incorporated herein by reference. The positional coordinate may be in any desirable coordinate scheme. The coordinate scheme may be chosen based on the types and modalities of the signals transmitted. For example, where angles of arrival and departure are used, polar coordinates, such as cylindrical or spherical coordinates, may be desirable. In other embodiments, Cartesian coordinates may be desirable.

At step 1507, the second time indicator may be associated with the positional coordinate. This association may take place in a controller, on the agent-supported transceiver, or elsewhere.

At step 1508, a user interface may be generated. The user interface may comprise a physical position of the first person (comprising the physical coordinate in the coordinate scheme). The user interface may also comprise the quantified condition present in the area. In exemplary embodiments, a maximum time delta tolerance may be imposed between the wireless communication and the position quantification to ensure that data monitored through the interface is relatively current.

In some embodiments, the user interface may include a floorplan or other context for positions occupied by a person. For example, if a person tests positive for a contagion, it may be important to ascertain where the person has travelled during a preceding time period, such as, for example ten day, or three days. The present invention may provide an interface including a floor plan and a path traversed by the person. Some embodiments may include lag times at locations and/or during which the person was within a threshold distance to another person.

At step 1509, steps 1501-1508 may be repeated for a second person. Accordingly, a positional coordinate may be generated for the second person, along with, in some embodiments, a second quantified condition.

At step 1510, a distance between the first and second person may be computed. This distance may be computed in a variety of ways. In a first aspect, by virtue of the determination of positional coordinates associated with the first and second person, standard metrics may be used to determine the distance between the first and second person in the chosen coordinate scheme. For example, if the chosen coordinate scheme is Cartesian coordinates, the position of the first person may be expressed as $(x_1, y_1, z_1)$ and the position of the second person may be expressed as $(x_2, y_2, z_2)$. Then the distance between the first and second person is given as $\sqrt{(x_1-x_2)^2+(y_1-y_2)^2+(z_1-z_2)^2}$. Similarly, if the chosen coordinate scheme is spherical polar coordinates, the position of the first person may be expressed by radial, polar, and azimuthal coordinates $(r_1, \theta_1, \varphi_1)$ and the position of the second person may be expressed as $(r_2, \theta_2, \varphi_2)$. Then the distance between the first and second person is given as $\sqrt{(r_1^2+r_2^2-2r_1r_2[\sin\theta_1\sin\theta_2\cos(\phi_1-\phi_2)+\cos\theta_1\cos\theta_2])}$.

In a second aspect, the distance may be computed directly by transmission between the agent-supported transceivers supported by the first and second person. Like the computation of the distance between the first agent-supported transceiver and any of the reference point transceivers, this may proceed by direct communication between the transceivers via Bluetooth or ultra-wideband transmission. Using the TDOA or TDE techniques explored herein, the distance between the first and second person may be computed. This may be desirable where the first and second person are within a line-of-sight of each other or are otherwise sufficiently proximate to allow a sufficiently reliable and measurable transmission to occur between them.

This distance may be associated with a time indicator (including the time indicators generated at step 1503 and its repeated version at step 1509) and be updated periodically or based on the occurrence of an event. In some embodiments, this distance may be computed based on less than all three dimensions included in the positional coordinates. For example, if the first and second person are on separate floors of a structure, then a significant difference in an altitude coordinate may be given more or less weight.

At step 1511, a minimum distance between the first and second person is determined. This minimum may be based on the time at which the distance computed at step 1510 was minimized. In some embodiments, a threshold distance may be assessed, with an alert state triggered if the minimum distance falls below this threshold distance.

For example, if a safety factor to be monitored relates to the transmission of communicable disease, then the threshold distance may relate to authoritatively promulgated recommended distances (for example, the Center for Disease Control recommends that people remain six feet apart to minimize the transmission of COVID-19; in this case, the threshold distance may be six feet). If the first and second person have a minimum distance below the threshold distance, then the time during which the first and second person were beneath the threshold distance and the conditions present in the area at those times may be recorded and transmitted to a controller.

At step 1512, a user interface indicating respective positions of the first and second person may be generated. The user interface may display the positions in one or more coordinate systems. The user interface may also integrate external data, such as information fed into a controller by an Augmented Virtual Model. In exemplary embodiments, the user interface may also display occlusions, such as walls or other structures. These occlusions may be based on a scan of the area or an Augmented Virtual Model. The scan may proceed by LIDAR or any of the other methods described herein (and in the patents and patent applications incorporated herein by reference).

This user interface may be displayed in a variety of ways. For example, the user interface may be an augmented reality interface viewable through a smart device, headgear, or other visual means associated with one or more of the agent-supported transceivers. As another example, the user interface may merely be presented as a graph on a display that may be viewable by one or more persons.

At step 1513, the user interface (or a second user interface) may be augmented with conditions present in the area. These conditions may be based on the sensors associated with the agent-supported transceivers supported by the first and second persons or may be based on additional sensors place in the area. These sensors may transmit data to a controller, which may compile the information from which to generate the user interface.

At step 1514, conditions conducive to a safety risk may be designated. Such conditions may include any conditions that pose a deleterious risk of impairing any aspect of a person's or a structure's health, safety, or welfare. For example, the safety risk may include physiological factors indicating an illness (especially from a communicable disease) or potential danger (such as an elevated heart rate), environmental factors indicating danger (such as an excessively high temperature that may indicate a fire or barometric pressure readings indicating severe weather), excessively loud noise, or other factors.

At step 1515, based on the designated conditions conducive to a safety risk, a minimum distance associated with the condition may be determined. For example, if the safety risk relates to the contraction of an illness borne from a communicable disease, the minimum distance may be based on a recommended safety distance based on the transmission vector of the disease. (For example, the Center for Disease Control recommends that people stay six feet apart to avoid contracting COVID-19. Accordingly, if the safety risk relates to the contraction of COVID-19, then the minimum distance may be six feet.)

Similarly, if the safety risk relates to environmental factors such as fire, then the minimum distance may be absolute (e.g., 20 feet away from a sensor showing a drastic temperature spike) or relative (e.g. the distance is a function of the temperature, which allows for an approximation of the location of the fire).

At step 1516, an alert state may be triggered if conditions or distances conducive to a safety risk are present, as determined at steps 1514 and 1515. The alert state may be transmitted by a transceiver (which may be in logical connection with a controller) to a smart device of a user and/or one or more of the agent-supported transceivers, which are borne by the first and second persons. The alert state may also activate a signaling device, such as an alarm or a light proximate to the first and second person.

The alert state may be indicated in the user interface, such as in an augmented reality interface. This may be achieved by an icon (such as a ! icon), flashing message, or any other suitable attention-grabbing means. The alert state may also be transmitted in any other suitable way to alert the first or second person to a condition conducive to a safety risk that is affecting the first or second person.

At step 1517, an augmented reality interface of a subset of the area occupied by the first or second person may be designated by a position and a direction of a user-supported smart device (or similar agent-supported transceiver). This subset may indicate a location or other identifier of the first or second person, along with a condition (if present) in the area. This condition may include a physiological state of the first or second person or an environmental state of the subset of the area. Based on the determined conditions constituting a safety risk above, the augmented reality interface may indicate of the condition detected in the area constitutes a safety risk. For example, if the condition relates to a measured temperature of the first person indicating a fever, then the augmented reality interface may inform the second person (or a third agent in communication with the second person) of the safety risk caused by the first person's fever.

Figure 16:
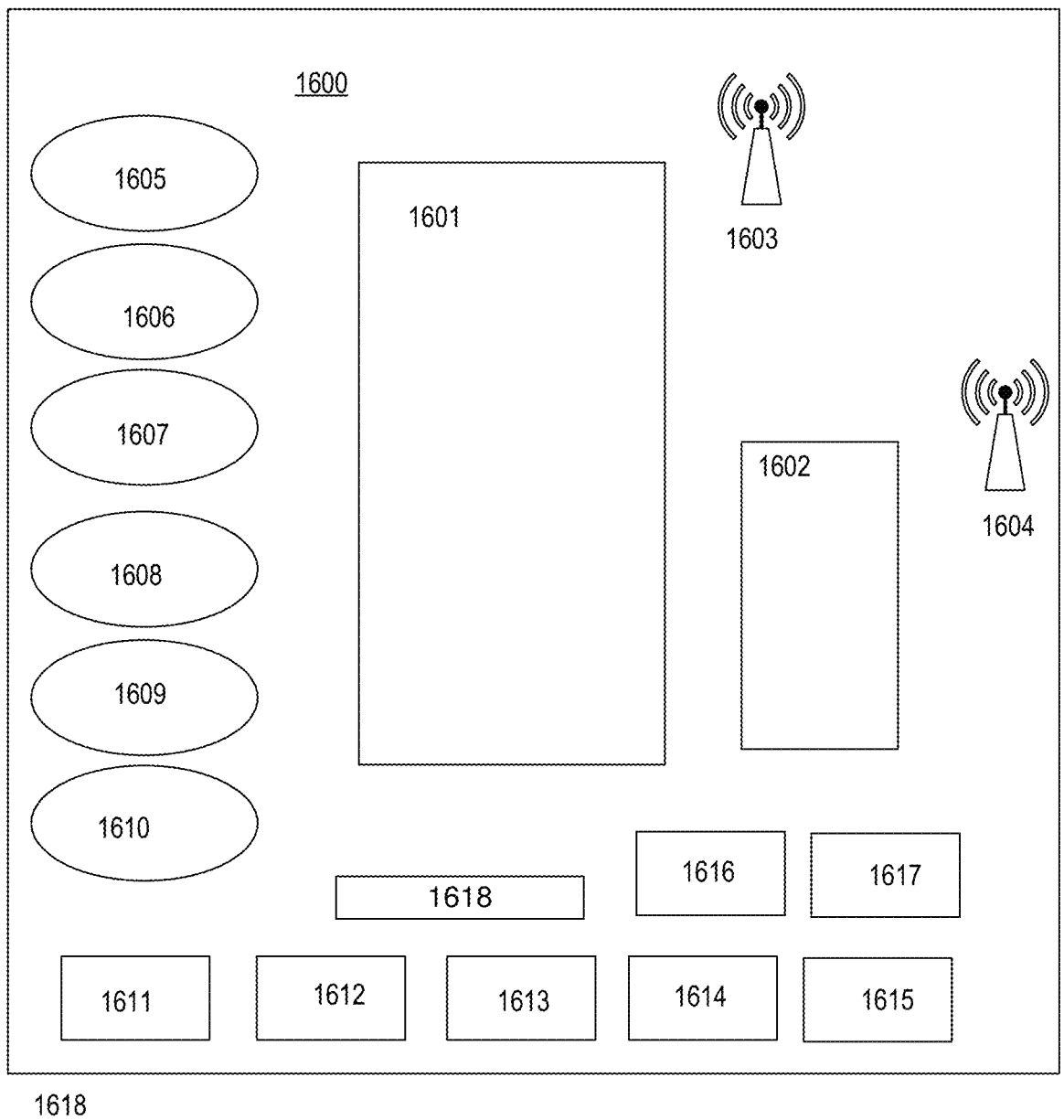
FIG. 16 illustrates a block diagram of components that may be included in some embodiments of a wearable item.

Referring now to FIG. 16, a block diagram illustrates components that may be included in various embodiments of a wearable item 1600 with one or more sensors 1605-1610 and transceivers 1603-1604. the present invention. The wearable item 1600 may include a controller 1601, in logical communication with the other components (e.g. 1601-1617) such that the controller 1601 is operative via execution of executable software to perform those method steps described herein and ascribed to a wearable item.

The wearable item will include one or more transceivers 1603-1603 which may be a same of different modality and may include a single antenna or an array(s) of antennas. The transceivers 1603-1604 may be controlled by a modality specific module 1602, such as a UWB module, a BLE module, ANT module, NFC module, cellular communications module and the like.

Sensors may include for example one or more of: an accelerometer (e.g. a 3 axis accelerometer) 1605; a skin temperature sensor 1606, which may be positioned to come into contact with the skin of a person wearing the wearable item 1600 or have non-contact access to skin surface for IR or similar sensors; a pulse oximeter sensor 1607; environmental temperature sensor 1608; environmental humidity sensor 1609 environments pressure sensor (such as a barometric sensor) 1610; a light sensor 1611; a gesture sensor 1612; one or more LEDs 1613, one or more mechanical switches 1614; a microphone (e.g. a MEMS microphone) 1615, a vibrator 1616 and/or piezo electric device; an audio signal generator 1617 (e.g. a beeper or alarm) and other devices to support the functionality, processes and method steps described herein. For example, power may supplied via a power source 1618, which may include, by way of non-limiting example a LiPo battery.

Components may be contained in and protected by packaging 1618, which may be incorporated into a specific type and style of wearable item.

Glossary

"Agent" as used herein refers to a person or automation capable of supporting a Smart Device at a geospatial location relative to a Ground Plane.

"Augmented Virtual Model" (sometimes referred to herein as "AVM"): as used herein is a digital representation of a real property parcel including one or more three-dimensional representations of physical structures suitable for use and As Built data captured descriptive of the real property parcel. An Augmented Virtual Model includes As Built Features of the structure and may include improvements and features contained within a Processing Facility.

"Bluetooth" as used herein means the Wireless Personal Area Network(WPAN) standards managed and maintained by Bluetooth SIG. Unless otherwise specifically limited to a subset of all Bluetooth standards, the Bluetooth will encompass all Bluetooth standards (e.g. Bluetooth 4.0; 5.0; 5.1 and BLE versions).

"Digital Content" as used herein refers to any artifact that may be quantified in digital form, By way of non-limiting example, digital content may include, one or more of: alphanumeric text; audio files; image data; video data; digital stories and media.

"Energy-Receiving Sensor" as used herein refers to a device capable of receiving energy from a Radio Target Area and quantifying the received energy as a digital value.

"Ground Plane" as used herein refers to horizontal plane from which a direction of interest may be projected.

"Image Capture Device" or "Scanner" as used herein refers to apparatus for capturing digital or analog image data, an Image capture device may be one or both of: a two-dimensional sensor (sometimes referred to as "2D") or a three-dimensional sensor (sometimes referred to as "3D"). In some examples an Image Capture Device includes a charge-coupled device ("CCD") sensor. "Intelligent Automation" as used herein refers to a logical processing by a device, system, machine or equipment item (such as data gathering, analysis, artificial intelligence, and functional operation) and communication capabilities.

"Multimodal" as used herein refers to the ability of a device to communication using multiple protocols and/or bandwidths. Examples of multimodal may include being capable of communication using two to more of: Ultra-Wideband, Bluetooth; Bluetooth Low Energy; Wi-Fi; Wi-Fi RT; GPS; ultrasonic; infrared protocols and/or mediums.

"Node" as used herein means a device including at least a processor, a digital storage and a wireless transceiver.

"Physical Tag" as used here shall mean a physical device with a transceiver capable of wireless communication sufficient to determine a geospatial position of the device. The Physical Tag may also be associated with a data set that is not contingent upon the geospatial location of the physical device.

"Radio Target Area" an area from which an energy-receiving Sensor will receive energy of a type and bandwidth that may be quantified by the energy-receiving Sensor.

"Ray" as used herein refers to a straight line including a starting point and extending indefinitely in a direction.

"Sensor" as used herein refers to one or more of a solid state, electro-mechanical, and mechanical device capable of transducing a physical condition or property into an analogue or digital representation and/or metric.

"Smart Device" as used herein includes an electronic device including, or in logical communication with, a processor and digital storage and capable of executing logical commands.

"Smart Receptacle" as used herein includes a case or other receiver of a smart device with components capable of receiving wireless transmissions from multiple wireless positional reference transceivers. In some embodiments, the smart receptacle will include a wireless transmitter and/or a physical connector for creating an electrical path for carrying one or both of electrical power and logic signals between an associated Smart Device and the Smart Receptacle.

"Structure" as used herein refers to a manmade assembly of parts connected in an ordered way. Examples of a Structure in this disclosure include a building; a sub-assembly of a building; a bridge, a roadway, a train track, a train trestle, an aqueduct; a tunnel a dam, and a retainer berm.

"Tag" as used herein refers to digital content and access rights associated with a geospatial position "Transceive" as used herein refers to an act of transmitting and receiving data.

"Transceiver" as used herein refers to an electronic device capable of one or both of wirelessly transmitting and receiving data.

"Vector" as used herein refers to a magnitude and a direction as may be represented and/or modeled by a directed line segment with a length that represents the magnitude and an orientation in space that represents the direction.

"Virtual Tag" as used here shall mean digital content associated with a location identified via positional coordinates.

"Wearable" as used herein means capable of being removably positioned on a human being such that an item that is worn by a person is supported by the person; and moves about with the person, as an area of the person on which the item being worn moves about. For example, a wearable item that comprises a wrist band may be positioned on a wrist of a person and will move with the person's wrist as the wrist moves. Movement of the wrist may be accomplished as the person walks and/or as the person's arm is moved relative to the person's body. Similarly, a wearable item that comprises headgear will move as the person walks and/or as the person moves their head.

"Wireless Communication Area" (sometimes referred to as "WCA") as used herein means an area through which wireless communication may be completed. A size of a WCA may be dependent upon a specified modality of wireless communication and an environment through which the wireless communication takes place. In discussion (and as illustrated), a WCA may be portrayed as being spherical in shape, however in a physical environment a shape of a WCA may be amorphous or of changing shape and more resemble a cloud of thinning density around the edges.

Data analysis techniques, such as a Fast Fourier Transform; structured queries; and unstructured queries may yield relevant pattern information.

A number of embodiments of the present disclosure have been described. While this specification contains many specific implementation details, there should not be construed as limitations on the scope of any disclosures or of what may be claimed, but rather as descriptions of features specific to particular embodiments of the present disclosure. While embodiments of the present disclosure are described herein by way of example using several illustrative drawings, those skilled in the art will recognize the present disclosure is not limited to the embodiments or drawings described. It should be understood the drawings and the detailed description thereto are not intended to limit the present disclosure to the form disclosed, but to the contrary, the present disclosure is to cover all modification, equivalents and alternatives falling within the spirit and scope of embodiments of the present disclosure as defined by the appended claims.

The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including but not limited to. To facilitate understanding, like reference numerals have been used, where possible, to designate like elements common to the figures.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted the terms "comprising", "including", and "having" can be used interchangeably.

Certain features that are described in this specification in the context of separate embodiments can also be implemented in combination in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while method steps may be depicted in the drawings in a particular order, this should not be understood as requiring that such operations be performed in the particular order shown or in a sequential order, or that all illustrated operations be performed, to achieve desirable results.

Certain features that are described in this specification in the context of separate embodiments can also be implemented in combination in a single embodiment. Conversely, various features that are described in the context of a single embodiment can also be implemented in combination in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order show, or sequential order, to achieve desirable results. In certain implementations, multitasking and parallel processing may be advantageous. Nevertheless, it will be understood that various modifications may be made without departing from the spirit and scope of the claimed disclosure.

What is claimed is:

1. An apparatus, supportable by a first person, for tracking safety conditions in an area, the apparatus comprising:
   a controller comprising a processor and a digital storage, said controller in logical communication with a user interface display;
   a first agent-supported transceiver movably supportable by an agent located at a first geospatial position, which first agent-supported transceiver is in logical communication with the controller and operative to transmit or receive data from a reference point transceiver;
   a wireless communication device in logical communication with the controller;
   executable code stored on the digital storage and executable by the processor to cause the controller to:
   a. receive from a first sensor movably supported by the first person a quantification of a condition present in the area with the first sensor, wherein the quantification is digital content, and associate a first time indicator with the condition;
   b. transmit a wireless communication via the wireless communication device to a receiver the digital content quantifying the condition present in the area with the agent-supported transceiver;
   c. wirelessly communicate between the first agent-supported transceiver and a reference point transceiver a digital value to calculate a distance between the first agent-supported transceiver and the reference point transceiver;
   d. generate a positional coordinate of the first person based upon the wireless communication;
   e. associate a second time indicator with the positional coordinate and the time at which the wireless communication occurred;
   f. generate a display on the user interface comprising a physical position of the first person and the quantified condition present in the area;
   g. update the user interface to indicate conditions present in the area and respective positions of persons at specified times;
   h. designate one or more conditions conducive to a safety risk; and
   i. based upon a condition conducive to a safety risk, trigger an alarm state.

2. The apparatus of claim 1, wherein the executable code is further operative to cause the controller to:
   m. receive from a second agent-supported transceiver supported by a second person a positional coordinate corresponding to a location of the second person;
   n. calculate a distance between the first person and the second person at one or more time instances;
   o. determine a minimum distance between the first person and the second person; and
   p. update the user interface to indicate respective positions of the first person and the second person.

3. The apparatus of claim 2, wherein the executable code is further operative to cause the controller to:
   q. associate one or more threshold minimum distances with the one or more conditions conducive to a safety risk; and
   r. based upon a condition conducive to a safety risk or a minimum distance between the first and second person being lower than a threshold minimum distance associated with a condition conducive to a safety risk, trigger an alarm state.

4. The apparatus of claim 1, wherein the first agent-supported transceiver is capable of transmitting and receiving via a burst transmission protocol.

5. The apparatus of claim 4, wherein the burst transmission protocol comprises ultra-wideband.

6. The apparatus of claim 1, wherein the first agent-supported transceiver is capable of transmitting and receiving via Bluetooth.

7. The apparatus of claim 1, wherein the first agent-supported transceiver is in logical communication with a smart device.

8. The apparatus of claim 7, wherein the first agent-supported transceiver is capable of transmitting and receiving via a low-power wireless communication protocol.

9. The apparatus of claim 8, wherein the low-power wireless communication protocol comprises Bluetooth Low Energy.

10. The apparatus of claim 8, wherein the low-power wireless communication protocol comprises near field communications.

11. The apparatus of claim 10, wherein the first agent-supported transceiver is capable of transmitting and receiving via ultra-wideband.

12. The apparatus of claim 1, wherein the positional coordinate comprises a Cartesian coordinate.

13. The apparatus of claim 1, wherein the positional coordinate comprises a cylindrical polar coordinate.

14. The apparatus of claim 1, wherein the positional coordinate comprises a spherical polar coordinate.

15. The apparatus of claim 1, wherein the alarm state comprises activating a signaling device.

16. The apparatus of claim 1, wherein the executable code is further operative to, based upon the triggering of the alarm state, cause the first agent-supported transceiver to transmit a signal to a smart device.

17. The apparatus of claim 1, wherein the executable code is further operative to, based upon the triggering of the alarm state, cause the user interface to display an indicator.

18. The apparatus of claim 1, wherein the executable code is further operative to, based upon the triggering of the alarm state, cause the first agent-supported transceiver to transmit a notification to one or both of: the first and a second person.

19. The apparatus of claim 1, wherein the executable code is further operative to cause the controller to generate an augmented reality interface of a subset of the area based on the position and direction of orientation of an agent-supported smart device.

20. The apparatus of claim 19, wherein the augmented reality interface further comprises an identifier associated with one or both of the first and a second person.

21. The apparatus of claim 20, wherein the augmented reality interface further comprises an indication of a condition associated with one or both of the first and second person.

22. The apparatus of claim 21, wherein the condition comprises the condition conducive to a safety risk.

23. The apparatus of claim 1, wherein the sensor comprises a thermoelectric device, and the condition comprises a body temperature exceeding a specified value.

24. The apparatus of claim 1, wherein the sensor comprises a heartrate monitor, and the condition comprises an elevated heartbeat.

25. The apparatus claim 2, wherein the minimum distance is six feet.

\* \* \* \* \*